(12) United States Patent
Gabel et al.

(10) Patent No.: US 8,366,733 B2
(45) Date of Patent: Feb. 5, 2013

(54) APPLICATOR INSTRUMENTS FOR CONTROLLING BLEEDING AT SURGICAL SITES AND METHODS THEREFOR

(75) Inventors: Jonathan B. Gabel, Randolph, NJ (US); Jason C. Livingston, Scotch Plains, NJ (US); Dwayne Looney, Flemington, NJ (US)

(73) Assignee: Ethicon, Inc., Somerville, NJ (US)

( * ) Notice: Subject to any disclaimer, the term of this patent is extended or adjusted under 35 U.S.C. 154(b) by 431 days.

(21) Appl. No.: 12/057,726

(22) Filed: Mar. 28, 2008

(65) Prior Publication Data

US 2009/0248056 A1 Oct. 1, 2009

(51) Int. Cl.
*A61M 29/00* (2006.01)
(52) U.S. Cl. .................................................. 606/192
(58) Field of Classification Search .............. 606/192, 606/151, 200, 213, 191, 190; 604/14, 102.02, 604/509, 96.01; 623/23.51
See application file for complete search history.

(56) References Cited

U.S. PATENT DOCUMENTS

| | | |
|---|---|---|
| 3,760,808 A | 9/1973 | Bleuer |
| 3,857,395 A | 12/1974 | Johnson et al. |
| 4,900,303 A | 2/1990 | Lemelson |
| 5,147,374 A | 9/1992 | Fernandez |
| 5,176,692 A | 1/1993 | Wilk et al. |
| 5,281,197 A | 1/1994 | Arias et al. |
| 5,395,383 A | 3/1995 | Adams et al. |
| 5,397,332 A | 3/1995 | Kammerer et al. |
| 5,405,360 A | 4/1995 | Tovey |
| 5,419,765 A | 5/1995 | Weldon et al. |
| 5,626,601 A | 5/1997 | Gershony et al. |
| 5,645,566 A * | 7/1997 | Brenneman et al. .......... 606/213 |
| 5,653,726 A * | 8/1997 | Kieturakis .................... 606/190 |
| 5,692,642 A | 12/1997 | Brattesani |
| 6,027,471 A | 2/2000 | Fallon et al. |
| 6,039,721 A * | 3/2000 | Johnson et al. ............... 604/508 |

(Continued)

FOREIGN PATENT DOCUMENTS

| | | |
|---|---|---|
| EP | 0948932 | 10/1999 |
| EP | 2002779 | 12/2008 |

(Continued)

OTHER PUBLICATIONS

International Search Report re: PCT/US2009/037270 dated Oct. 7, 2009.

(Continued)

*Primary Examiner* — Gary Jackson
*Assistant Examiner* — Katrina Stransky
(74) *Attorney, Agent, or Firm* — David R. Crichton

(57) ABSTRACT

An instrument for controlling bleeding includes an outer shaft having a central lumen extending between proximal and distal ends thereof, and an inner shaft disposed within the central lumen of the outer shaft, the inner shaft having a central lumen extending between proximal and distal ends thereof. The instrument has an inflatable balloon with a proximal end secured to the outer shaft and a distal end that is inverted and secured to the inner shaft. In one embodiment, the balloon has a spherical shape when the outer and inner shafts are in a first position and a toroidal shape when the outer and inner shafts are in a second position. The instrument includes an actuator for discharging a flowable material from the central lumen. In one embodiment, the instrument includes a stylet having barb-like features to attach a hemostat to the distal end of the instrument.

26 Claims, 43 Drawing Sheets

U.S. PATENT DOCUMENTS

| | | | |
|---|---|---|---|
| 6,156,045 A | 12/2000 | Ulbrich et al. | |
| 6,251,093 B1* | 6/2001 | Valley et al. | 604/97.03 |
| 6,475,177 B1 | 11/2002 | Suzuki | |
| 6,613,070 B2 | 9/2003 | Redmond et al. | |
| 6,695,856 B2 | 2/2004 | Kieturakis et al. | |
| 6,706,051 B2 | 3/2004 | Hudson et al. | |
| 6,764,497 B2* | 7/2004 | Fogarty et al. | 606/190 |
| 6,780,183 B2* | 8/2004 | Jimenez et al. | 606/41 |
| 6,989,018 B2* | 1/2006 | Fogarty et al. | 606/190 |
| 7,018,392 B2* | 3/2006 | Hudson et al. | 606/192 |
| 7,166,133 B2 | 1/2007 | Evans et al. | |
| 7,175,646 B2* | 2/2007 | Brenneman et al. | 606/213 |
| 7,192,436 B2* | 3/2007 | Sing et al. | 606/213 |
| 7,331,979 B2 | 2/2008 | Khosravi et al. | |
| 7,789,893 B2* | 9/2010 | Drasler et al. | 606/213 |
| 2003/0040705 A1 | 2/2003 | Dorros et al. | |
| 2004/0006305 A1* | 1/2004 | Hebert et al. | 604/96.01 |
| 2004/0019323 A1* | 1/2004 | Carter et al. | 604/97.03 |
| 2004/0249342 A1 | 12/2004 | Khosravi et al. | |
| 2004/0267307 A1 | 12/2004 | Bagaoisan et al. | |
| 2004/0267308 A1* | 12/2004 | Bagaoisan et al. | 606/213 |
| 2005/0113858 A1 | 5/2005 | Deutsch | |
| 2005/0149099 A1* | 7/2005 | Yamano et al. | 606/192 |
| 2005/0149117 A1* | 7/2005 | Khosravi et al. | 606/215 |
| 2005/0155608 A1 | 7/2005 | Pavcnik et al. | |
| 2005/0222605 A1 | 10/2005 | Greenhalgh et al. | |
| 2005/0234499 A1* | 10/2005 | Olson et al. | 606/192 |
| 2005/0245876 A1* | 11/2005 | Khosravi et al. | 604/164.1 |
| 2006/0034930 A1 | 2/2006 | Khosravi et al. | |
| 2007/0021774 A1 | 1/2007 | Hogendijk | |
| 2007/0088380 A1* | 4/2007 | Hirszowicz et al. | 606/194 |
| 2007/0162067 A1* | 7/2007 | Lunsford et al. | 606/192 |
| 2007/0173785 A1 | 7/2007 | Ostroot | |
| 2007/0213670 A1 | 9/2007 | Gabel et al. | |
| 2007/0255306 A1* | 11/2007 | Conlon et al. | 606/192 |
| 2007/0260179 A1 | 11/2007 | Sholev et al. | |
| 2008/0086083 A1 | 4/2008 | Towler | |

FOREIGN PATENT DOCUMENTS

| | | |
|---|---|---|
| GB | 651524 | 4/1951 |
| JP | 10-328306 | 12/1998 |
| NL | 1016743 | 12/2001 |
| WO | WO 01/76678 | 10/2001 |
| WO | WO 2007/004221 | 1/2007 |

OTHER PUBLICATIONS

International Search Report re: PCT/US2009/037276 dated Oct. 7, 2009.

International Search Report re: PCT/US2009/038218 dated Jun. 17. 2009.

* cited by examiner

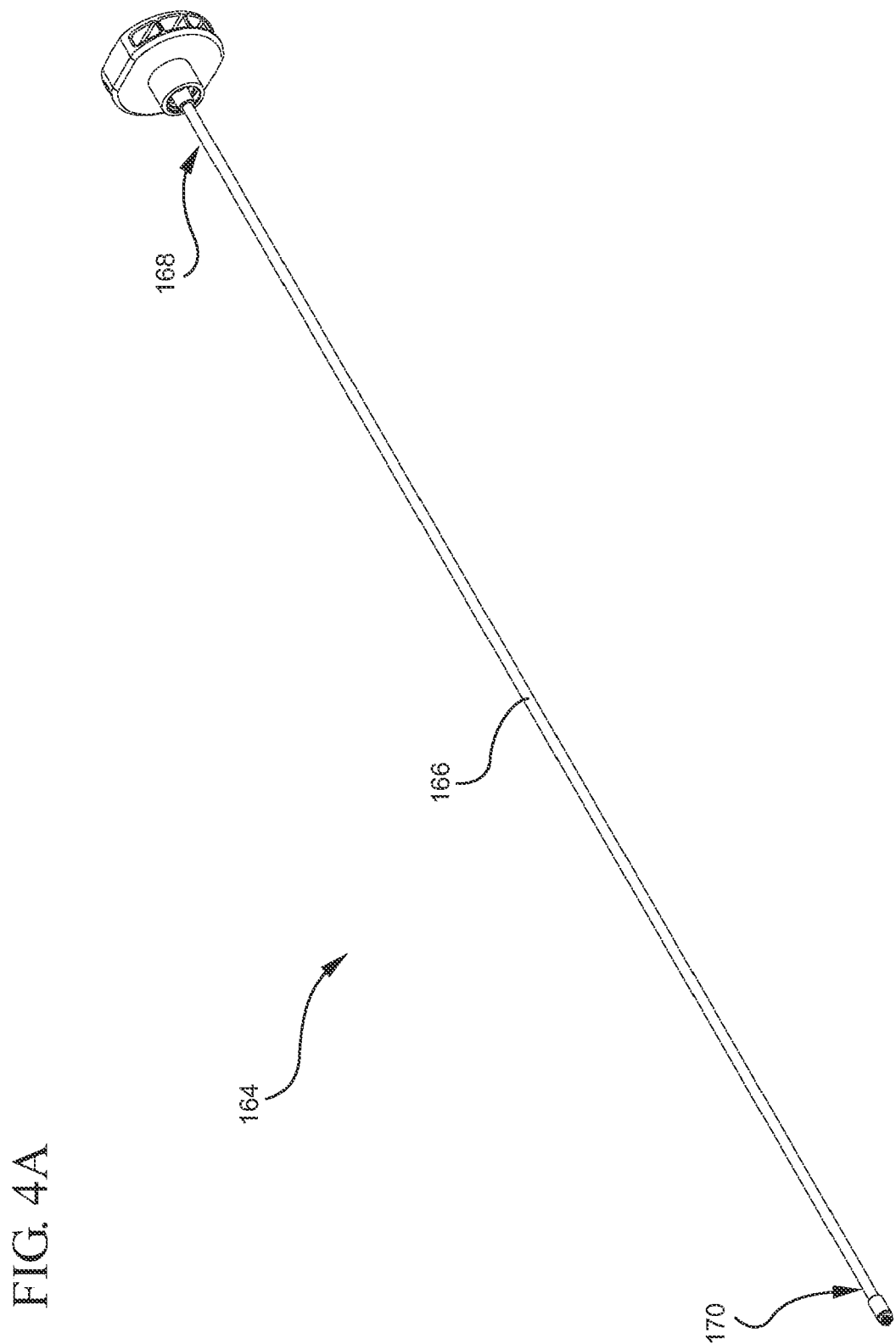

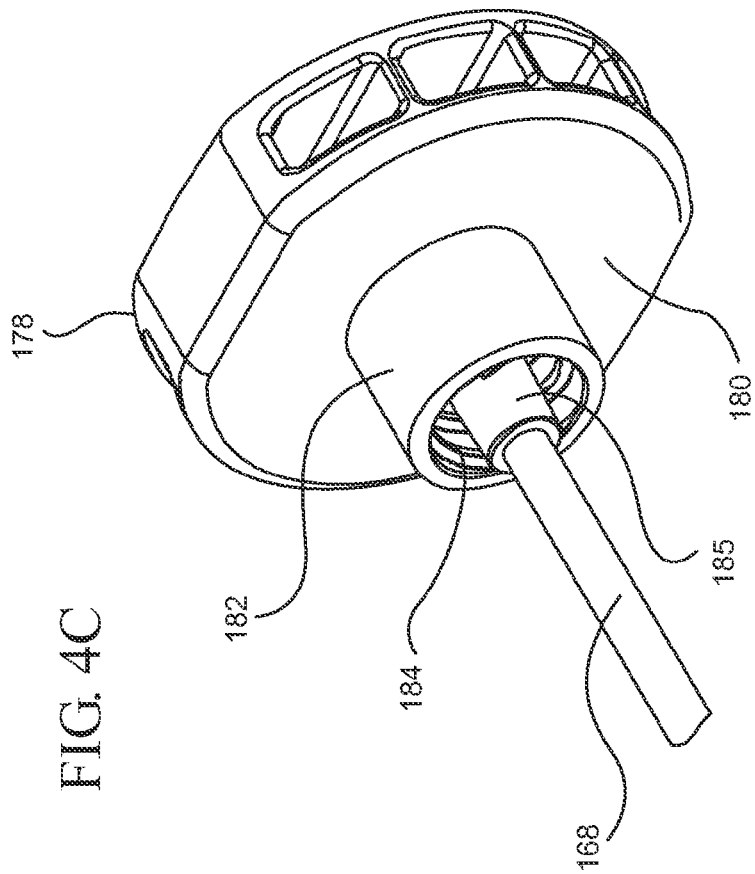
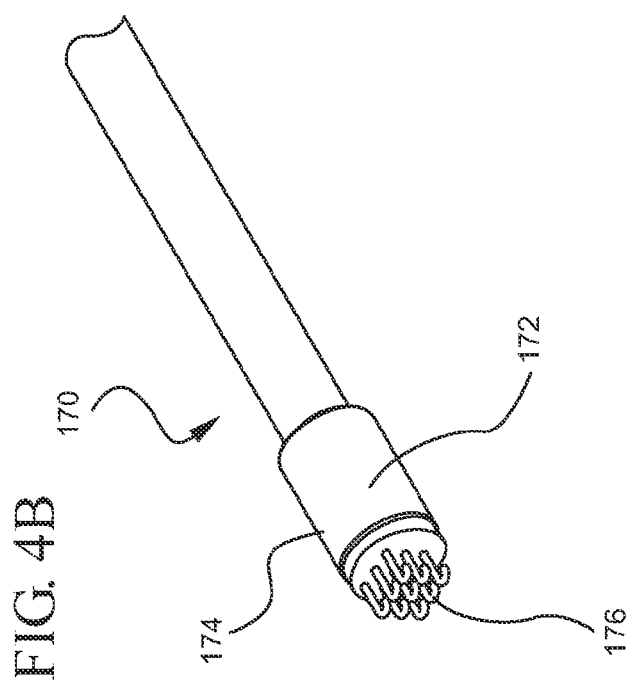
FIG. 4B
FIG. 4C

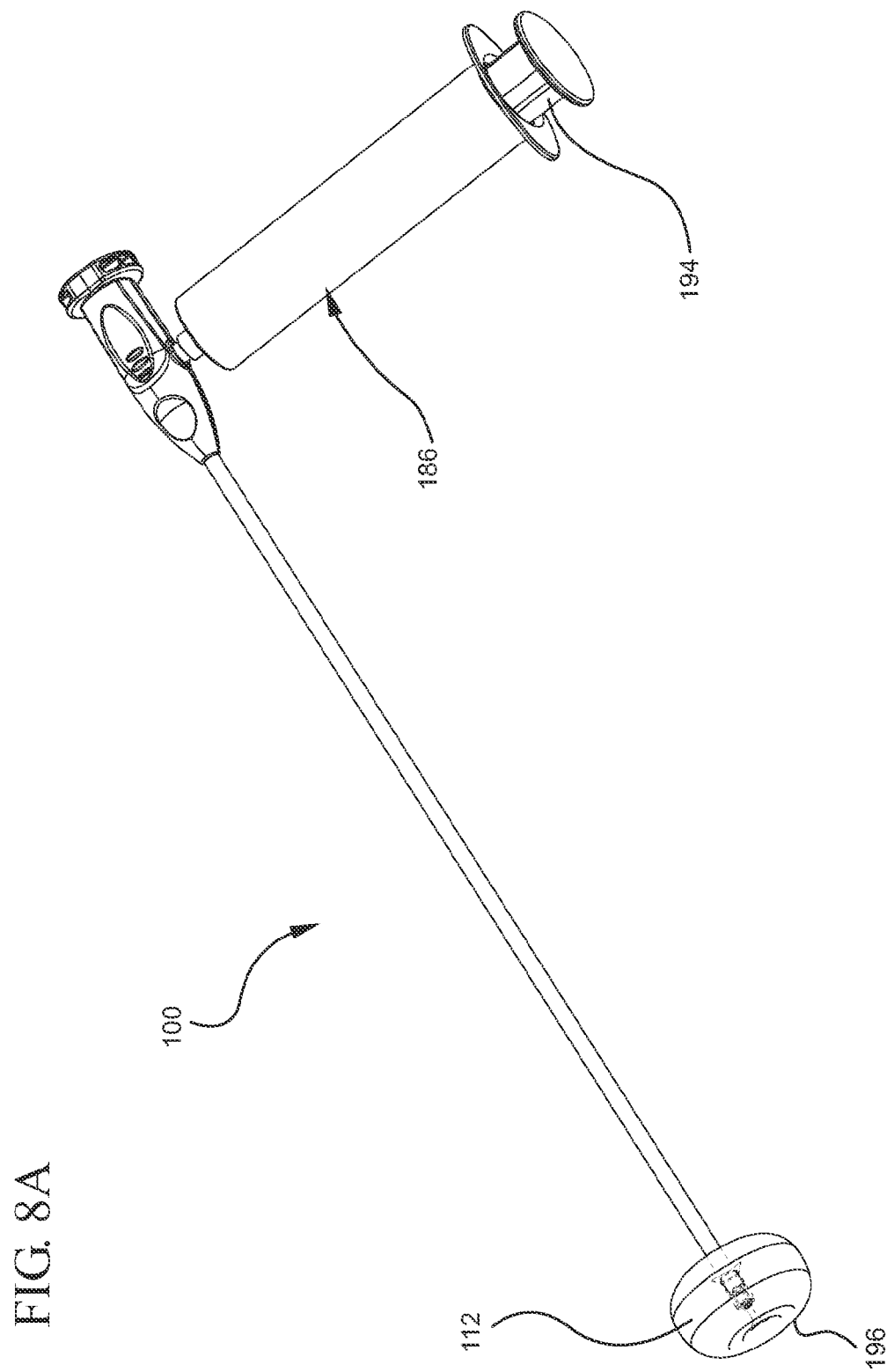

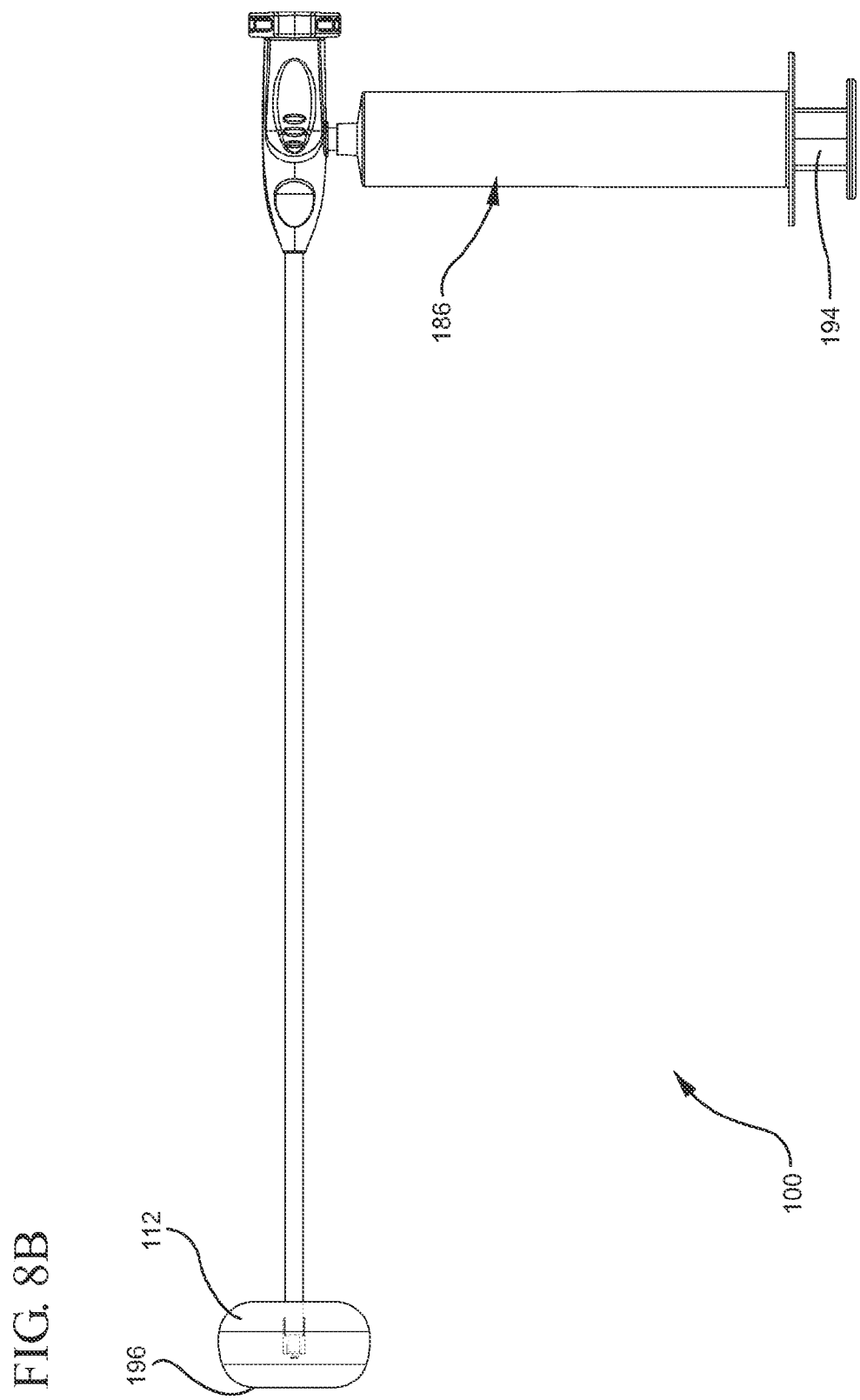

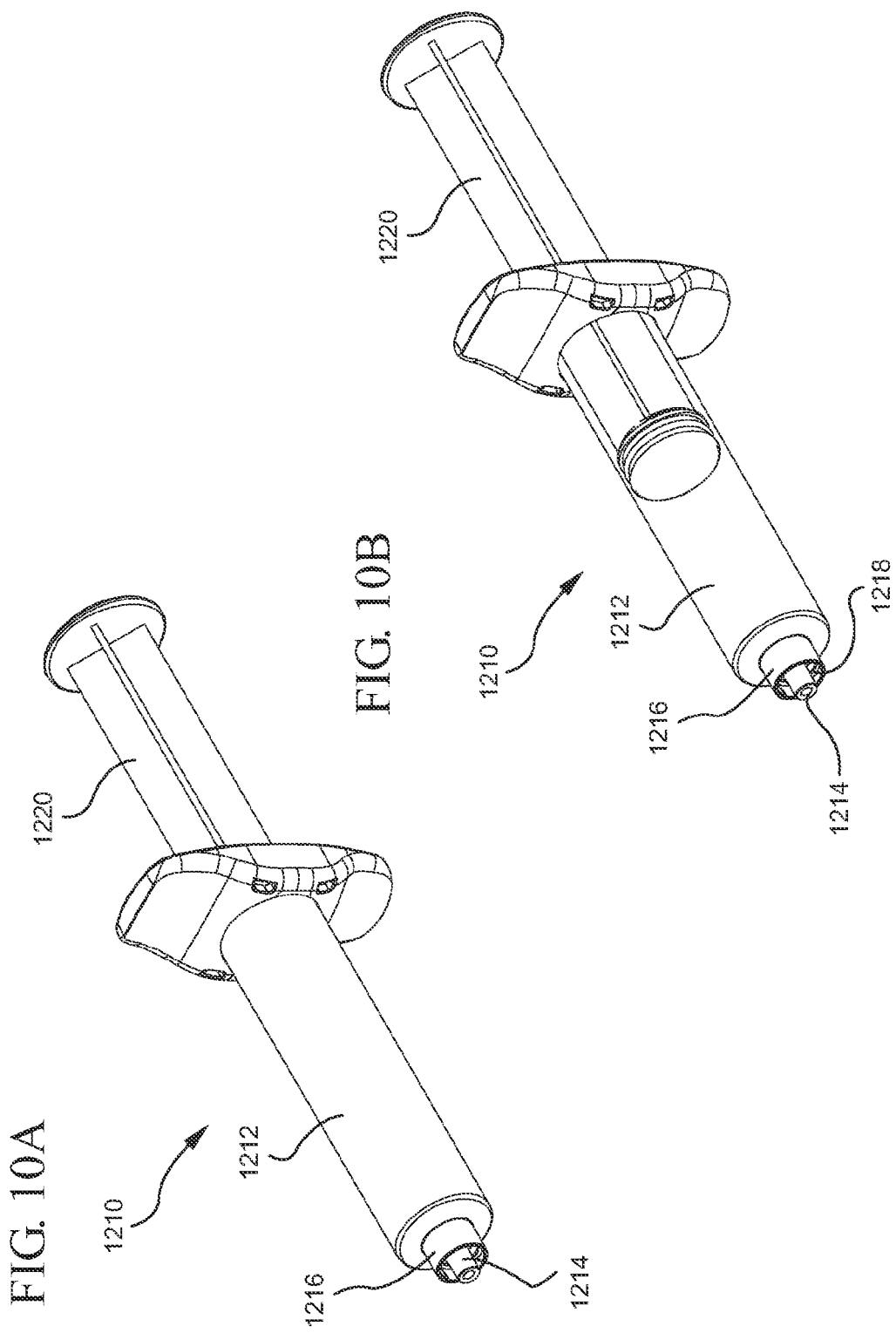

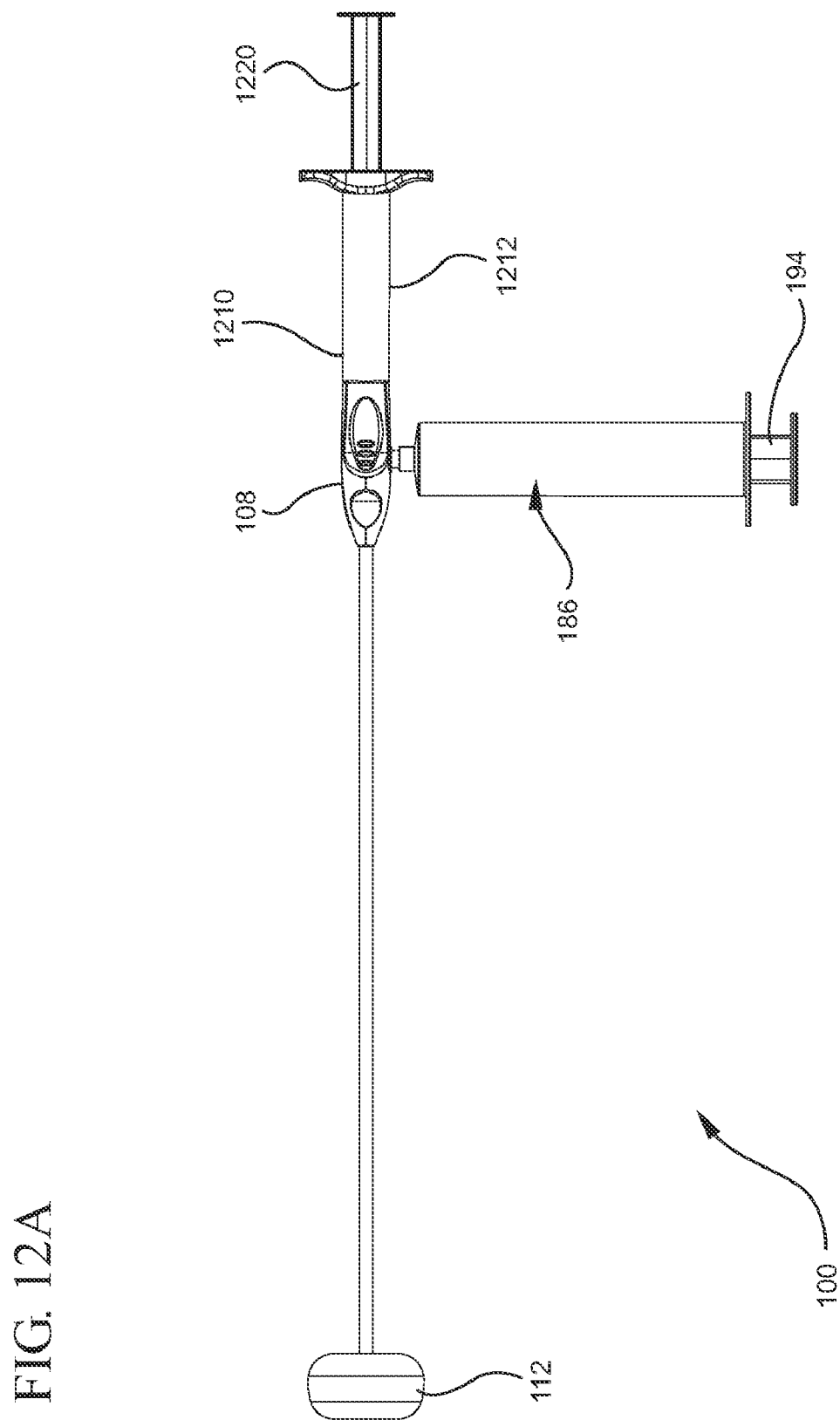

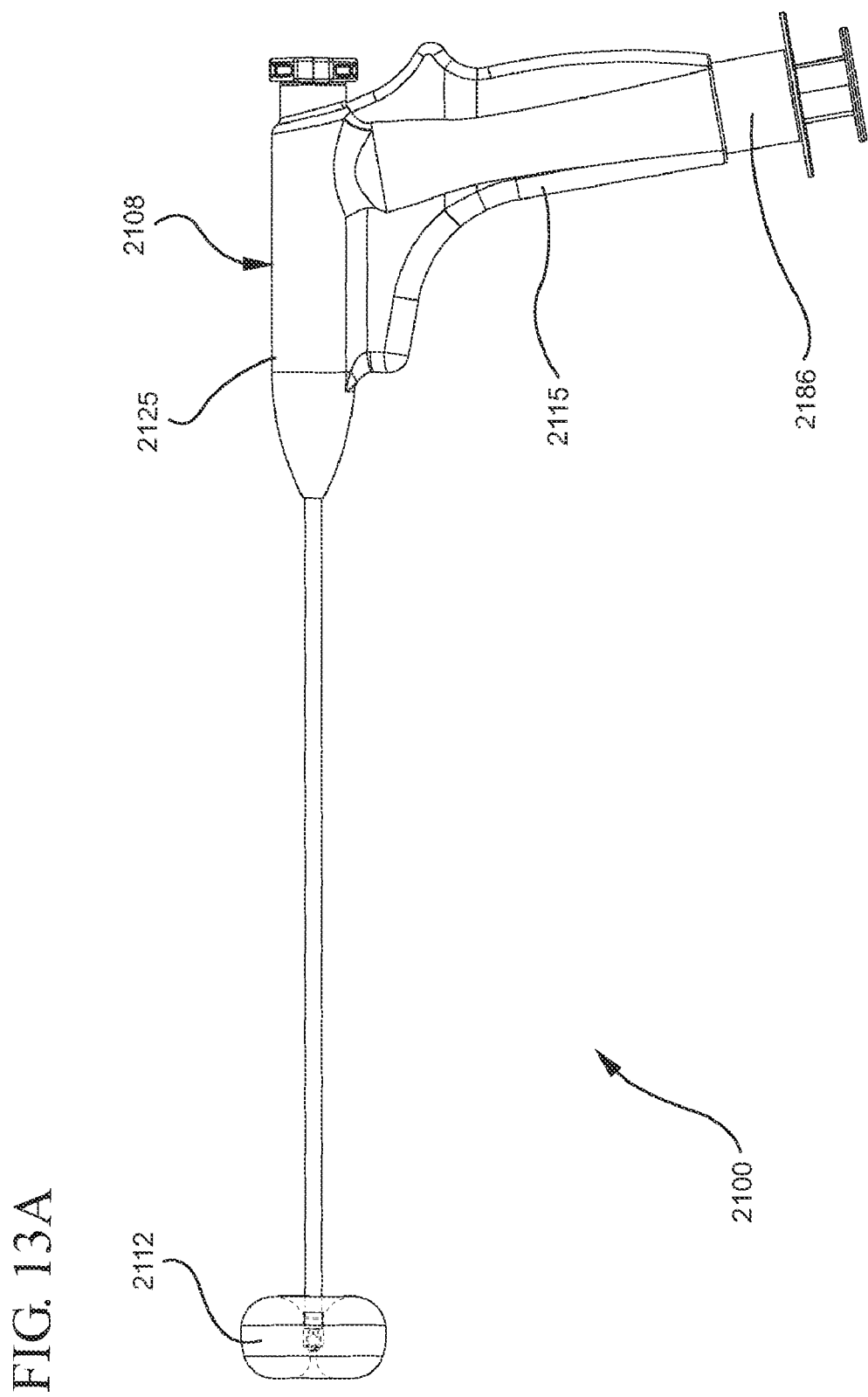

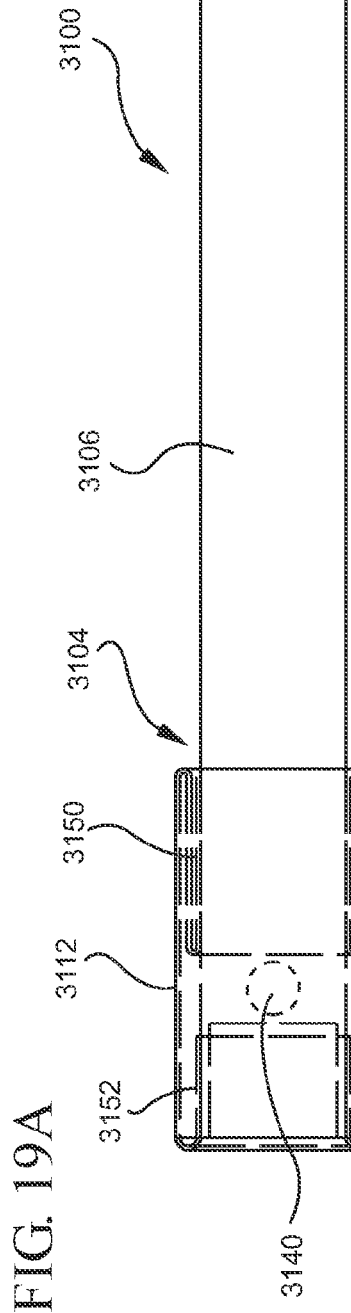
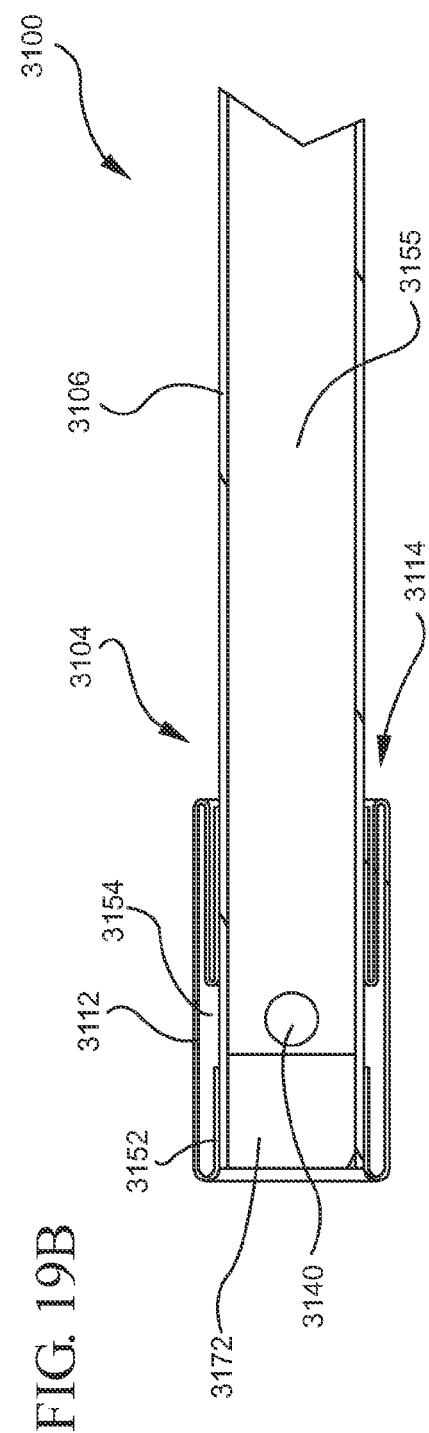

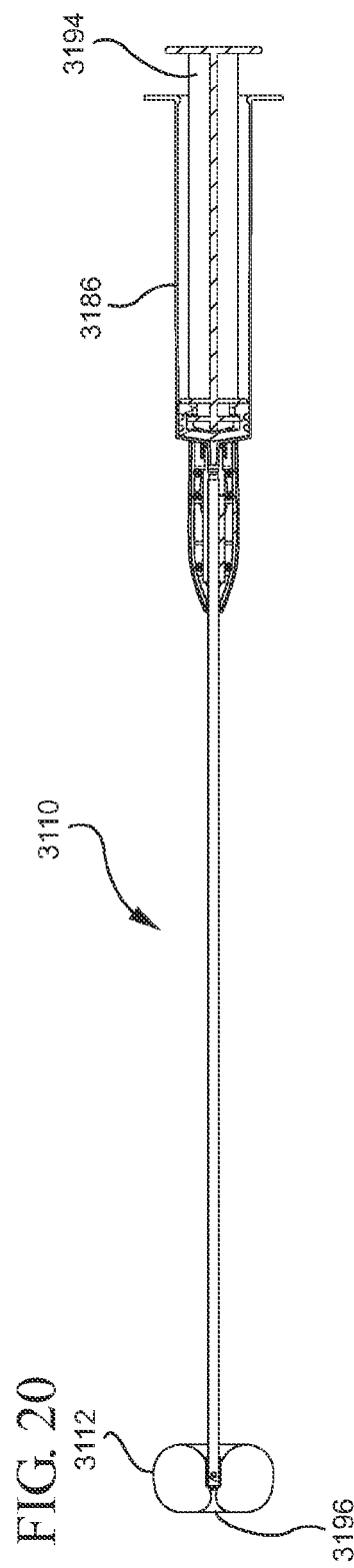
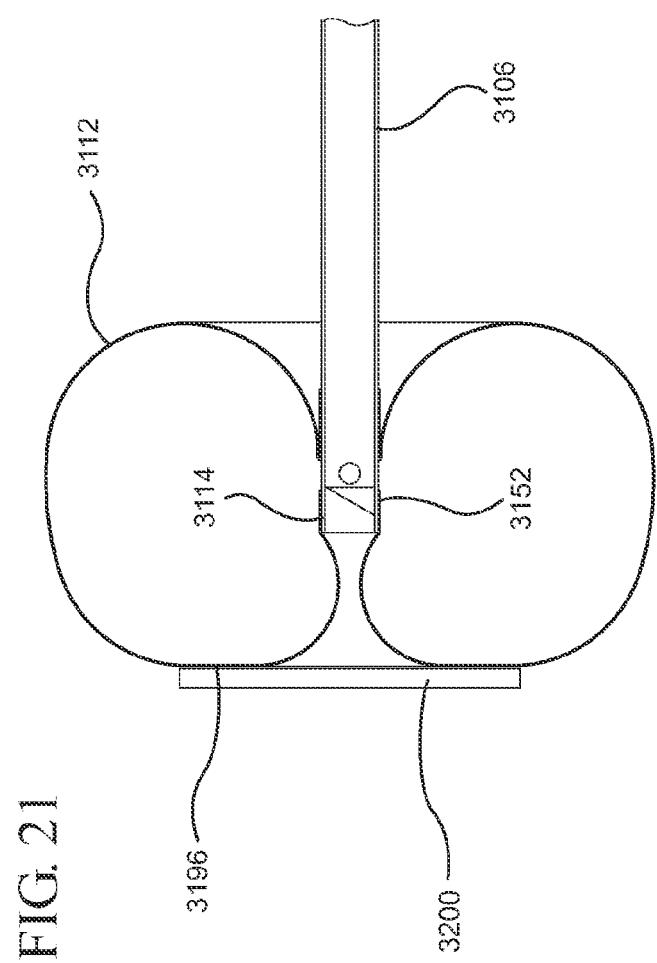

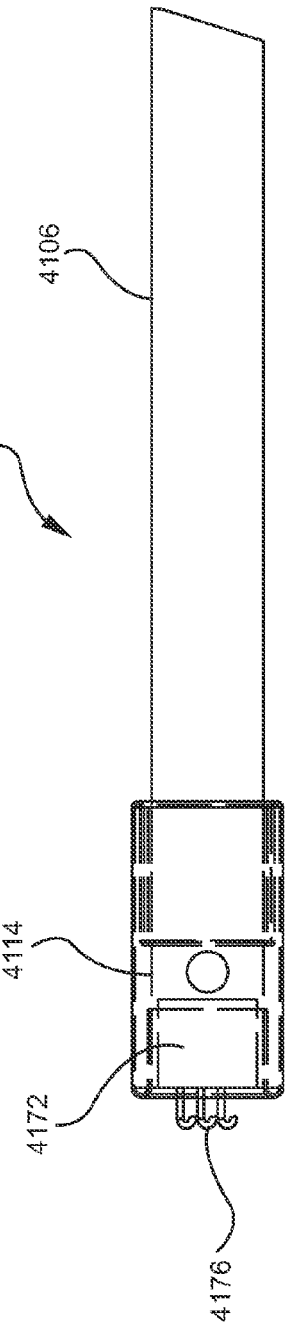
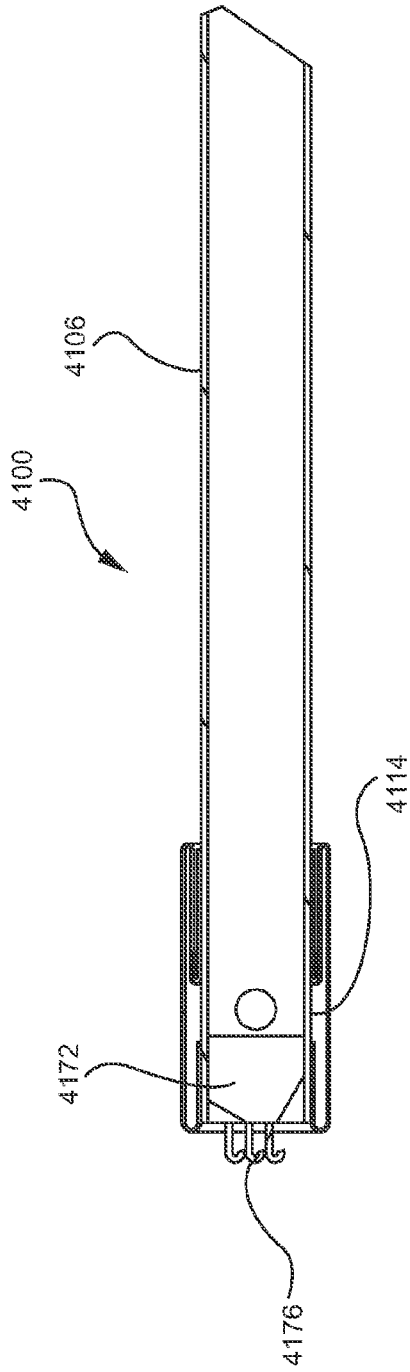

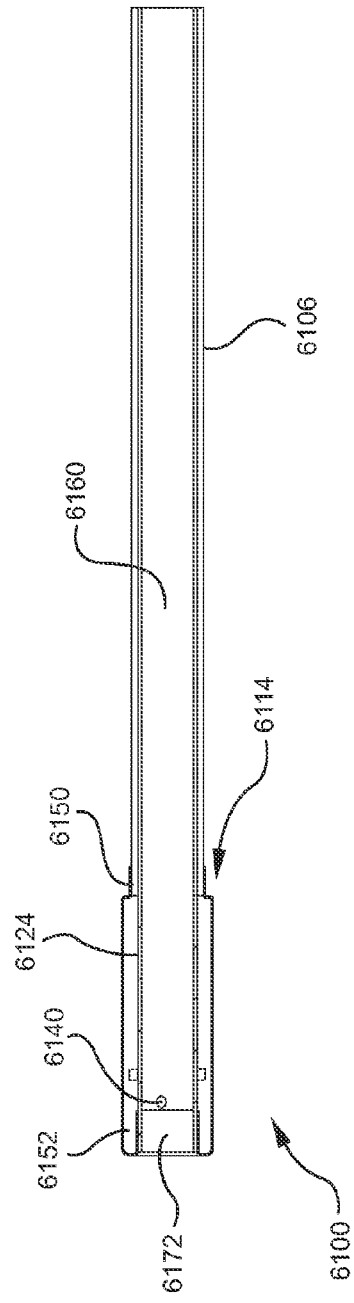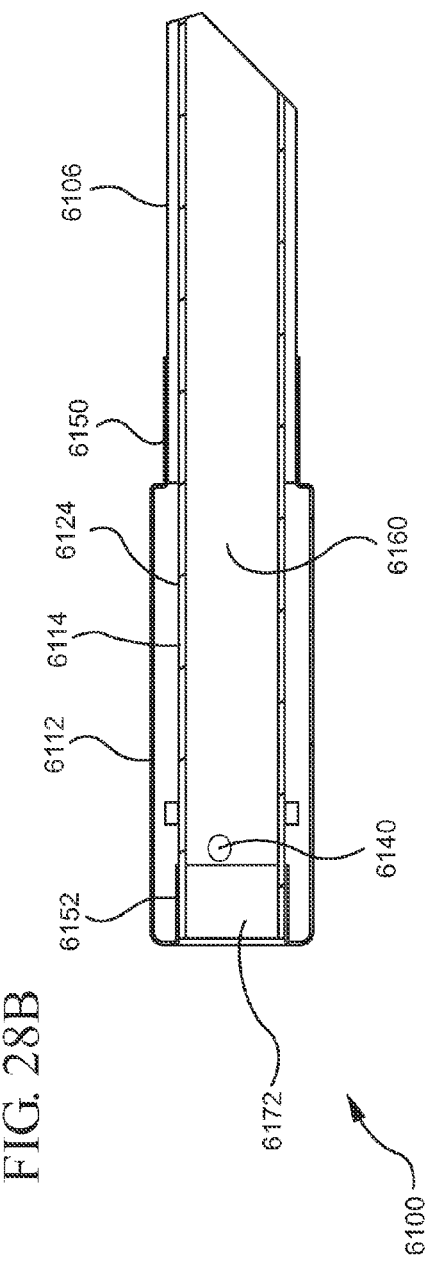

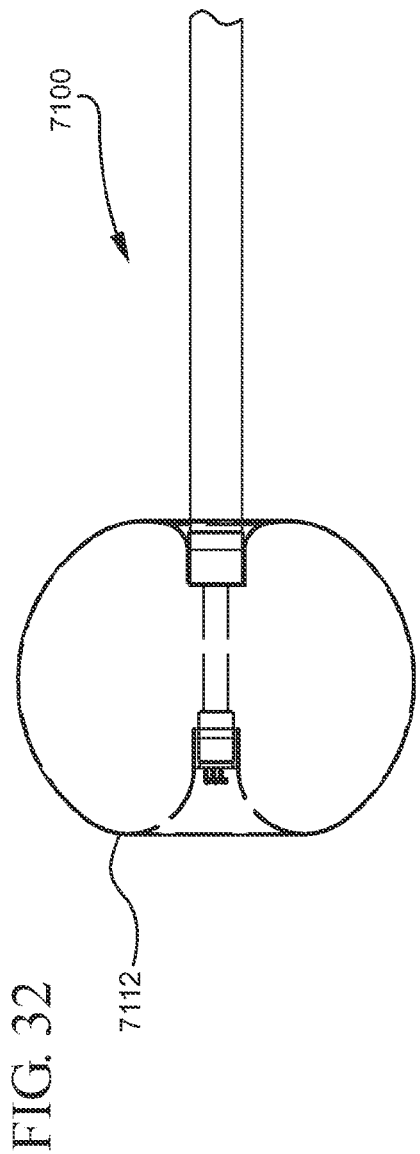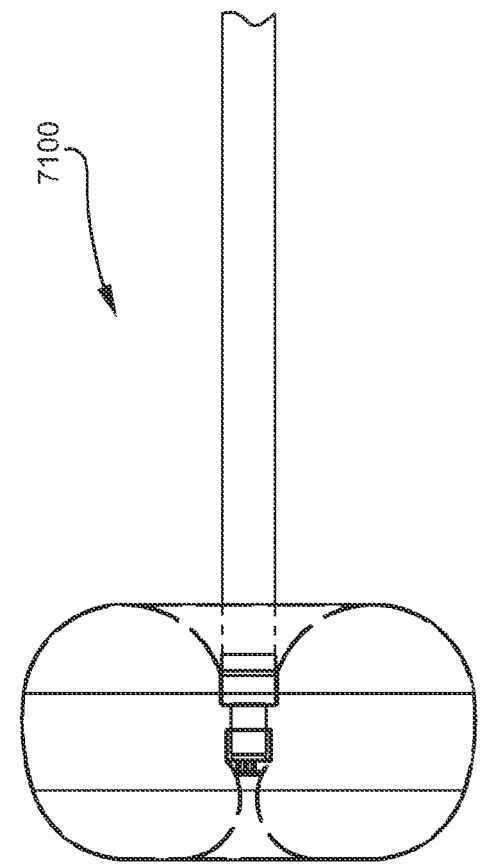
FIG. 32
FIG. 33

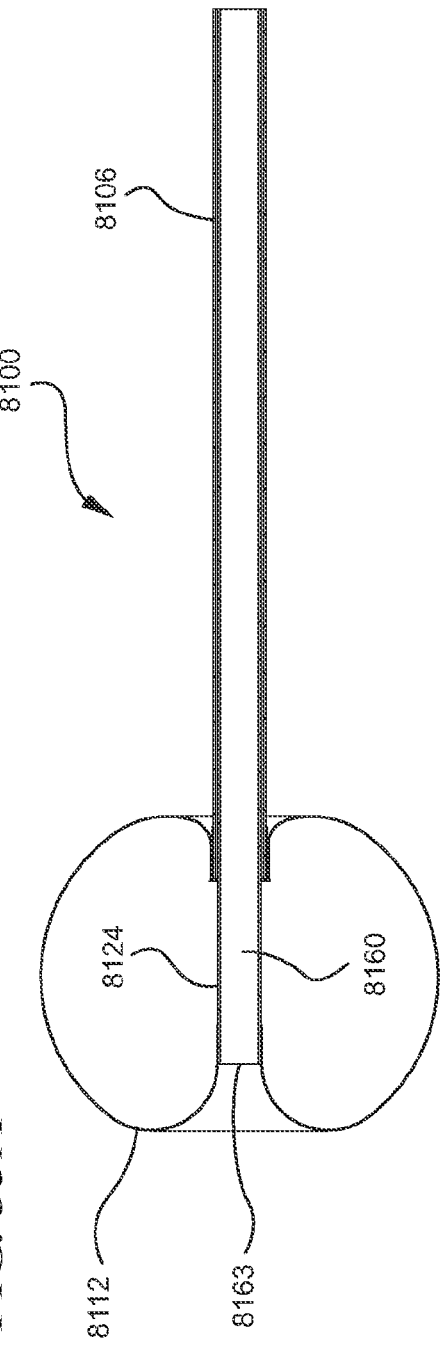
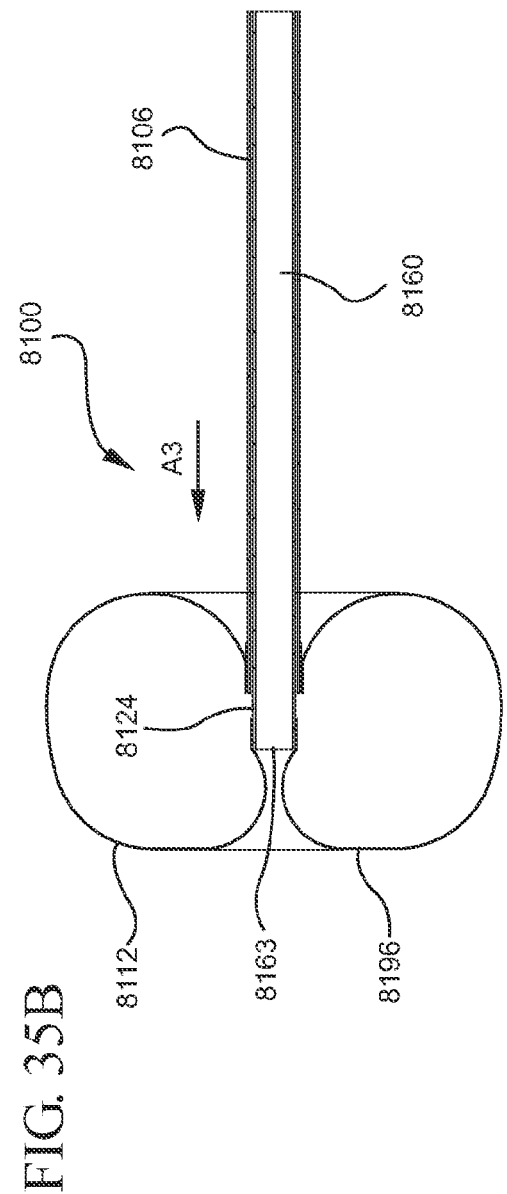
FIG. 35A
FIG. 35B

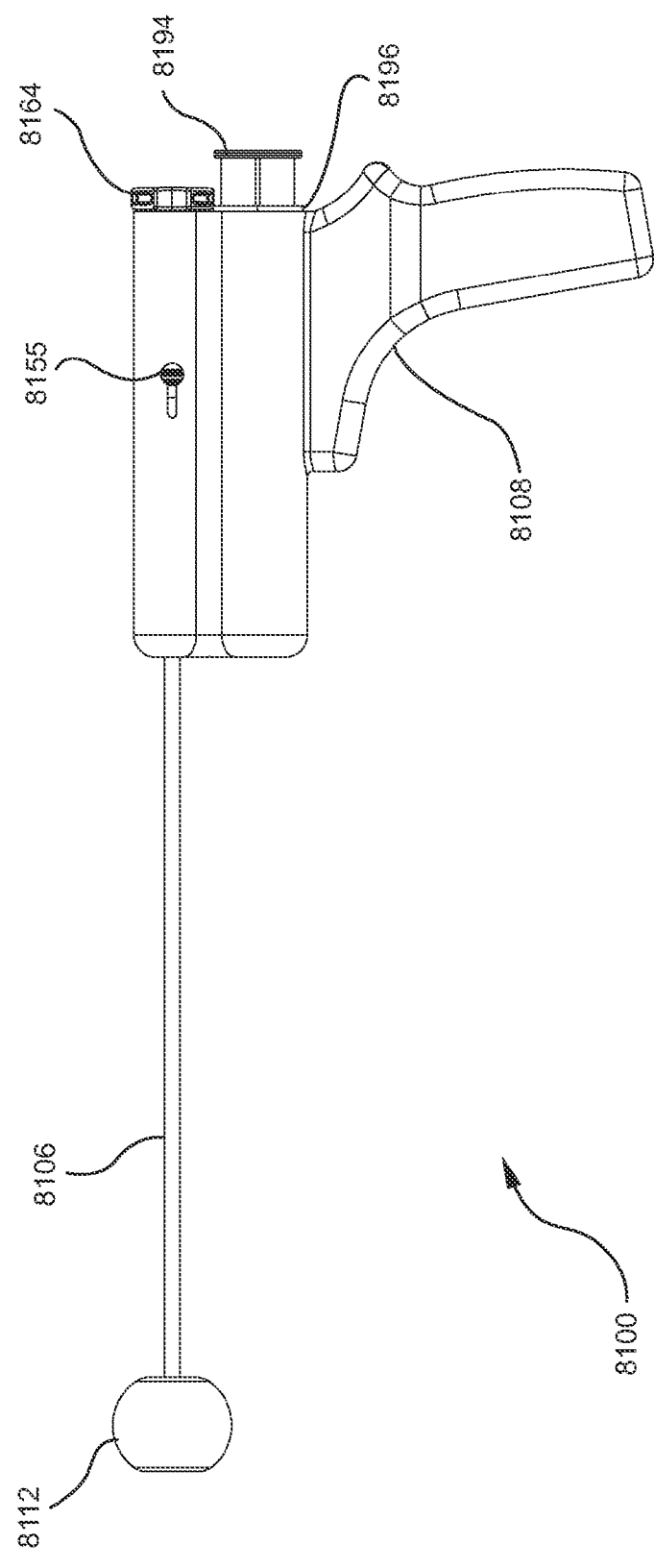

APPLICATOR INSTRUMENTS FOR CONTROLLING BLEEDING AT SURGICAL SITES AND METHODS THEREFOR

CROSS REFERENCE TO RELATED APPLICATIONS

The present application is related to commonly assigned U.S. patent application Ser. No. 12/049,849, entitled "APPLICATOR INSTRUMENTS FOR THE DELIVERY, DEPLOYMENT, AND TAMPONADE OF HEMOSTATS AND METHODS THEREFOR," filed Mar. 17, 2008, and U.S. patent application Ser. No. 12/049,869, entitled "APPLICATOR INSTRUMENTS HAVING PROTECTIVE CARRIERS FOR HEMOSTATS AND METHODS THEREFOR," filed Mar. 17, 2008, the disclosures of which are hereby incorporated by reference herein.

BACKGROUND OF THE INVENTION

1. Field of the Invention

The present application is generally related to controlling bleeding, and is more specifically related to systems, instruments, and methods used for the delivery, deployment, and tamponade of hemostats and flowable hemostats and sealants used for controlling bleeding at surgical sites.

2. Description of the Related Art

Medical textiles are used during surgical procedures to control bleeding, minimize blood loss, reduce post-surgical complications, and shorten the duration of surgery. Commonly used medical textiles include adhesion barriers, sponges, meshes, and hemostatic wound dressings that are applied to the surface of tissue. Hemostatic wound dressings include absorbable hemostats such as those sold by Ethicon, Inc. of Somerville, N.J. under the registered trademarks Surgicel®, Surgicel Nu-Knit®, and Surgicel® Fibrillar.

Traditionally, medical textiles have been delivered to endoscopic surgical sites using endoscopic grasping instruments such as clamps and forceps. It is also well-known to use applicator instruments for delivering medical textiles. For example, U.S. Pat. No. 3,857,395 discloses an inserter device having a pair of outwardly bendable arms that bilaterally spread an adhesion barrier within a vaginal cavity. The inserter device disclosed in the '395 patent, however, is not suitable for insertion through an endoscopic tube or trocar.

Commonly assigned U.S. Pat. No. 5,395,383 discloses an applicator instrument used for applying a sheet of surgical material (i.e. an adhesion barrier) through an endoscopic tube. The applicator instrument includes an expandable operating tip that is insertable into an endoscopic tube to enable a surgeon to apply the surgical material to tissue inside a body. In one embodiment, the applicator comprises a set of telescoping tubes including an outer delivery tube, an intermediate deployment tube, and an inner irrigation tube. The expandable operating tip is mounted at the distal end of the irrigation tube and is connected to the distal end of the deployment tube. The spreader tip is exposed at the distal end of the delivery tube by advancing the deployment tube and the irrigation tube relative to the delivery tube. The spreader tip is expanded by movement of the deployment tube relative to the irrigation tube to spread the sheet of surgical material over the tissue. A nozzle is provided at the distal end of the irrigation tube for applying a fluid, e.g., a saline solution, to the surgical material.

Commonly assigned U.S. Pat. No. 5,397,332 discloses an applicator for applying a sheet of surgical material, e.g., a surgical mesh, to internal body tissue. The applicator includes a delivery tube, a deployment tube slidably received within the delivery tube, and a shaft or irrigation tube slidably received within the deployment tube. An expandable spreader tip is connected between the distal ends of the shaft and the deployment tube. The spreader tip is collapsed and inserted in the delivery tube with the surgical mesh. The applicator is inserted through a trocar tube into a body cavity and the spreader tip is exposed by retracting the delivery tube relative to the deployment tube and shaft. The applicator has a first actuator for urging the spreader tip and surgical mesh into engagement with the tissue as the deployment tube is retracted, and a second actuator for advancing the deployment tube relative to the shaft to expand the spreader tip to apply the surgical mesh to the tissue. The spreader tip includes a plurality of flexible strips each having opposite ends pivotally connected to the distal ends of the shaft and the deployment tube. The applicator includes a return spring to bias the deployment tube proximally relative to the shaft to normally maintain the spreader tip in a collapsed configuration.

In spite of the above advances, there remains a need for improved instruments and methods for the delivery, accurate placement, deployment, and tamponade of medical textiles such as adhesion barriers, wound dressings, and topically applied hemostats. More particularly, In addition, there remains a need for instruments and methods for introducing flowable hemostats and sealants to surgical sites for controlling bleeding.

SUMMARY OF THE INVENTION

In one embodiment, the present invention discloses an applicator instrument used for the endoscopic delivery of medical textiles such as meshes, hemostats, adhesion prevention barriers, and sponges, and flowable materials such as flowable hemostats and sealants. In one embodiment, the applicator instrument is preferably adapted for the endoscopic delivery, deployment and tamponade of hemostats such as topically applied hemostats (TAH), and flowable hemostats. In the present application, the terms "hemostat", "topically applied hemostat", and "flowable hemostat" are used most frequently to describe the various medical components that may be delivered and deployed by the present invention. However, the present application contemplates that these terms should be read broadly to cover all of the medical textiles and flowable hemostats and sealants described, as well as other materials conventionally used to control bleeding.

In one embodiment, an instrument for controlling bleeding includes an outer shaft having a proximal end, a distal end, and a central lumen extending between the proximal and distal ends, and an inner shaft disposed within the central lumen of the outer shaft, the inner shaft having a proximal end, a distal end that extends beyond the distal end of the outer shaft, and a central lumen extending between the proximal and distal ends thereof. The instrument desirably includes an inflatable balloon having a proximal end secured to the outer shaft and a distal end that is inverted and secured to the inner shaft, and a first actuator in communication with the inflatable balloon for selectively inflating the balloon. In one embodiment, the first actuator includes a syringe having a barrel and a plunger, and the plunger is depressible for introducing the fluid into the balloon. The instrument preferably has a first conduit extending between the inner and outer shafts and toward the distal ends of the inner and outer shafts. The first conduit is desirably in communication with the inflatable balloon at one end, and the first actuator at an opposite end of the first conduit.

In one embodiment, the instrument includes a hub connector secured to the proximal end of the outer shaft. The hub connector desirably has a first connection port for coupling the first actuator with the first conduit. The hub connector may also have a second connection port that is aligned with the central lumen of the inner shaft. A stylet may be inserted into the second connection port and the central lumen of the inner shaft. The stylet may have proximal and distal ends, a handle at the proximal end thereof, and hook-like barbs at the distal end thereof. The stylet is preferably insertable into the second connection port and through the central lumen of the inner shaft for positioning the hook-like barbs at the distal end of the inner shaft. The stylet may also have threads adjacent the handle thereof for threadably securing the stylet to the hub connector.

In one embodiment, the instrument may include a second actuator adapted to hold a flowable material, such as a flowable hemostat material or a sealant. The second actuator may be coupled with the second connection port of the hub connector for dispensing the flowable material through the central lumen of the inner shaft. In one embodiment, the second actuator includes a barrel for holding the flowable material, a discharge opening alignable with the central lumen of the inner shaft, and a plunger that is depressible for dispensing the flowable material into the central lumen of the inner shaft. The second actuator may include a connector such as a Luer connector for securing the tip of the second actuator to the second connection port of the hub connector. In one embodiment, the second actuator may include a sealant delivery system having a catheter that extends through the central lumen of the inner shaft for delivering the sealant from the distal end of the instrument. One preferred sealant delivery system may include the Evicel™ sealant delivery system sold by Johnson & Johnson Wound Management of New Brunswick, N.J. A preferred sealant delivery system may have a catheter tip having a length of up to 35 cm or more in length, whereby the catheter tip is passed through the central lumen of the inner shaft to deliver the sealant from the distal end of the instrument.

In one embodiment, the instrument may include a shaft actuator in communication with at least one of the inner and outer shafts for selectively moving the distal ends of the shafts relative to one another for changing the shape of the inflated balloon. In one preferred embodiment, the shaft actuator is adapted to selectively move the distal end of the outer shaft in a distal direction relative to the distal end of the inner shaft for changing the shape of the inflatable balloon secured to the outer and inner shafts. When desired, the outer shaft may be moved proximally back to its original configuration for transforming the shape of the inflated balloon back to the original spherical shape.

In one embodiment, an instrument for controlling bleeding includes a shaft having a proximal end and a distal end, an inflatable balloon having a proximal end secured to the shaft and a distal end that is inverted and that is secured to the distal end of the shaft. The inverted distal end of the inflatable balloon is desirably connected to a distal-most end of the shaft. The instrument also preferably includes an actuator for selectively inflating the inflatable balloon. The actuator is desirably coupled with a connection port located at the proximal end of the shaft. The instrument may include a valve in communication with the inflatable balloon for selectively deflating the balloon. In one embodiment, the instrument includes barbs projecting from the distal end of the shaft. The shaft desirably has a longitudinal axis extending between the proximal and distal ends thereof, and the barbs project along the longitudinal axis.

In one embodiment, an instrument for controlling bleeding includes an inner shaft having a proximal end and a distal end, and an outer shaft having a proximal end and a distal end, the outer shaft surrounding the inner shaft. The instrument includes a first lumen extending between the inner and outer shafts, and a second lumen extending though the inner shaft to a distal opening at the distal end of the inner shaft. The instrument also desirably includes an inflatable balloon secured to the distal end of the instrument, the inflatable balloon being in communication with the first lumen. The balloon preferably has a proximal end secured to the outer shaft and a distal end surrounding the distal opening of the second lumen and being secured to the inner shaft. In one embodiment, the distal end of the balloon is inverted and the inverted distal end of the balloon is secured to the distal end of the inner shaft.

The instrument may also include a first actuator, such as an inflation syringe, in communication with the first lumen for selectively inflating the balloon, and a second actuator, such as a syringe filled with a flowable material, in communication with the second lumen for introducing the flowable material into the second lumen and for discharging the flowable material from the distal opening at the distal end of the inner shaft. The flowable material may be a sealant and/or a flowable hemostat material.

The instrument may include a hub connector secured to the proximal end of the outer shaft. The hub connector desirably has a first connection port in communication with the first lumen. The hub connector may also have a second connection port in communication with the second lumen. The first actuator is preferably coupled with the first connection port and the second actuator is preferably coupled with the second connection port. The instrument may also include a third actuator coupled with the outer shaft for moving the distal end of the outer shaft distally relative to the distal end of the inner shaft for selectively changing the shape of the inflatable balloon.

In one embodiment, the applicator instrument includes a balloon that is used to endoscopically deploy and tamponade a hemostat. The balloon is desirably attached at each end to one of two pieces of concentric tubing such that one balloon end is movable and the shape of the inflated balloon is changeable from a rounder shape to a flatter shape, such as from a spherical shape to a toroidal shape. In one embodiment, the distal end of the balloon is inverted and the inverted surface is attached to the outer surface of one of the concentric tubes so that when the balloon is inflated the attachment of the distal end of the balloon to the distal end of the device is located inside the inflated balloon. This configuration provides a flatter surface area of the balloon for applying an evenly distributed tamponade pressure to the hemostat.

In one embodiment, barbed hooks may be incorporated at the distal end of the applicator instrument, and the hooks or barbs may be used to attach the hemostat to the distal end of the instrument prior to delivering the hemostat to a surgical site.

In one embodiment, the outer and inner shafts may be moved relative to one another for changing the shape of the inflated balloon. In one embodiment, the balloon has a rounder or more spherical shape when the outer and inner shafts are in a first position and a flatter or more toroidal shape when the outer and inner shafts are in a second position. In one embodiment, the balloon assumes a toroidal shape, and the flattened leading face of the balloon is used to apply tamponade pressure to one or more hemostats.

The applicator instrument may include a hemostat disposed at the distal end of the inner shaft. The hemostat may be a medical textile, a topically applied adhesive, a hemostat patch folded over the distal end of the inner shaft, a flowable hemostat, or any conventional medical device used to control bleeding. The inner shaft may have barbs or hooks provided at the distal end thereof for attaching a hemostat such as a topically applied hemostat or a hemostat patch to the inner shaft.

In one embodiment, the instrument includes a first actuator for selectively inflating the balloon, and another actuator coupled with at least one of the outer and inner shafts for selectively moving the distal ends of the outer and inner shafts relative to one another for changing the shape of an inflated balloon. In one embodiment, the outer and inner shafts desirably have tubular shapes, and at least one of the outer and inner shafts has an opening for introducing fluid, such as air, into the balloon.

In one embodiment of the present invention, a method for controlling bleeding includes providing an applicator instrument, and attaching a hemostat to the distal end of the instrument. The applicator instrument with the hemostat attached thereto may be advanced to a surgical site such as by passing the tip of the applicator instrument through an endoscope or trocar. After the hemostat has been delivered to the surgical site, a balloon at the distal end of the applicator instrument may be inflated by engaging an actuator such as a syringe plunger. As the balloon is inflated, the expanding balloon deploys the hemostat by unfurling the hemostat and advancing the edges of the hemostat toward the tissue surface at the surgical site. When the balloon is inflated, it normally assumes a substantially spherical shape. The shape of the balloon may be changed, however, by engaging another actuator such as a deformation slider that changes the shape of the balloon into a substantially toroidal shape. In the toroidal shape, a leading face of the balloon now assumes a substantially flatter surface that provides more surface area for engaging the delivered and deployed hemostat. In one embodiment, tamponade pressure is applied by the balloon to the hemostat for approximately 1-5 minutes, and more preferably 2-3 minutes.

In one embodiment, the inflatable balloon is transparent so that the deployment and tamponade of the hemostat may be observed through the balloon. If bleeding has not been controlled after a predetermined period of time, this condition may be observed through the transparent balloon. In response to this condition, tamponade pressure may be applied for longer time periods until the bleeding has stopped or is under control.

In one embodiment, after the bleeding is under control, the deformation slider may be retracted for returning the intermediate and inner shafts to the normal spacing configuration. As the deformation slider is retracted, the balloon is preferably transformed from a toroidal shape back to the original spherical shape. The inflated balloon may be deflated by retracting the plunger of the balloon inflation actuator. A spring provided inside the syringe may return the plunger to the retracted position. After the balloon is deflated, the tip of the applicator instrument may be retracted from the surgical site and removed from the endoscope or trocar. After the applicator instrument is withdrawn from the surgical site, the hemostat preferably remains in place atop the tissue at the surgical site for controlling bleeding.

Although the present invention is not limited by any particular theory of operation, it is believed that the present invention provides numerous benefits over prior art instruments, systems, and methods. One advantage of the present invention is that the shape of an inflated balloon may be altered so as to maximize the surface area available for applying tamponade pressure to a deployed hemostat. The increased surface area and the flatter surface area allows for more efficient and enhanced tamponade pressure to be applied to the hemostats. This feature is particularly useful for applying pressure to topically applied hemostats.

In addition, in one embodiment, the present invention discloses an applicator instrument having a transparent balloon that enables medical personnel to observe a surgical site as tamponade pressure is applied to hemostats using the balloon.

In one embodiment, the outer and inner shafts of the applicator instrument are not moveable, and the balloon does not change shape. After the balloon is inflated to a desired shape, either spherical or toroidal as described earlier, the fluid used to inflate the balloon is communicated between the outer diameter (OD) of the inner shaft and the inner diameter (ID) of the outer shaft. The lumen of the inner shaft may be in communication through the proximal handle of the device. The proximal end of the inner shaft may have a syringe connector means, such as a Luer connector, attached thereto. The Luer connector may be used to attach a syringe that dispenses a fluid (e.g. SURGIFLO) through the lumen of the inner shaft into a surgical cavity, with the balloon in either an inflated or deflated state. The lumen of the inner shaft may also be used to guide, support and allow passage of other fluid delivery systems, such as the EVICEL Fibrin Sealant having a 45 cm catheter delivery device. Moreover, a Luer cap or plug may be attached to the Luer connector to prevent surgical cavity insufflation gases from undesirably exiting through the instrument. In one embodiment, a stylet may be passed through and attached to the Luer connector. The stylet preferably has a length such that the tip of the stylet is in close proximity to the distal end of the lumen of the inner shaft. The distal tip of the stylet may have barbs, for the purpose of engaging and picking up and a textile based topically applied hemostat (TAH) as described herein.

In one embodiment, the applicator instrument may have only a single shaft, and the balloon may not change shape after it is inflated. In one embodiment, both the distal and proximal ends of the inflatable balloon are attached to the outer diameter (OD) of a single shaft. The proximal end of the shaft may have a hub connector secured thereto. A syringe having a flowable hemostat may be coupled to the hub connector for dispensing a flowable hemostat through a central lumen of the shaft.

In one embodiment, a user may physically hold the balloon inflation syringe plunger in the depressed position in order to keep the balloon inflated. The user may pull back on the syringe plunger to deflate or aspirate the balloon, or the syringe may have an axially aligned internal spring that is adapted to return the plunger to the extended position for automatically aspirating the balloon. In one embodiment, the spring may be axially aligned and be located between the proximal surface of the barrel's flange and the distal surface of the plunger's proximal flange.

In one embodiment, the syringe includes a locking ring that engages the outer surface of a cylindrical plunger to lock the plunger in place. When it is desired to move the plunger, the locking ring may be pushed toward the leading end of the syringe to release the plunger for movement. This embodiment may incorporate one or more of the features or method steps disclosed in commonly assigned U.S. patent application Ser. No. 12/049,849, entitled "APPLICATOR INSTRUMENTS FOR THE DELIVERY, DEPLOYMENT, AND TAMPONADE OF HEMOSTATS AND METHODS THEREFOR, filed Mar. 17, 2008, the disclosure of which is hereby incorporated by reference herein.

In one embodiment, the syringe plunger is adapted to be locked at discrete axial intervals. In this embodiment, a series of slots are cut into the plunger's cruciform cross section, and a distally mounted disk-like cap is fixed to the flange end of the barrel. The disk-like cap has a cruciform slot cut out to allow passage of the plunger's cruciform cross section. By rotating the plunger about (nominally) 45 degrees along its long axis when a set of slots in the plunger line up with the cruciform slot in the disk, the plunger cannot be moved axially due to either proximal or distal surfaces of the plunger's slots making contact with the portions of the disk adjacent to the cruciform slot. To unlock the plunger for balloon aspiration, the plunger is rotated so that the cruciform cross-section part of the plunger is in line with the cruciform slot in the disk.

In one embodiment, a valve system is placed between the syringe and the balloon inflation port. The valve system may include a two port stopcock; a three port stopcock, one port venting to the outside when not shut off; a Luer-activated valve (normally closed, opens when a syringe male Luer fitting is introduced into the valve); a check-valve (e.g. a duckbill or disk valve in a housing); or a system including a check valve that is bypassed by a normally closed trumpet valve, a two port stopcock, or a three port stopcock. The valve system may be removable from the handle, or it may be integrated into the handle. The valve system may also be mounted to a short piece of extension tubing either between the valve system and the handle or between the valve system and the syringe. One advantage of these systems is that the syringe may be inflated to any volume, not just discrete intervals. Another advantage of the systems having the three port stopcock configurations is that the balloon inflation path may be vented to the outside without removing the inflation syringe, which may be operationally advantageous if fluid such as air needs to be added or removed from the normally sealed balloon inflation path.

These and other preferred embodiments of the present invention will be described in more detail below.

BRIEF DESCRIPTION OF THE DRAWING

FIGS. 4A-4C show a stylet used with the instrument of FIG. 1.

FIGS. 8A-8B show the instrument of FIGS. 7A-7B after the balloon has been inflated.

FIGS. 10A and 10B show perspective and phantom views, respectively, of a second actuator for an instrument for controlling bleeding, in accordance with one embodiment of the invention.

FIGS. 12A and 12B show front elevational and cross-sectional views, respectively, of an instrument for controlling bleeding with an inflatable balloon at a distal end of the instrument being in an inflated state.

FIGS. 13A and 13B show front elevational and cross-sectional views, respectively, of an instrument for controlling bleeding, in accordance with one embodiment of the present invention.

FIGS. 19A and 19B show respective front elevational and cross-sectional views of the inflatable balloon at the distal end of the instrument shown in FIG. 15.

FIG. 20 shows a cross-sectional view of the instrument of FIG. 17A with the inflatable balloon in an inflated state.

FIG. 21 shows a cross-sectional view of the distal end of the instrument shown in FIG. 20.

FIGS. 22A and 22B show respective front elevational and cross-sectional views of a distal end of an instrument having an inflatable balloon for controlling bleeding, in accordance with one embodiment of the invention.

FIGS. 28A and 28B show cross-sectional views of a distal end of an instrument for controlling bleeding including an inflatable balloon, in accordance with one embodiment of the invention.

FIG. 32 shows the instrument of FIGS. 31A and 31B after the inflatable balloon at the distal end has been inflated.

FIG. 33 shows the instrument of FIG. 32 after the shape of the inflated balloon has been altered.

FIG. 35A shows the distal end of the instrument shown in FIG. 34 with the outer and inner shafts in a first position relative to one another.

FIG. 35B shows the distal end of the instrument shown in FIG. 34 with the outer and inner shafts in a second position relative to one another.

FIGS. 36A and 36B show front elevational views of an instrument for controlling bleeding, in accordance with one embodiment of the present invention.

DETAILED DESCRIPTION

Figure 1:
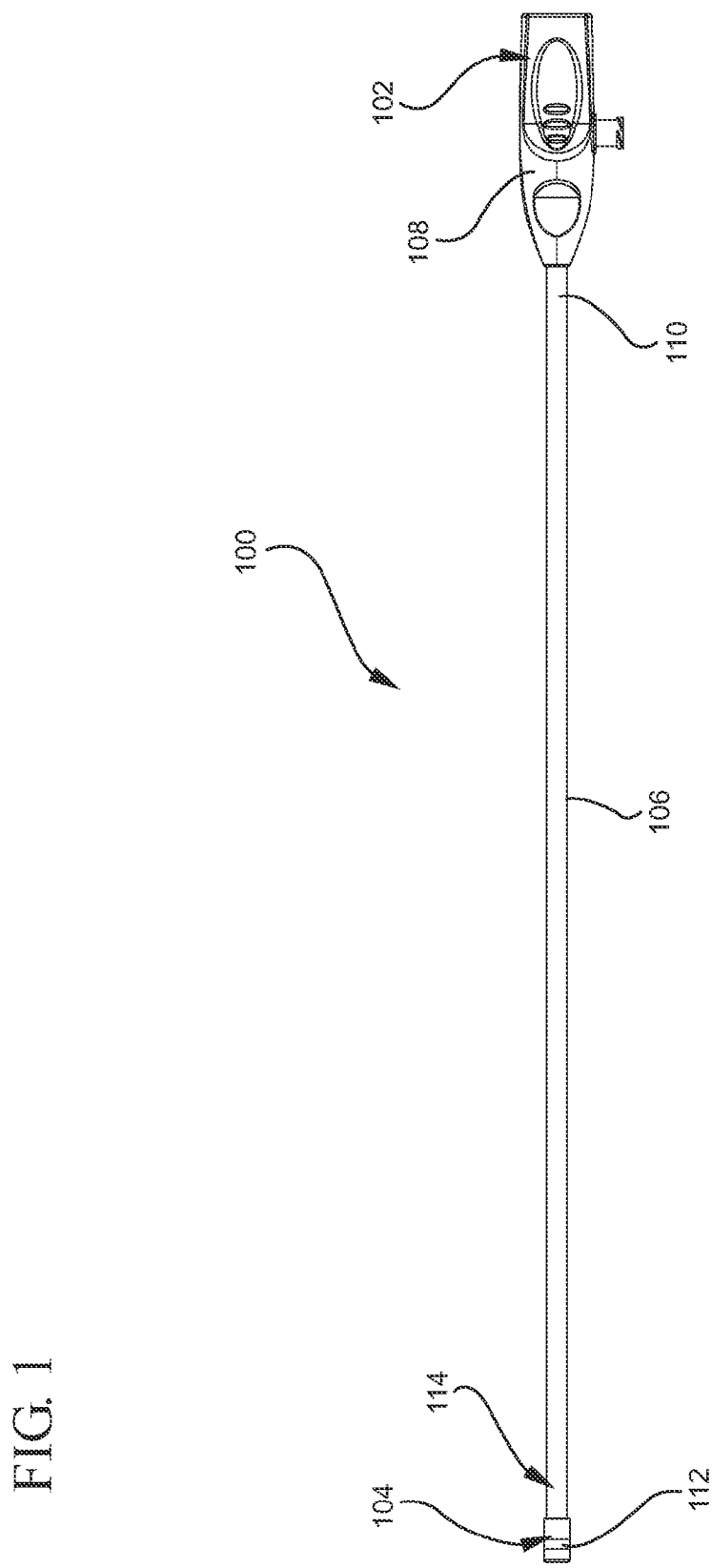
FIG. 1 shows a front elevational view of an instrument for controlling bleeding including a proximal end having a hub connector and a distal end having an inflatable balloon, in accordance with one embodiment of the invention.

The invention disclosed herein is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways.

The headings used herein are for organizational purposes only and are not meant to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

Referring to FIG. 1, in one embodiment, an instrument 100 for controlling bleeding has a proximal end 102 and a distal end 104. The instrument 100 includes an outer shaft 106 that extends between the proximal and distal ends 102 and 104, a hub connector 108 coupled with a proximal end 110 of the outer shaft 106, and an inflatable balloon 112 connected with a distal end 114 of the outer shaft 106. In one embodiment, the length of the outer shaft 106 (the "working length") is about 10-15 inches, and more preferably about 13 inches (33 cm).

Figure 2:
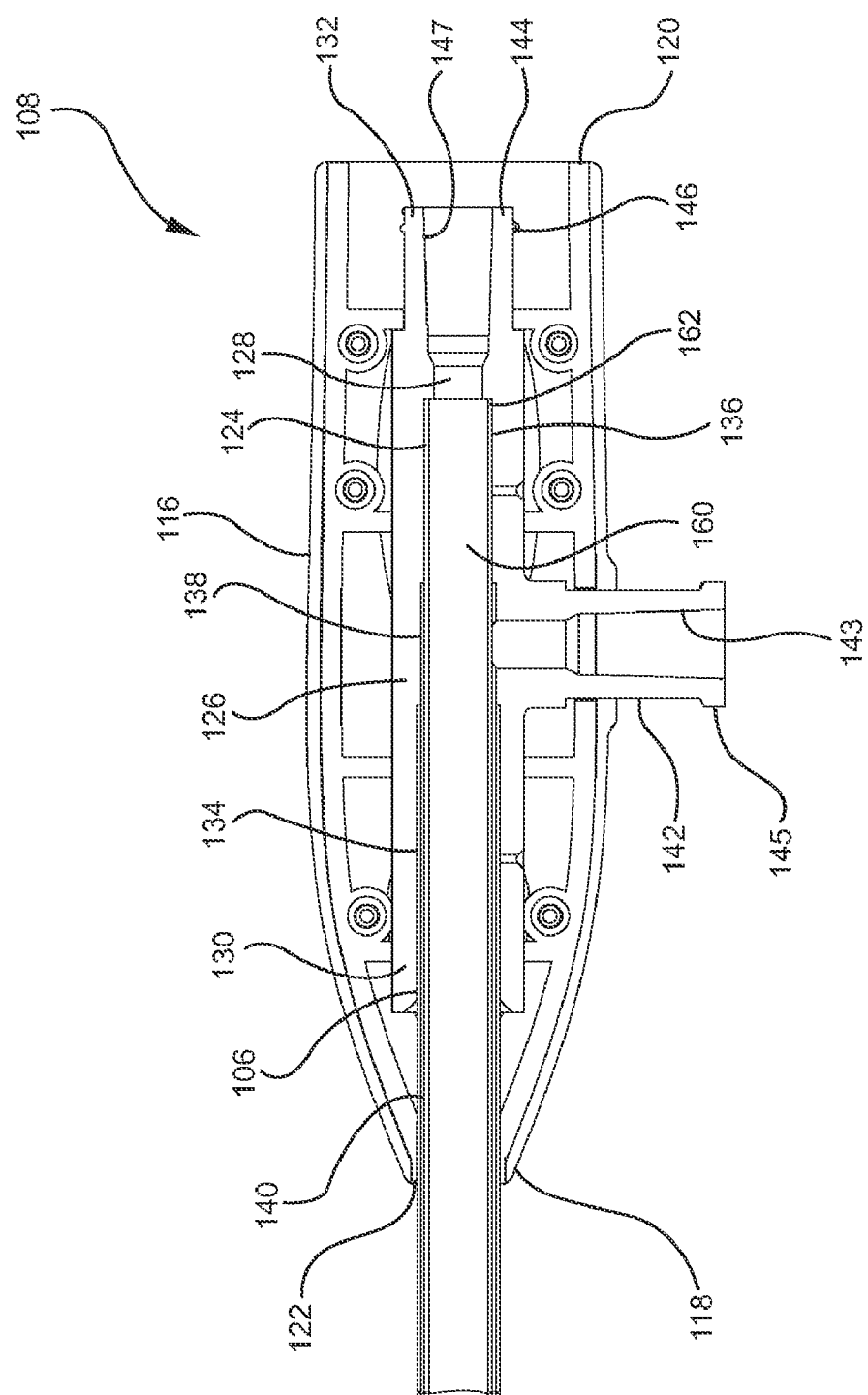
FIG. 2 shows a cross-sectional view of the hub connector shown in FIG. 1.

Referring to FIG. 2, in one embodiment, the hub connector 108 includes a housing 116 having a leading end 118 and a trailing end 120. The leading end 118 of the housing 116 includes a shaft opening 122 that is adapted to receive the outer shaft 106 and an inner shaft 124. The outer shaft 106 desirably has a central lumen that extends between the proximal and distal ends thereof, and the inner shaft 124 is received within the central lumen of the outer shaft. In turn, the inner shaft 124 has a central lumen that extends between the proximal and distal ends thereof. The hub connector 108 includes a shaft support tube 126 having a central bore 128 that extends between a leading end 130 and a trailing end 132 of the shaft support tube. The central bore 128 has a leading section 134 having a first inner diameter that closely matches the outer diameter of the outer shaft 106, and a trailing section 136 having a second inner diameter that closely matches the outer diameter of the inner shaft 124. In one embodiment, the leading section 134 of the central bore 128 has a larger diameter than the trailing section 136 of the central bore. The central bore 128 also desirably includes an intermediate section 138 that lies between the leading section 134 and the trailing section 136. The intermediate section 138 of the central bore 128 is preferably in communication with a first conduit 140 that extends in a distal direction between the inner shaft 124 and the outer shaft 106.

The hub connector 108 desirably includes a first connection port 142 that is in communication with the intermediate section 138 of the central bore 128. The first connection port 142 desirably has a tapered opening 143. A first actuator (not shown), such as a syringe, may be coupled with the first connection port 138 for forcing a fluid such as air through the intermediate section 138 of the central bore and into the first conduit 140. The first actuator may have a tip having a taper that matches the taper of the tapered opening 143. As will be described in more detail below, the fluid forced through the first conduit may be used for inflating the inflatable balloon 112 located at the distal end of the instrument. The second connection port preferably has threads 145 for connecting the first actuator to the first connection port.

The hub connector 108 also desirably includes a second connection port 144 such as a connection port including a female threaded Luer connection at the trailing end 132 of the shaft support tube 126. Threads 146 are provided around the trailing end 132 of the shaft support tube 126 to provide a threaded coupling for an opposing element, as will be described in more detail below. The second connection port 144 preferably has a tapered opening 147 that is adapted to receive the leading end of the second actuator. The leading end of the second actuator may have a taper that matches the taper of the tapered opening 147.

Figure 3:
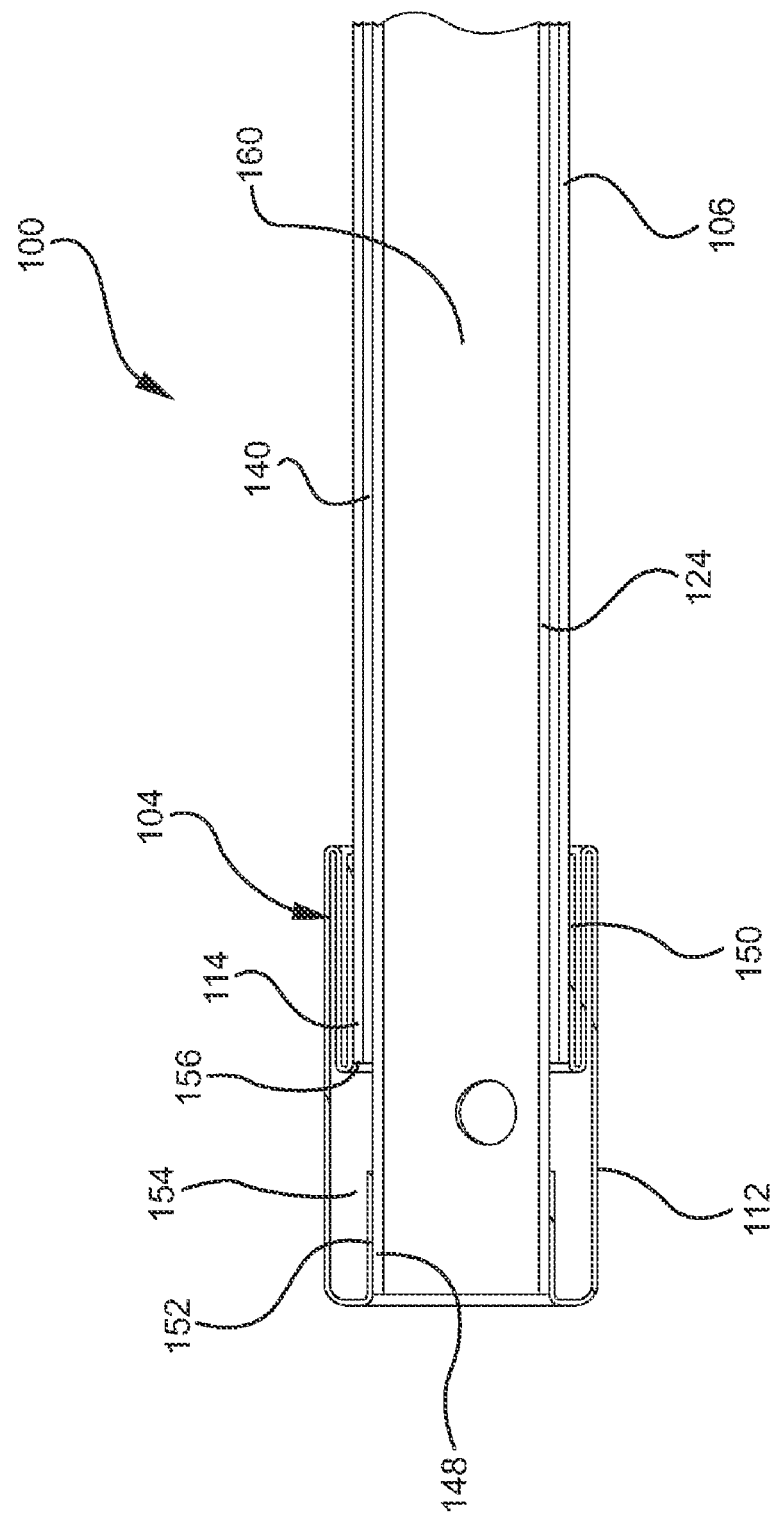
FIG. 3 shows a cross-sectional view of the inflatable balloon at the distal end of the instrument shown in FIG. 1.

Referring to FIG. 3, the distal end 104 of the instrument 100 includes the outer shaft 106, the inner shaft 124, and the first conduit 140 that extends between the outer and inner shafts. A distal end 148 of the inner shaft preferably extends beyond the distal end 114 of the outer shaft 106. The instrument includes the inflatable balloon 112 having a proximal end 150 secured to the distal end 114 of the outer shaft 106, and a distal end 152 that is secured to the distal end 148 of the inner shaft 124. The proximal end 150 of the inflatable balloon 112 is preferably secured to an outer surface of the outer shaft 106. The distal end 152 of the inflatable balloon 112 is preferably inverted, and the inverted distal end is preferably secured to an outer surface of the inner shaft 124 at the distal end of the inner shaft 124. The above-described structure desirably forms an air-tight compartment 154 inside the inflatable balloon 112. The distal end 156 of the first conduit 140 is preferably in communication with the air-tight compartment 154. Fluid such as air may be directed through the first conduit 140 and into the compartment 154 for inflating the balloon 112. When it is desirable to deflate the balloon 112, the fluid may be removed from the balloon through the first conduit 140. In the particular embodiment shown in FIGS. 1-3, the outer and inner shafts 106, 124 do not move relative to one another. In other embodiments, however, the outer and inner shafts may be selectively moved relative to one another for changing the shape of an inflated balloon. In one embodiment, the balloon initially has a spherical shape, and the outer and inner shafts are moved relative to one another to change the balloon into a more toroidal shape.

In one embodiment, the outer shaft 106 has an outside diameter of about 0.2 inches, and a wall thickness of about 0.01 inches. The inner shaft 124 desirably has sufficient clearance to allow it to fit within the outer shaft. The wall thickness of the inner shaft 124 is preferably about 0.01 inches. In embodiments where the shafts move relative to one another, the inner shaft has sufficient clearance to allow it to slide relative to the outer shaft.

In one embodiment, the distal end 152 of the balloon 112 is attached or bonded over the distal 0.25 inches of the inner shaft 124, and the proximal end 150 of the balloon is attached or bonded over the distal 0.25 inches of the outer shaft 106. The distal end 152 of the balloon 112 is inverted before it is attached to the outer surface of the inner shaft 124. As a result, when the balloon is inflated, the attachment of the distal end of the balloon to the distal end of the instrument is located inside the inflated balloon.

In one embodiment, the proximal ends of the outer and inner shafts may be contained within a hub connector, a handle, or a housing that provides for easy manual control of the shafts for slidably moving the outer shaft forward relative to the inner shaft a distance of up to about 0.75 inches. The hub connector, handle, or housing may include an element for manually inflating and deflating the balloon. The hub connector, handle, or housing may resemble those of other trigger-operated endoscopic devices, such as the EES Proximate Stapler line or the Ethicon Morcellex device.

Referring to FIGS. 2 and 3, the inner shaft 124 has a central lumen 160 that extends from the distal end 148 of the inner shaft to a proximal end 162 of the inner shaft. In one embodiment, the central lumen 160 is preferably aligned with the second connection port 144 so that a stylet 164, as shown in FIGS. 4A-4C, may be inserted through the second connection port and into the central lumen 160.

Referring to FIG. 4A, the stylet 164 includes a rod 166 having a proximal end 168 and a distal end 170. Referring to FIG. 4B, the distal end 170 of the stylet includes a plug 172 having an outer surface 174 defining an outer diameter that closely matches an inner diameter of the central lumen 160 of the inner shaft 124. The distal end 170 of the stylet 164 also preferably includes hook-like barbs 176 that project from the distal end. As will be described in more detail below, the barbs 176 are adapted to hold a hemostat, such as a hemostat patch, onto the distal end of the stylet 164 during a surgical procedure. Referring to FIG. 4C, the proximal end 168 of the stylet 164 includes a handle 178 having a leading face 180, a rim 182 projecting from the leading face 180, and internal threads 184 provided inside the rim 182. The proximal end 168 of the rod 166 is secured to the leading face 180 of the handle 178 via a tapered hub 185 located inside the rim 182. In one embodiment, the taper angle of the tapered hub 185 preferably matches the taper of the opening of the second connector port.

Figure 5A:
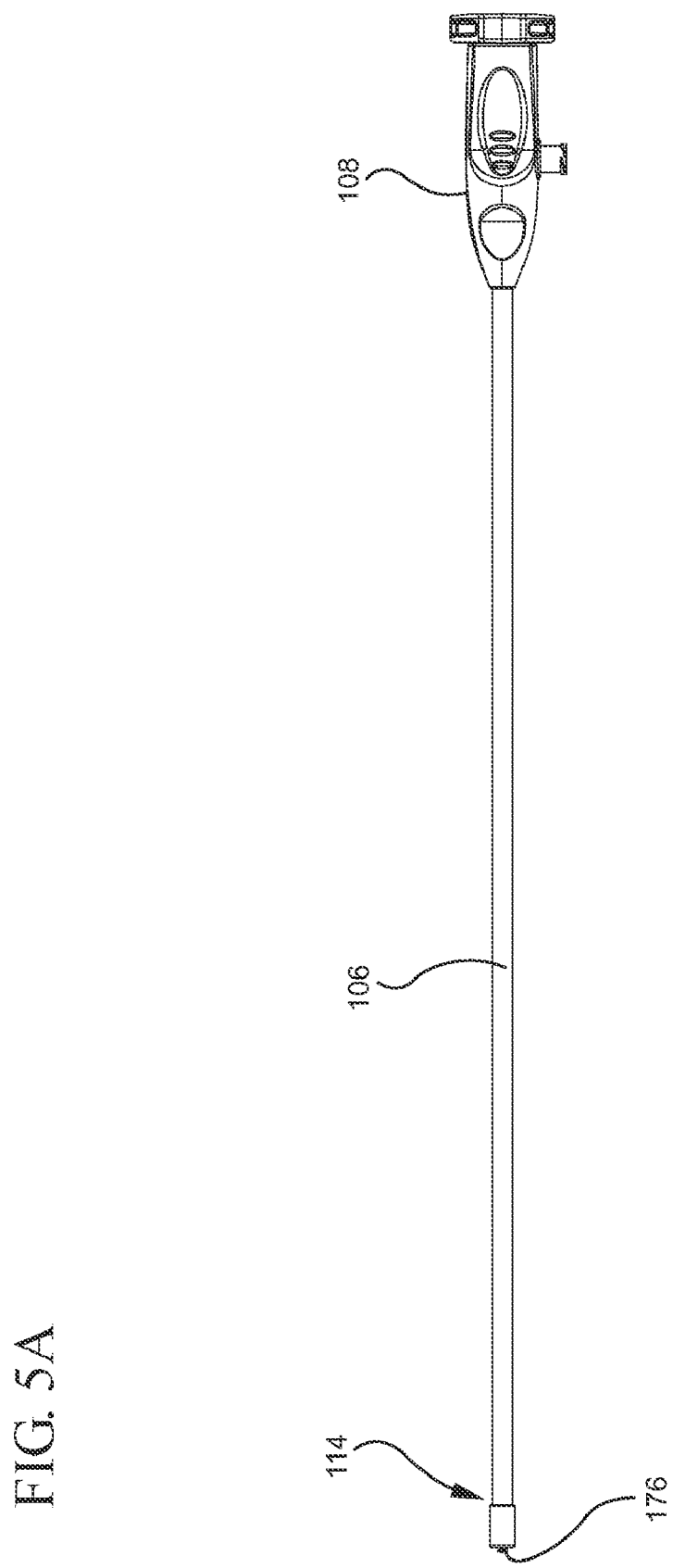
FIG. 5A shows a front elevational view of the instrument of FIG. 1 after the stylet of FIGS. 4A-4C has been into the hub connector and advanced toward the distal end of the instrument.
Figure 5B:
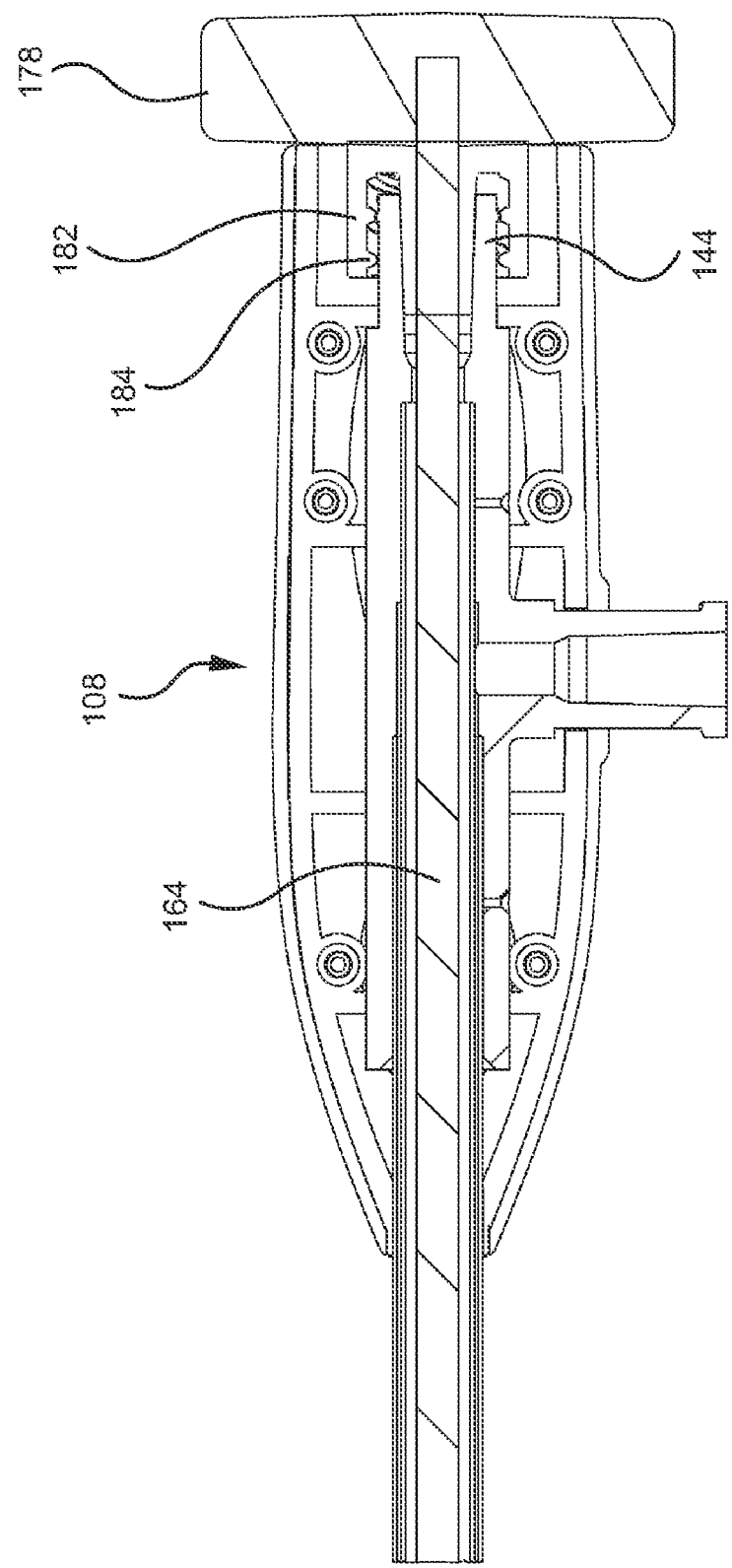
FIG. 5B shows a cross-sectional view of the hub connector after the stylet has been inserted into the hub connector.

Referring to FIGS. 5A and 5B, in one embodiment, the distal end of the stylet 164 is inserted into the second connection port 144 of the hub connector 108 and advanced toward the distal end 114 of the instrument until the barbs 176 protrude from the distal end of the inner shaft. Once the barbs are protruding from the distal end of the inner shaft, the tapered hub 185 of the stylet preferably engages the tapered opening of the second connection port 144. In addition, the internal threads 184 on the rim 182 of the handle 178 preferably engage the external threads 146 around the second connection port 144 for securing the proximal end of the stylet 164 to the second connection port.

Figure 6A:
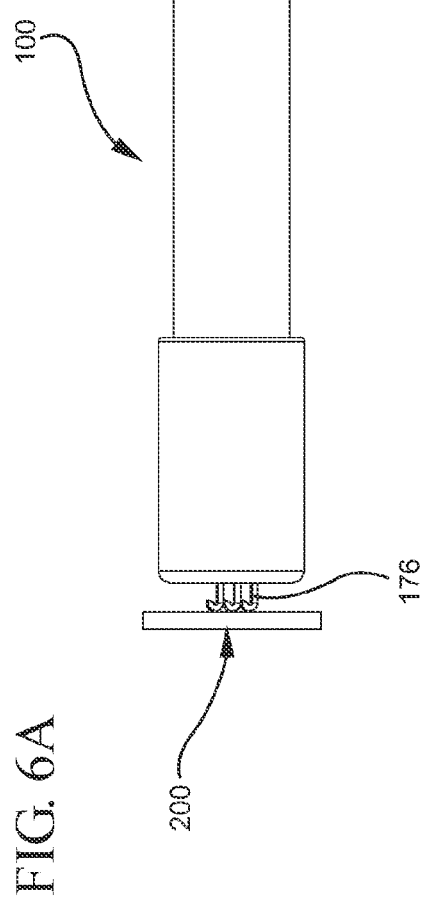
FIG. 6A shows a front elevational view of the distal end of the instrument shown in FIG. 5A.
Figure 6B:
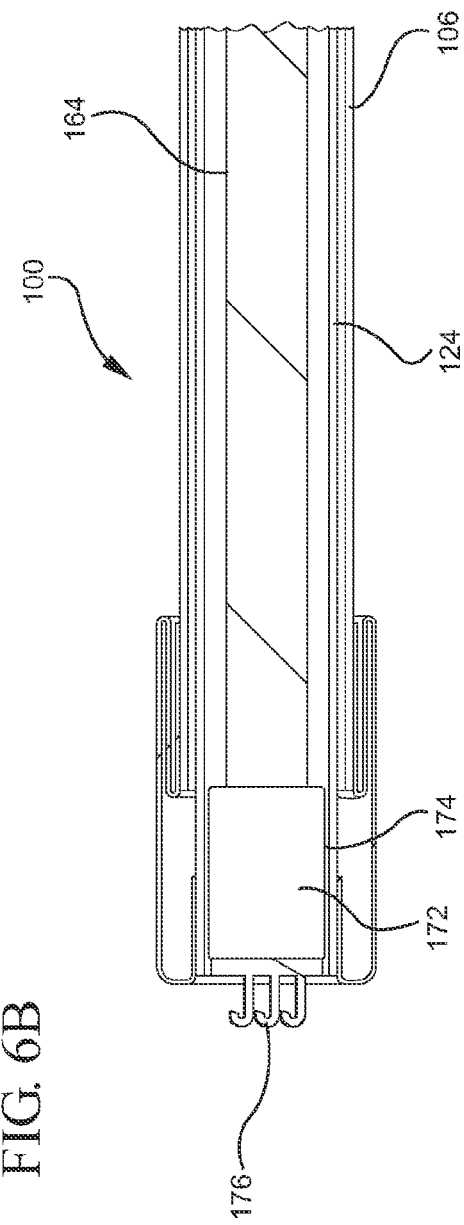
FIG. 6B shows a cross-sectional view of the distal end of the instrument shown in FIG. 6A.

Referring to FIGS. 6A and 6B, after the stylet 164 has been advanced to the distal end 148 of the inner shaft 124, the barbs 176 desirably project from the distal end of the instrument 100. Referring to FIG. 6B, the outer surface 174 of the plug 172 engages the inner surface of the inner shaft 124 to form a fluid-tight or air-tight seal at the distal end 148 of the inner shaft 124. With the balloon in the deflated state shown in FIGS. 6A and 6B, the barbs 176 may be used to secure a hemostat 200 to the distal end of the instrument 100. The distal end of the instrument may then be positioned at a surgical site for delivering the hemostat 200 to the surgical site. The balloon 112 may then be inflated for decoupling the hemostat from the barbs 176, and pressing the hemostat onto tissue at the surgical site.

Figure 7A:
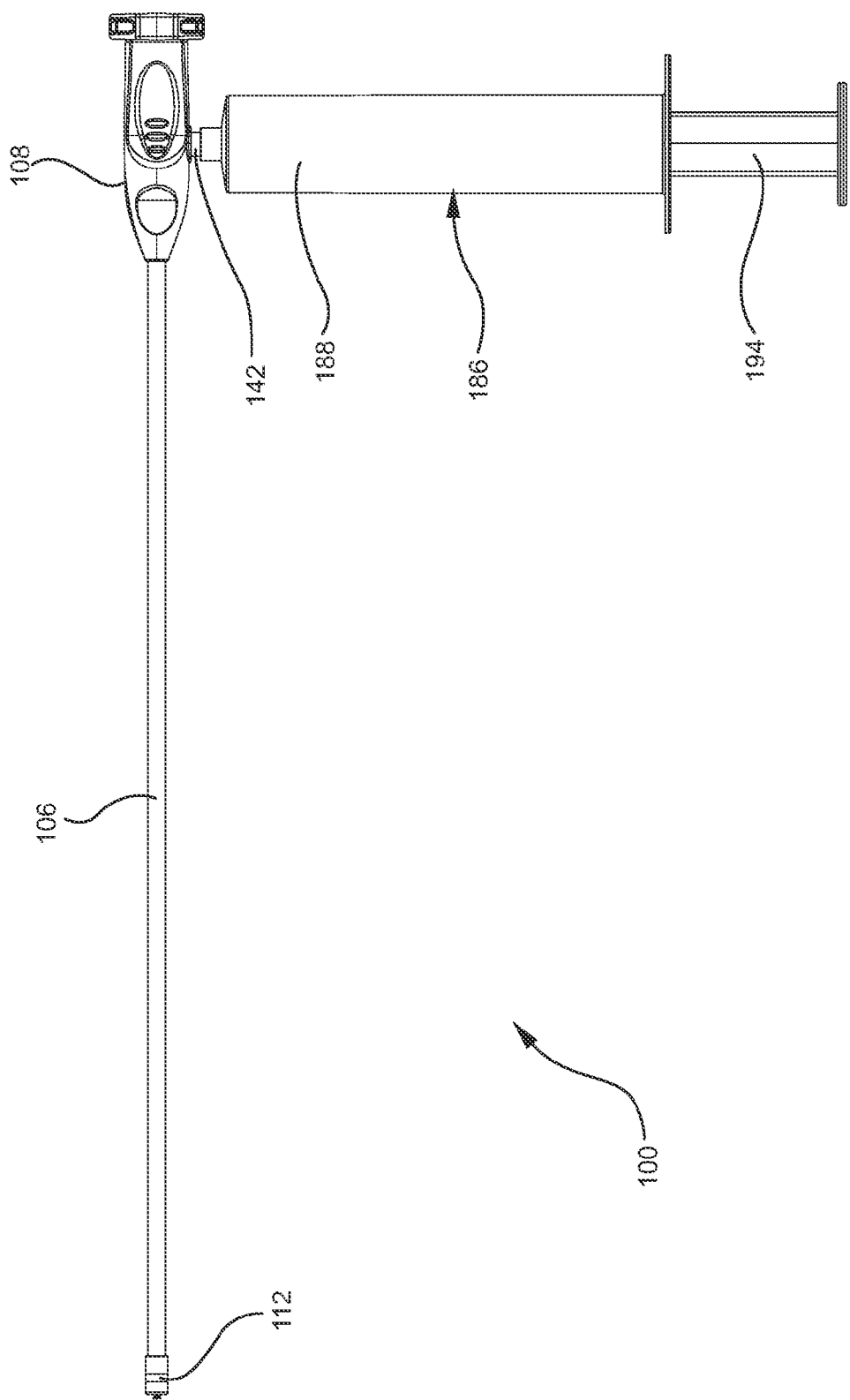
FIGS. 7A-7B show the instrument of FIG. 5A including an actuator for selectively inflating the inflatable balloon located at the distal end of the instrument.
Figure 7B:
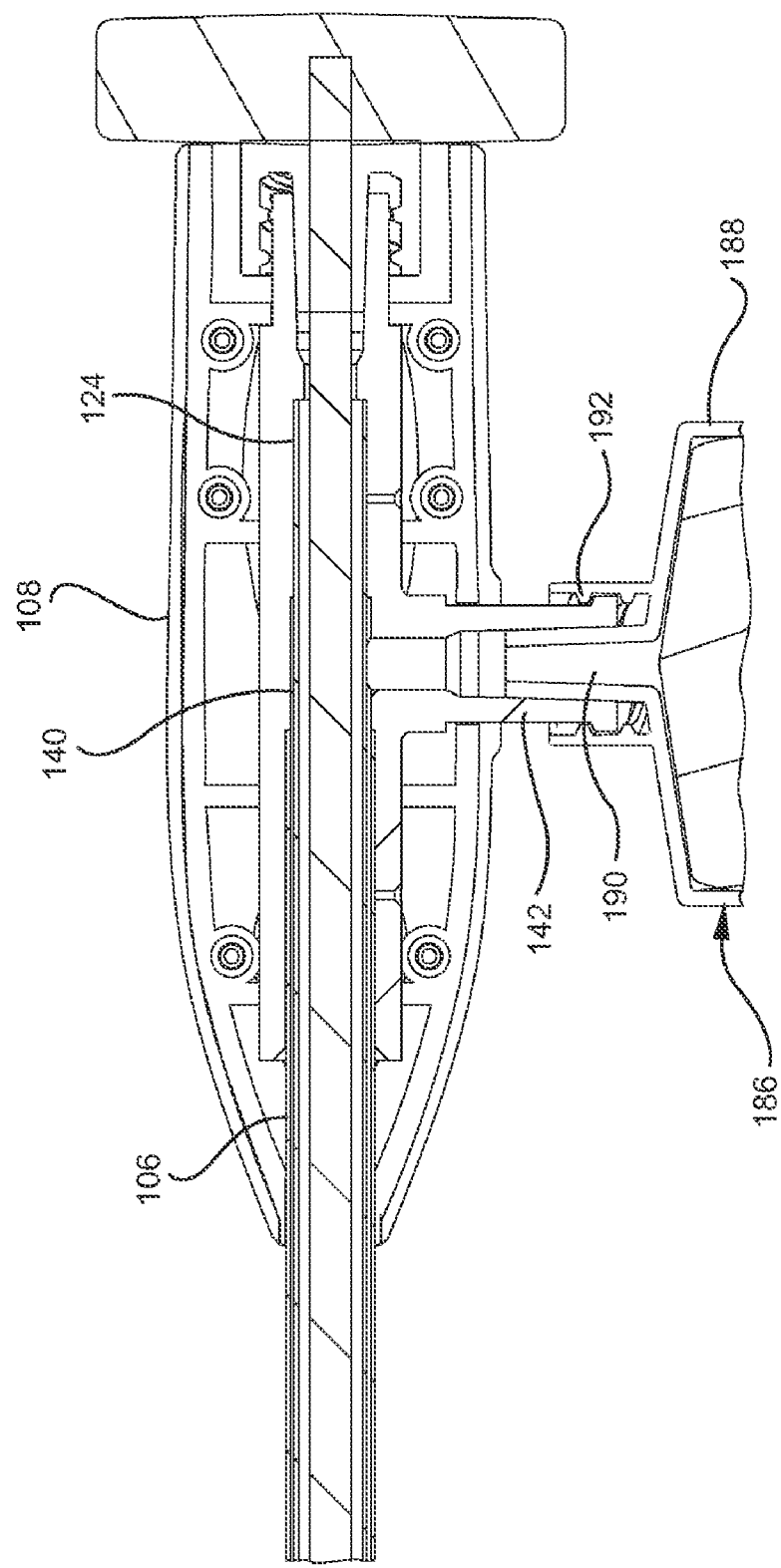

Referring to FIGS. 7A and 7B, in one embodiment, a first actuator 186 is coupled with the first connection port 142 of the hub connector 108 for inflating the balloon 112 at the distal end of the instrument 100. In one embodiment, the first actuator 186 is a syringe having a barrel 188 with a tip 190 that is insertable into the first connection port 142 and held in place by a Luer connector 192. The first actuator includes a plunger 194 that is depressible into the barrel 188 for forcing fluid through the tip 190 and into the first conduit 140 extending between the outer shaft 106 and the inner shaft 124. FIG. 7A shows the plunger 194 is an extended position, with the balloon 112 in a deflated state.

FIGS. 8A and 8B show the instrument 100 with the plunger 194 of the first actuator 186 in a compressed position for inflating the inflatable balloon 112. As the balloon is inflated, the leading face 196 of the balloon 112 initially forces the hemostat from the barbs. As the balloon 112 is further inflated to the state shown in FIGS. 8A, 8B, and 9, the leading face 196 of the balloon preferably becomes flatter to provide a larger surface area for applying tamponade pressure to the hemostat 200 delivered by the instrument 100. In one embodiment, the balloon 112 is preferably transparent so that medical personnel may observe the hemostat through the walls of the inflated balloon.

Figure 9:
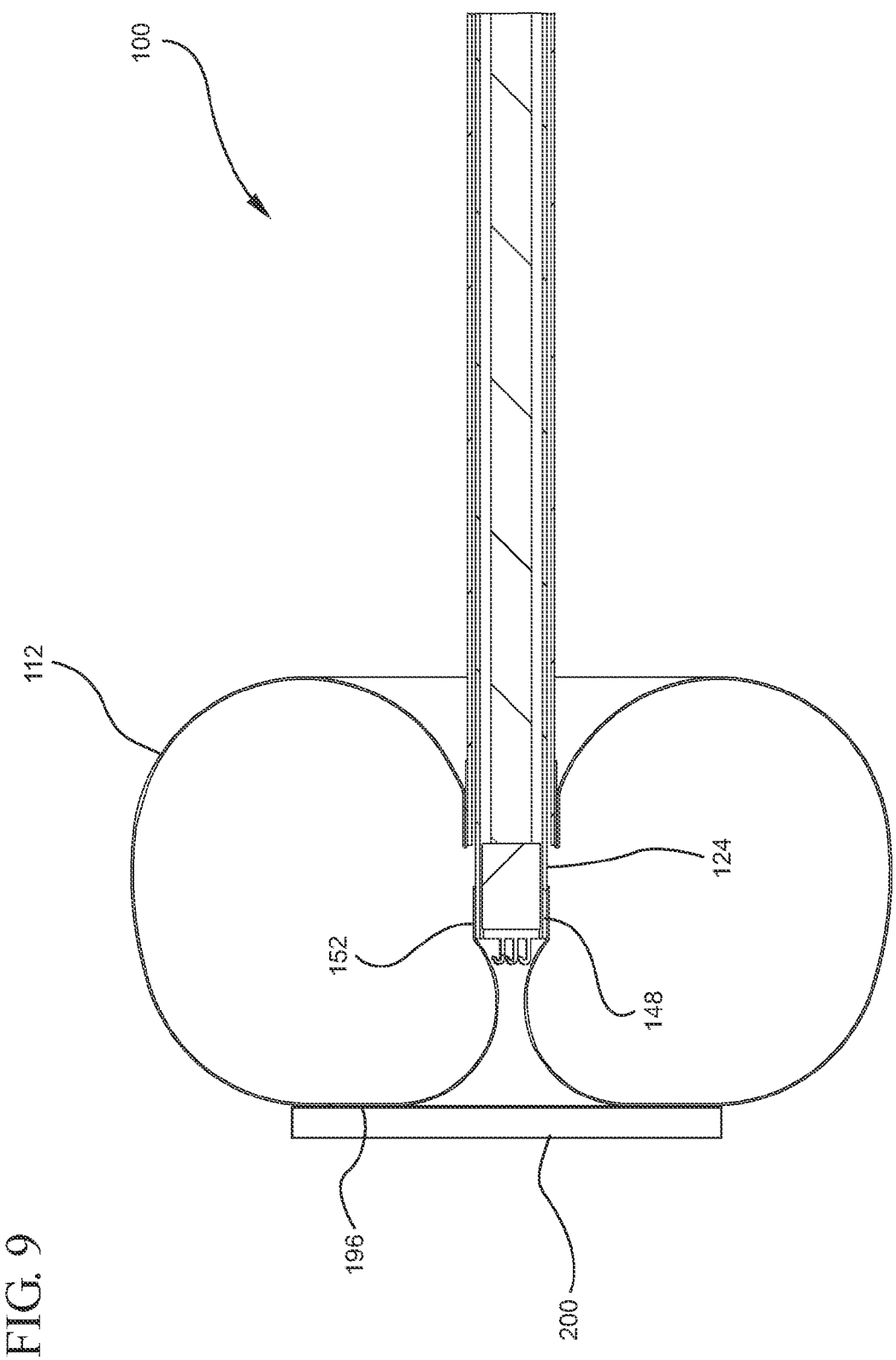
FIG. 9 shows a cross-sectional view of the distal end of the instrument of FIG. 5A after the balloon has been inflated.

As shown in FIG. 9, the inverted configuration of the distal end 152 of the balloon 112, and the attachment of the inverted distal end 152 to the distal end 148 of the inner shaft 124, results in the leading face 196 of the inflated balloon projecting distally of the distal end 148 of the inner shaft 124. This results in the inflated balloon 112 forming the distal-most position of the instrument 100 for engaging the hemostat. The attachment configuration also provides a balloon 112 having a flatter leading face 196 than would be possible with a balloon that does not invert the distal end.

Referring to FIGS. 10A and 10B, in one embodiment of the invention, all of the elements shown and described above remain the same except that the stylet of FIGS. 4A-4C is replaced by a second actuator 1210 that carries a flowable material such as a flowable hemostat or a flowable sealant. In one embodiment, the second actuator 1210 is a syringe including a barrel 1212 having a dispensing tip 1214 and a Luer connector 1216 that surrounds the tip 1214. The Luer connector desirably includes internal threads 1218 that are adapted to engage the outer threads 146 of the second connection port 144 of the hub connector 108 (FIG. 2). The second actuator 1210 preferably includes a plunger 1220 that is depressible for forcing the flowable material through the dispensing tip 1214 and into the central lumen of the inner shaft so as to dispense the flowable material from the distal end of the instrument. The inflated balloon may then be used to press the flowable material onto the tissue at the surgical site.

In another embodiment, the second actuator includes a sealant dispensing system such as the system sold under the trademark EVICEL™ by Johnson & Johnson of New Brunswick, N.J. The sealant dispensing system may include one or more catheters that are inserted through the central lumen of the inner shaft so that the dispensing ends of the one or more catheters are located at the distal end of the inner shaft. The sealant dispensing system may include one or more syringes and a Luer connector for coupling to the hub connector.

Figure 11A:
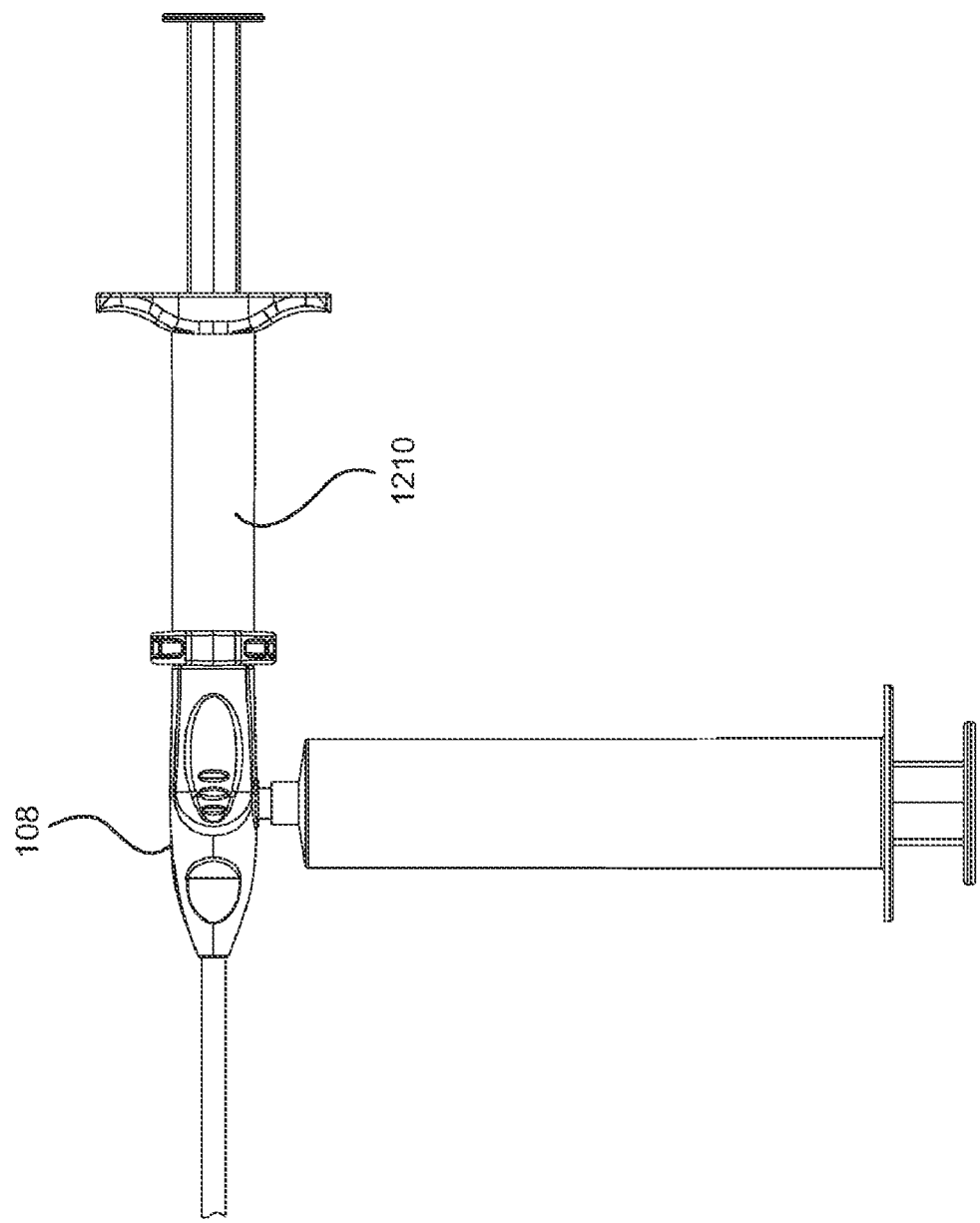
FIGS. 11A and 11B show front elevational and cross-sectional views, respectively, of the second actuator of FIGS. 10A and 10B coupled with a hub connector of an instrument for controlling bleeding.
Figure 11B:
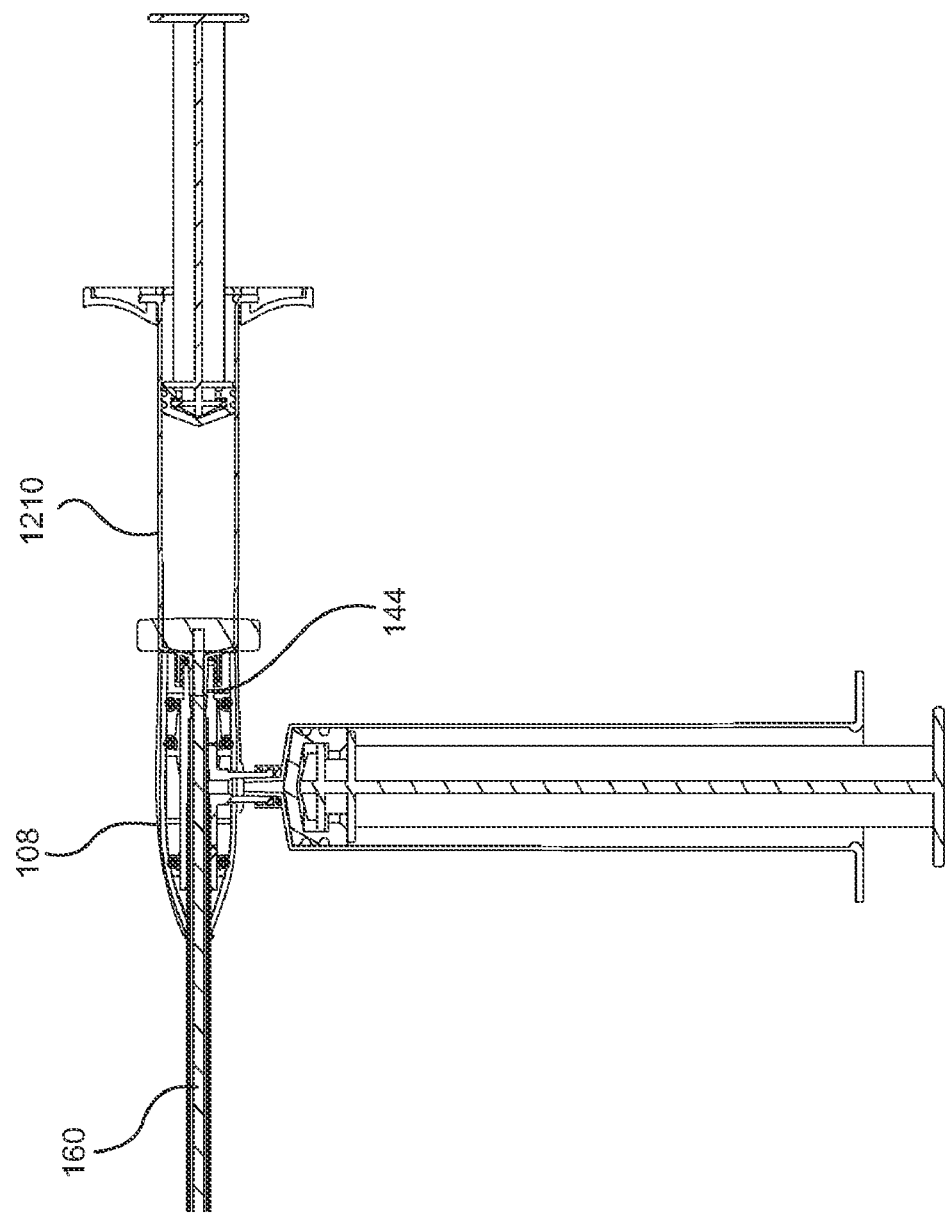

FIGS. 11A and 11B show the second actuator 1210 secured to the second connection port 144 of the hub connector 108. The dispensing tip 1214 is positioned in communication with the central lumen 160 of the inner shaft so that flowable material contained within the chamber of the barrel 1212 may be dispensed into the central lumen for advancement to the distal end of the central lumen 160.

Figure 12B:
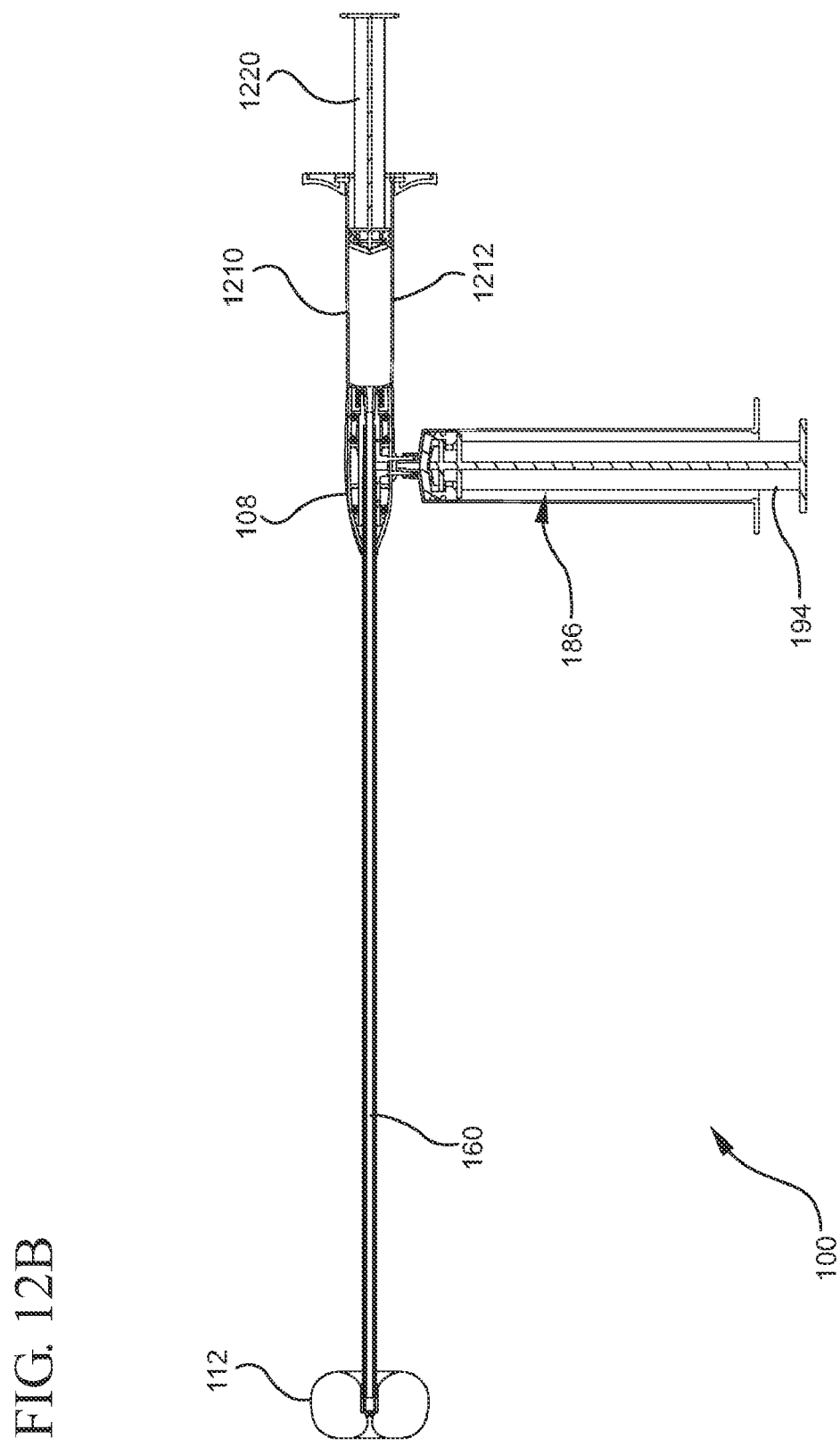

FIGS. 12A and 12B show the instrument 100 having the first actuator 186 coupled with the first connection port of the hub connector 108, and the second actuator 1210 coupled with the second connection port of the hub connector 108. In FIGS. 12A and 12B, the plunger 194 of the first actuator 186 has been depressed for inflating the inflatable balloon 112. The plunger 1220 of the second actuator 1210 may also be depressed for dispensing the flowable material from the barrel 1212 and into the central lumen 160 of the inner shaft. In one embodiment, the balloon 112 is inflated before the flowable material is dispensed from the second actuator. In a second embodiment, the flowable material is dispensed before the balloon is inflated. In another embodiment, the balloon may be inflated at the same time, or around the same time, that the flowable material is being dispensed from the second actuator. In still other embodiments, the exact order for inflating the balloon and dispensing the flowable material may change.

Figure 13B:
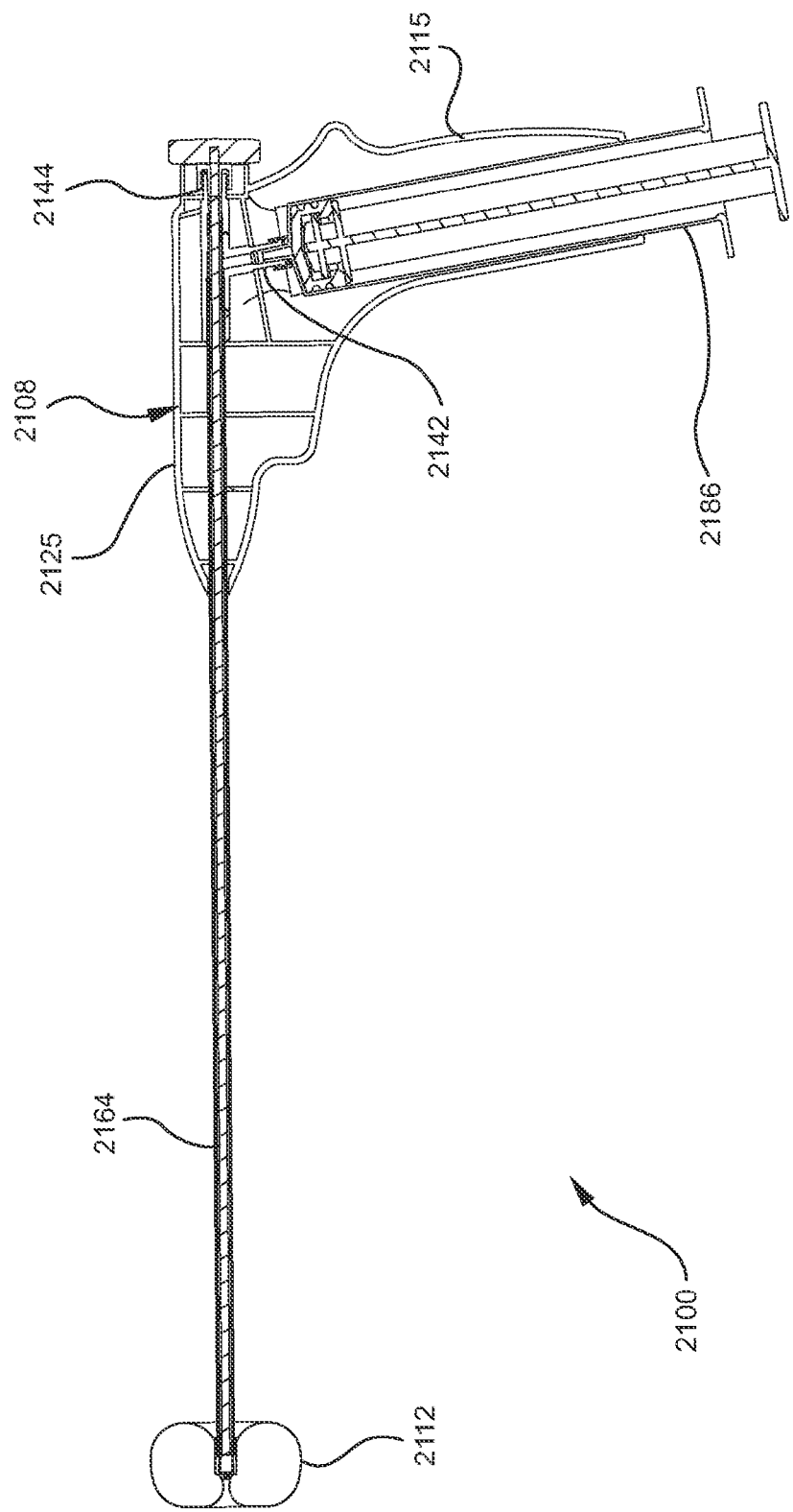

Referring to FIGS. 13A and 13B, in one embodiment, an instrument 2100 for controlling bleeding includes a handle 2108 that replaces the hub connector 108 shown and described above. The handle 2108 has a vertically extending trigger portion 2115 that includes a first connection port 2142 for receiving a first actuator 2186, and a horizontally extending section 2125 that includes a second connection port 2144 adapted to receive a stylet 2164. In one embodiment, the handle 2108 has all of the features shown and described above for the hub connector 108. The handle 2108 preferably has an ergonomic design that enables it to be more easily grasped by an operator during a surgical procedure. In operation, the barbs at the distal end of the stylet 2164 are adapted to hold a hemostat. The first actuator 2186 may be operated for selectively inflating the inflatable balloon 2112.

Figure 14A:
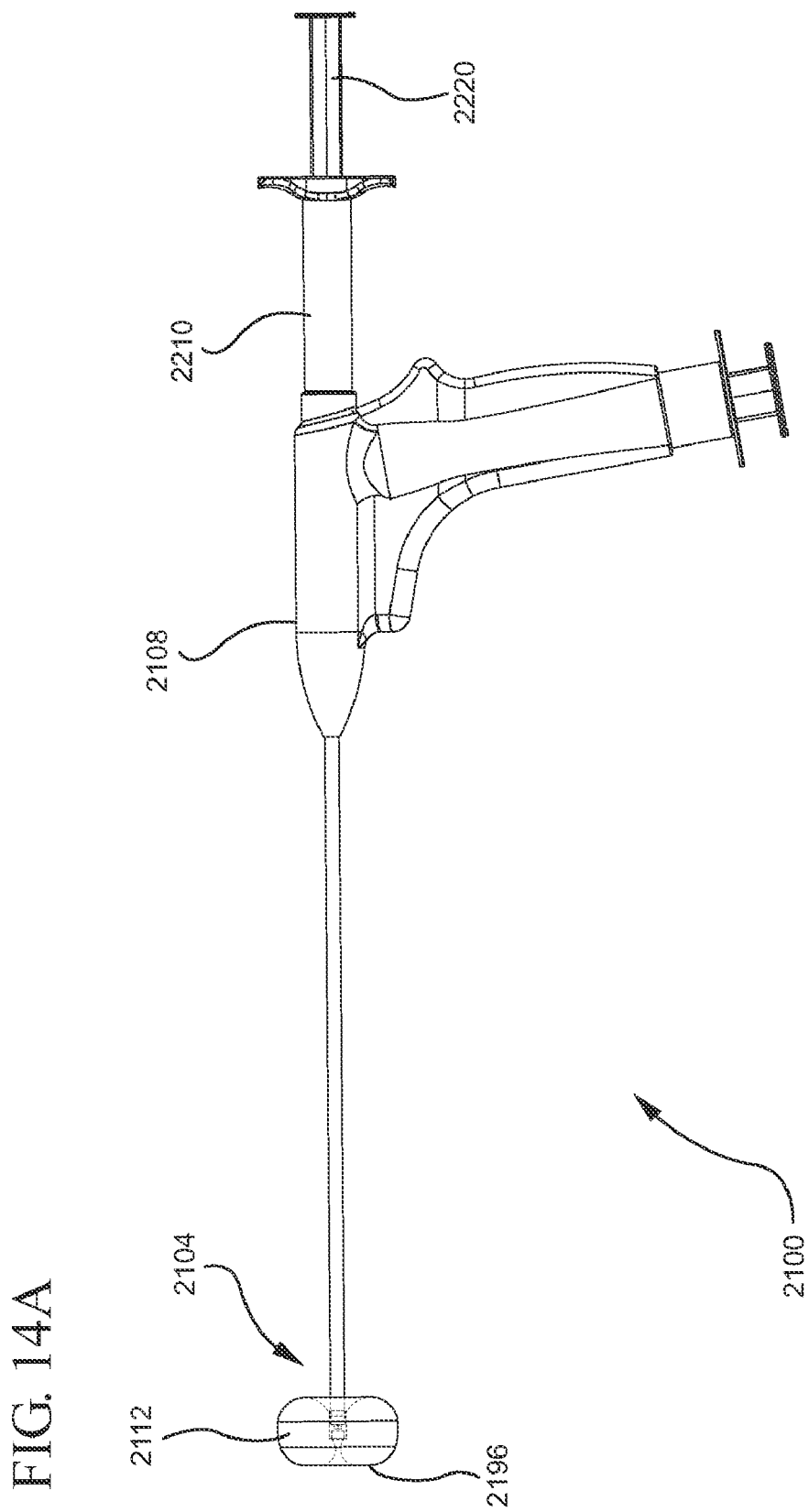
FIGS. 14A and 14B show front elevational and cross-sectional views, respectively, of an instrument for controlling bleeding, in accordance with one embodiment of the present invention.
Figure 14B:
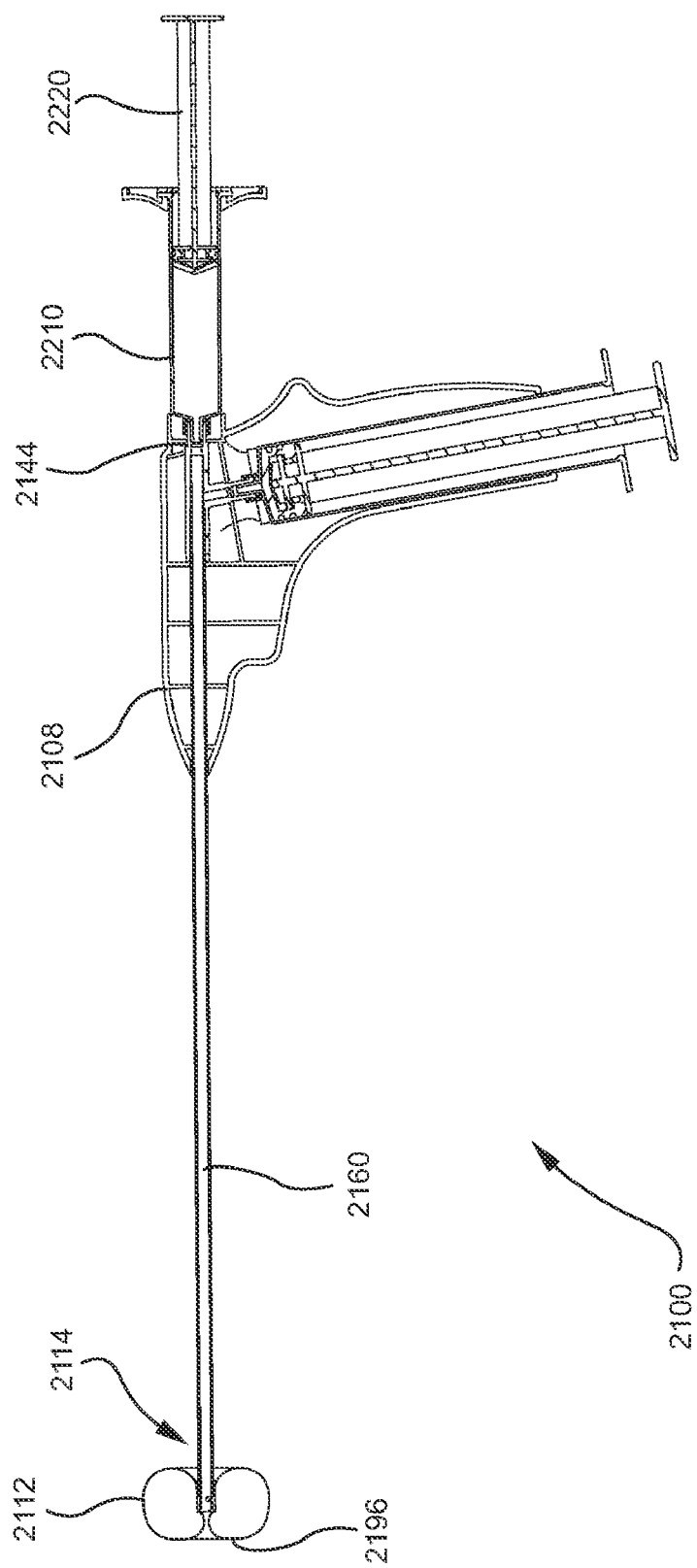

Referring to FIGS. 14A and 14B, in one embodiment, the stylet 2164 of FIGS. 13A and 13B is replaced by a second actuator 2210 containing a flowable material. In one embodiment, the dispensing tip of the second actuator is inserted into the second connection port 2144 of the handle 2108. The plunger 2220 of the second actuator 2210 is depressible for discharging the flowable material from the second actuator 2210 and into the central lumen 2160 of the inner shaft. The flowable material is preferably discharged from the distal end 2104 of the instrument 2100 and tamped onto the tissue at a surgical site by the leading face 2196 of the inflated balloon 2112.

Figure 15:
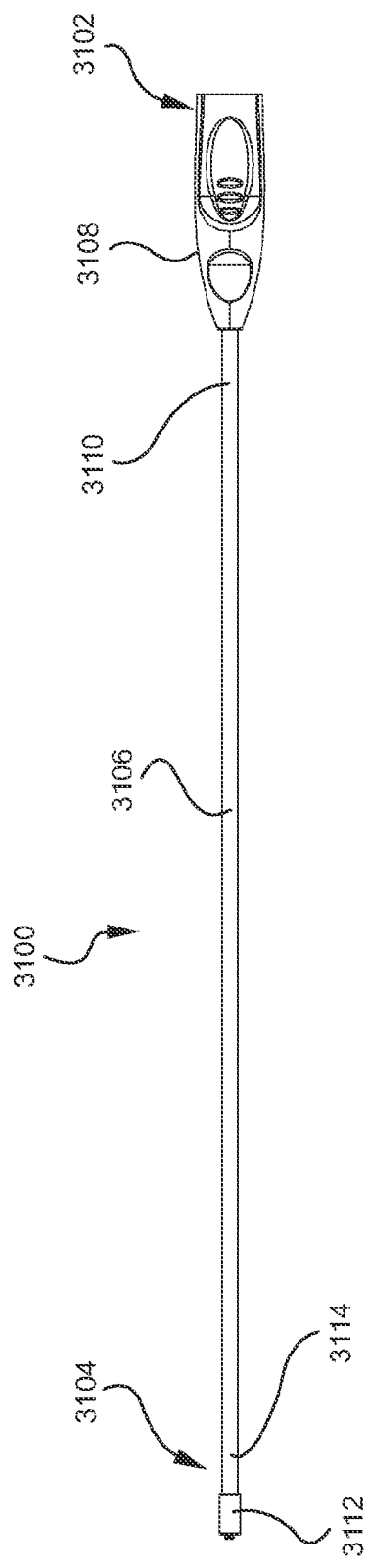
FIG. 15 shows a front elevational view of an instrument for controlling bleeding including a hub connector at a proximal end and an inflatable balloon at a distal end, in accordance with one embodiment of the present invention.

Referring to FIG. 15, in one embodiment, an instrument 3100 for controlling bleeding has a proximal end 3102, a distal end 3104, and a shaft 3106 that extends between the proximal and distal ends. The instrument includes a hub connector 3108 coupled with a proximal end 3110 of the shaft and an inflatable balloon 3112 coupled with a distal end 3114 of the shaft.

Figure 16A:
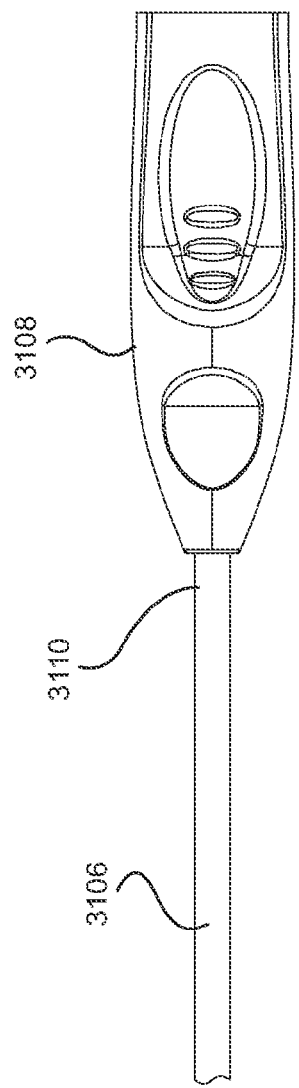
FIGS. 16A and 16B show respective front elevational and cross-sectional views of the hub connector and the proximal end of the instrument shown in FIG. 15.
Figure 16B:
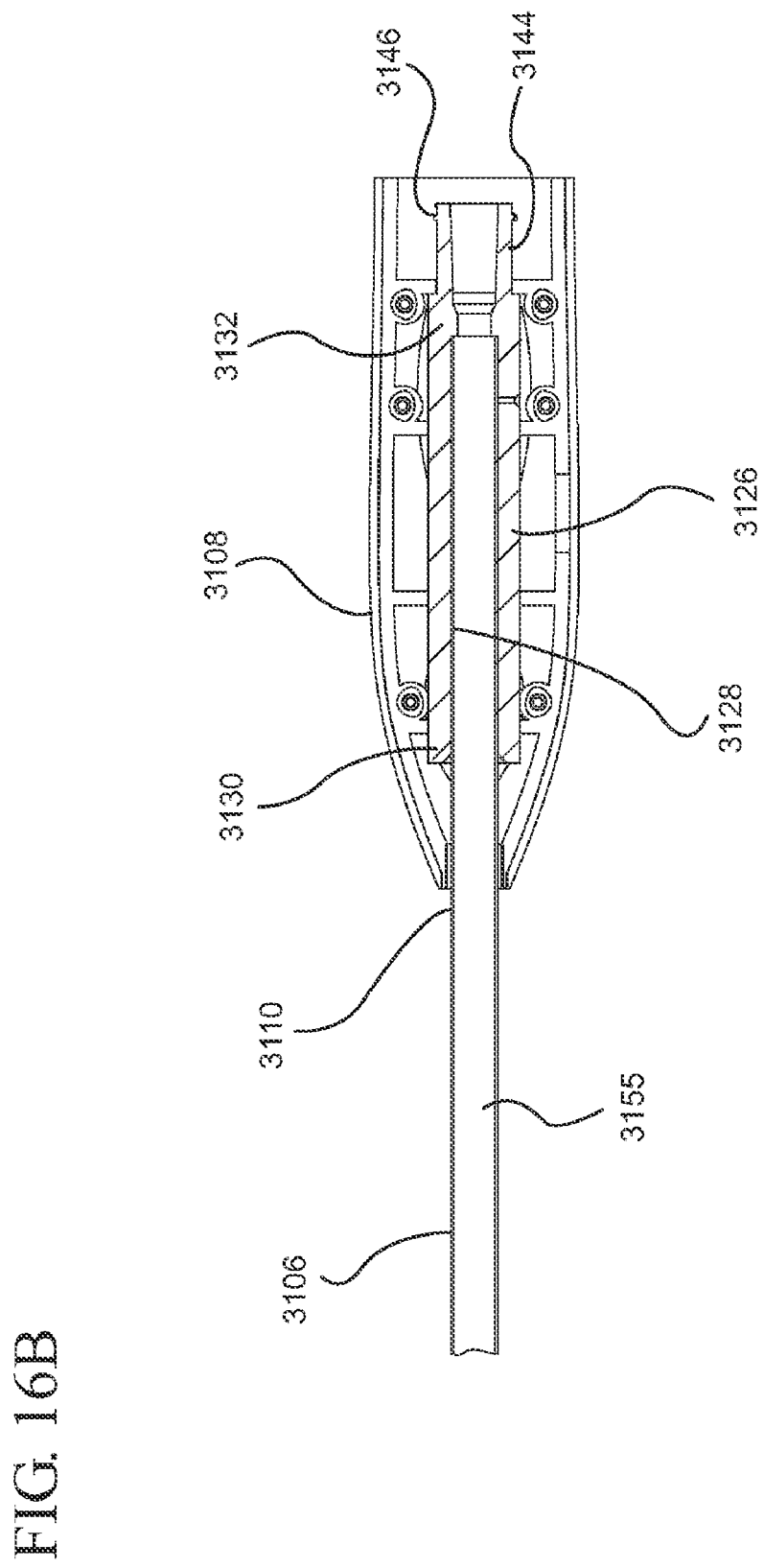

Referring to FIGS. 16A and 16B, the hub connector 3108 is secured to the proximal end 3110 of the shaft 3106. Referring to FIG. 16B, the hub connector 3108 includes a shaft support tube 3126 having a central bore 3128 that extends between a leading end 3130 and a trailing end 3132 of the shaft support tube. The central bore 3128 has an inner diameter that closely matches the outer diameter of the shaft 3106. The hub connector 108 desirably includes a connection port 3144 adjacent the trailing end 3132 of the shaft support tube 3126. Threads 3146 are provided around the trailing end 3132 of the shaft support tube 3126 to provide a threaded coupling for an opposing element, such as a Luer connector, as will be described in more detail below. The shaft 3106 desirably has a central lumen 3155 that extends from the proximal end to the distal end of the shaft 3106. The central lumen 3155 is preferably in communication with the connection port 3144 at the trailing end of the hub connector 3108. Although FIG. 16B shows an embodiment whereby the connection port 3144 is aligned with the central lumen, in other embodiments it is contemplated that the connection port 3144 may be provided at a wide range of orientations relative to the central lumen 3155 and still fall within the scope of the present invention.

Figure 17:
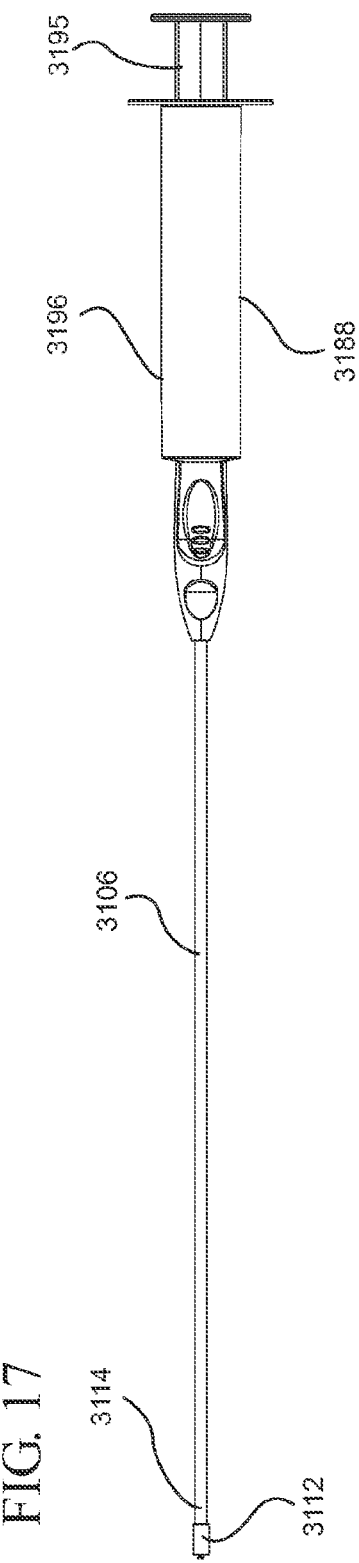
FIG. 17 shows a front elevational view of the instrument of FIG. 15 having an actuator coupled with the hub connector at the proximal end.
Figure 18:
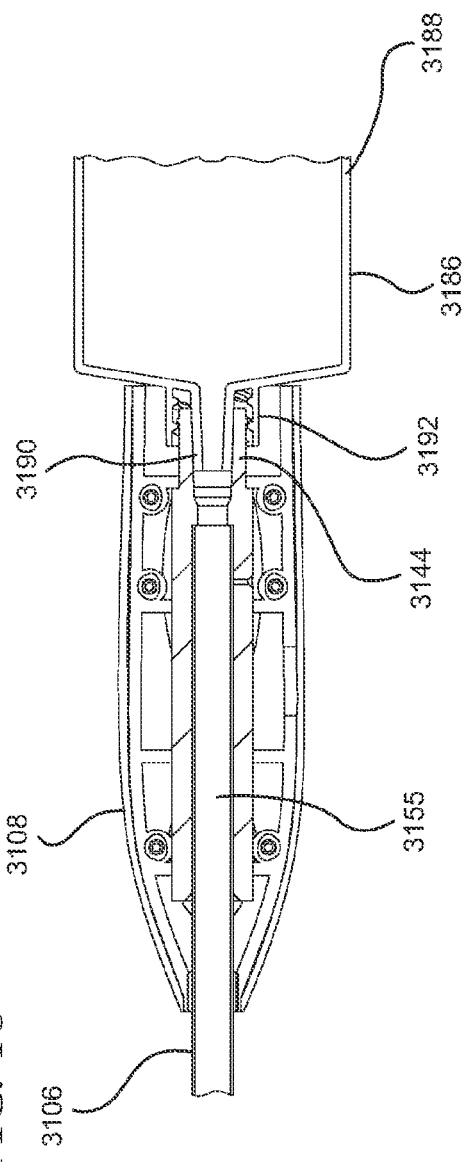
FIG. 18 shows a cross-sectional view of the hub connector of FIG. 15 with the actuator coupled therewith.

Referring to FIGS. 17 and 18, in one embodiment an actuator 3186 is coupled with the connection port 3144 of the hub connector 3108 for inflating the balloon 3112 at the distal end 3114 of the shaft 3106. The actuator 3186 desirably includes a syringe having a barrel 3188 with a tip 190 that is insertable into the connection port 3144 and held in place by a Luer connector 3192 having internal threads that engage the threads 3146 around the connection port 3144. The actuator includes a plunger 3194 that is depressible into the barrel 3188 for forcing fluid through the tip 3190 and into the central lumen 3155 of the shaft 3106.

Referring to FIGS. 19A and 19B, in one embodiment, the distal end 3104 of the instrument 3100 includes the shaft 3106 and the central lumen 3155 that extends to the distal end of the shaft. As shown in FIG. 19B, an opening at the distal end of the shaft 3106 is sealed by a plug 3172 that forms an air-tight seal at the distal end of the shaft. The instrument 3100 includes the inflatable balloon 3112 having a proximal end 3150 secured to the shaft 3106, and a distal end 3152 that is secured to the distal end 3114 of the shaft 3106. The distal end 3152 of the balloon 3112 is preferably secured to a more distal section of the shaft than the proximal end 3150 of the balloon 3112. The distal end 3152 of the inflatable balloon 3112 is preferably inverted, and the inverted distal end is preferably secured to an outer surface of the shaft 3106 at the distal end of the shaft. The above-described structure forms an air-tight compartment 3154 inside the inflatable balloon 3112. The distal end of the central lumen 3155 is preferably in communication with the compartment 3154 through an inlet opening 3140 extending though the outer wall of the shaft 3106. In one embodiment, fluid such as air may be directed through the central lumen 3155, the inlet opening 3140, and into the compartment 3154 for inflating the balloon 3112. When it is desirable to deflate the balloon 3112, the fluid may be removed from the balloon through the inlet opening 3140.

FIG. 20 shows the instrument 3100 with the plunger 3194 of the actuator 3186 in a compressed position for inflating the inflatable balloon 3112. As the balloon is inflated, the leading face 3196 of the balloon 3112 may force a hemostat away from the distal end of the instrument. When the balloon 3112 is inflated to the state shown in FIG. 21, the leading face 3196 of the balloon 3112 provides a flatter surface area that is preferably used to apply tamponade pressure to the hemostat 3200 delivered by the instrument 100. The balloon 3112 is preferably transparent so that medical personnel may observe the hemostat through the walls of the inflated balloon.

As shown in FIG. 21, the inverted configuration of the distal end 3152 of the balloon 3112, and the attachment of the inverted distal end 3152 to the distal end 3114 of the shaft 3106, results in the leading face 3196 of the inflated balloon projecting distally of the distal-most end 3114 of the shaft 3106. This results in the inflated balloon 3112 forming the distal-most extent of the instrument 3100. The leading face of the balloon may be used to apply pressure to a hemostat or a flowable hemostat material.

Referring to FIGS. 22A and 22B, in one embodiment, the plug 4172 at the distal end 4114 of the shaft 4106 includes hook-like barbs 4176 that project from the distal end of the plug. The barbs 4176 are preferably adapted to secure a hemostat to the distal end of the instrument. The barbs preferably hold the hemostat to the distal end of the instrument for delivering, deploying and tamponading a hemostat at a surgical site.

Figure 23:
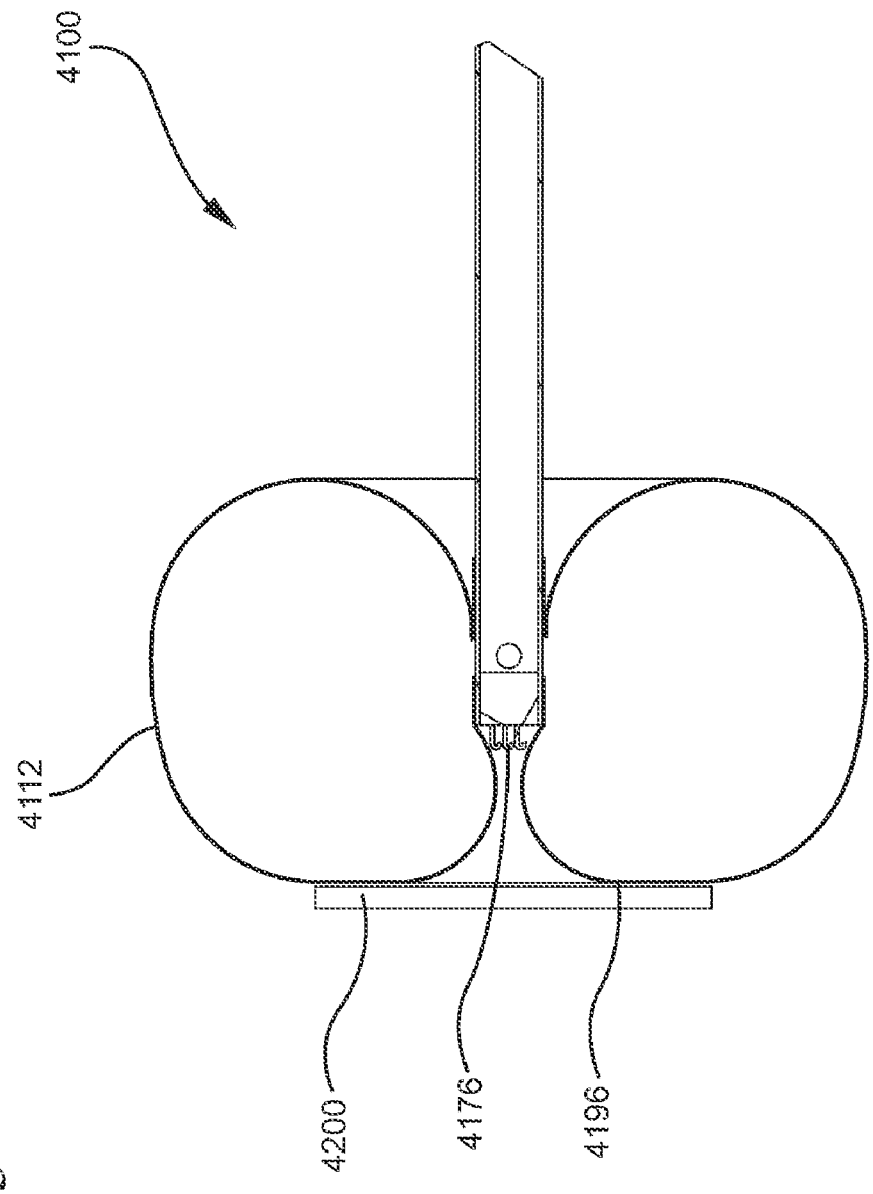
FIG. 23 shows the distal end of the instrument shown in FIG. 22B with the inflatable balloon in an inflated state.

Referring to FIG. 23, as the balloon 4112 is inflated, the leading face 4196 of the balloon 4112 initially forces the hemostat 4200 from the barbs 4176. As the balloon 4112 is further inflated to the state shown in FIG. 23, the leading face 4196 provides a flat, large surface area that is preferably used to apply tamponade pressure to the hemostat 4200 delivered by the instrument 4100. In one embodiment, the balloon 4112 is preferably transparent so that medical personnel may observe the hemostat 4200 through the walls of the inflated balloon so as to monitor bleeding at the surgical site.

Figure 24:
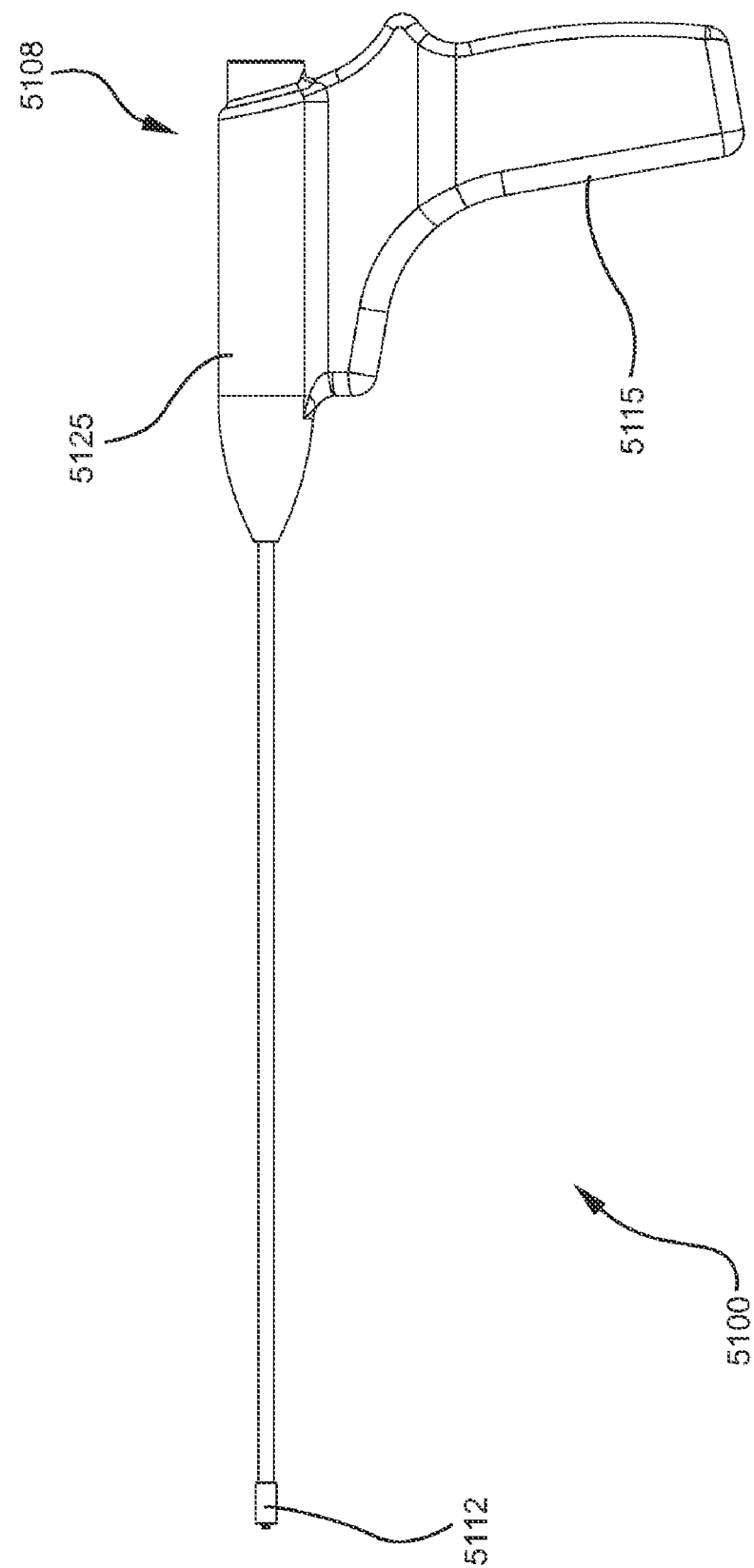
FIG. 24 shows an instrument for controlling bleeding including a hub connector at a proximal end and an inflatable balloon at a distal end, in accordance with one embodiment of the invention.
Figure 25:
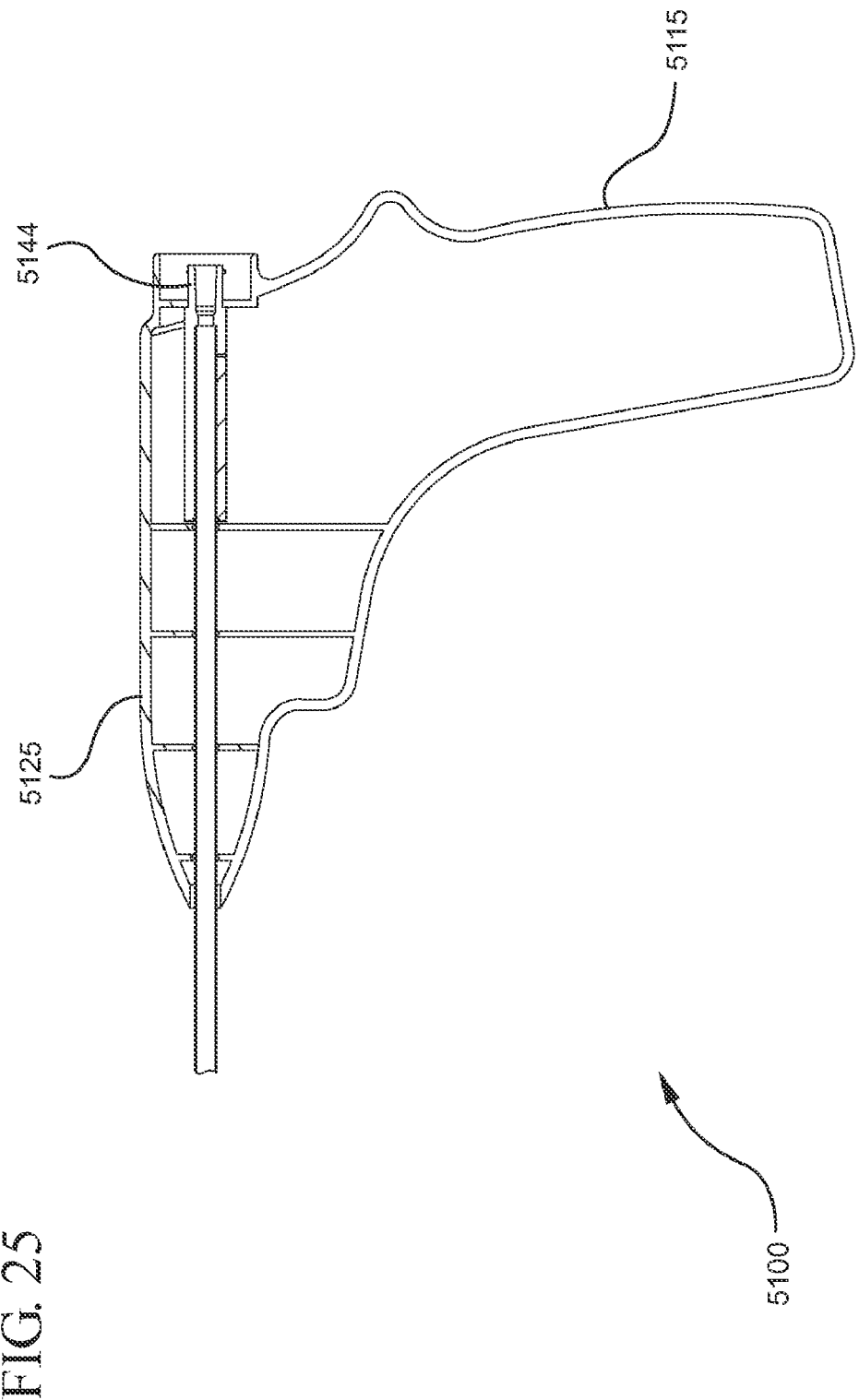
FIG. 25 shows a cross-sectional view of the hub connector of FIG. 24.

Referring to FIGS. 24 and 25, in one embodiment, an instrument 5100 for controlling bleeding includes a handle 5108 that replaces the hub connector 3108 shown and described above in the embodiment of FIG. 18. The handle 5108 has a vertically extending trigger-grip portion 5115, and a horizontally extending section 5125 that includes a connection port 5144 that is adapted to receive an actuator for inflating the inflatable balloon 5112. In one embodiment, the handle 5108 has all of the features shown and described above for the hub connector 3108 of FIG. 18. The handle 5108 preferably has an ergonomic design that enables it to be more easily grasped by an operator during a surgical procedure.

Figure 26:
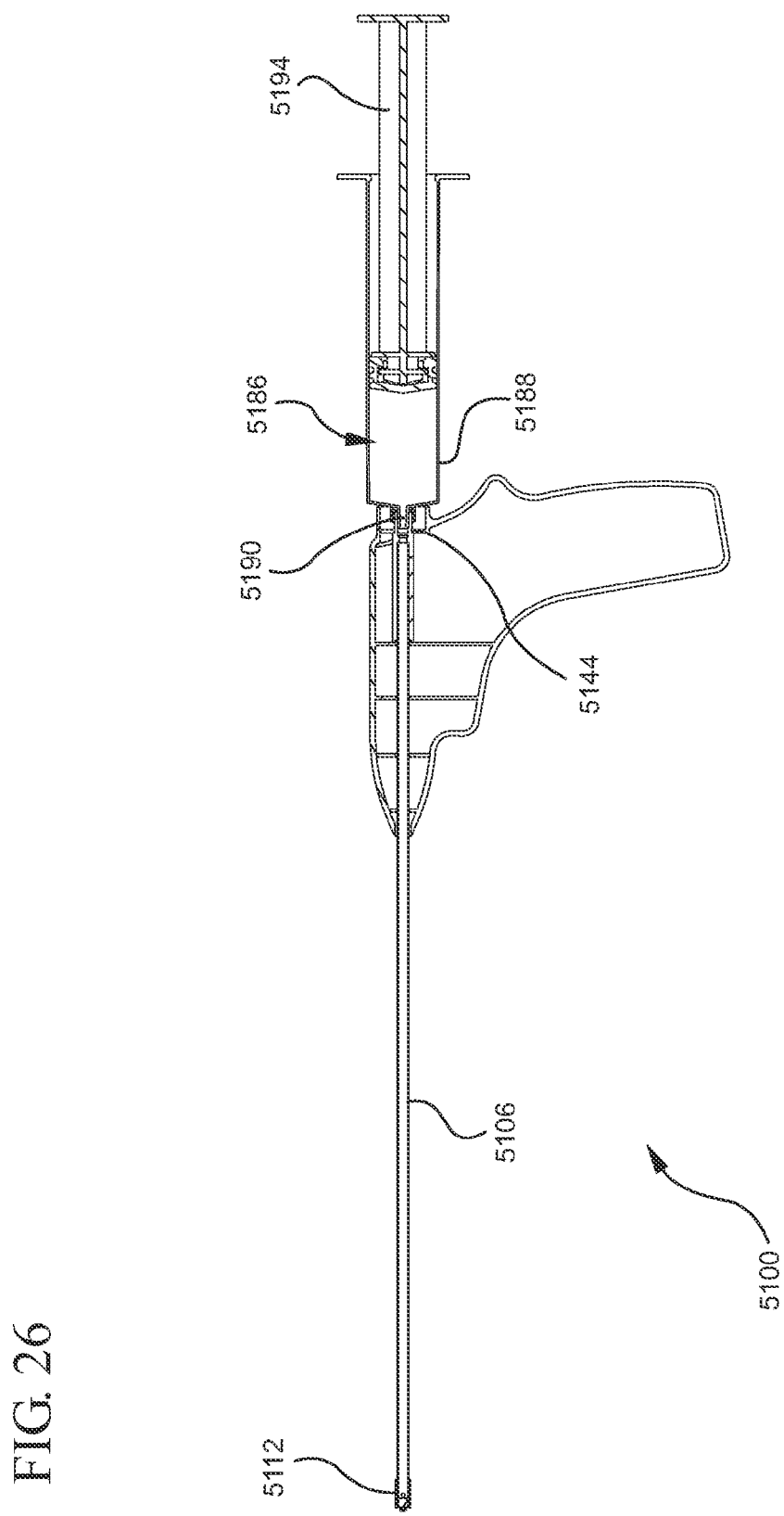
FIG. 26 shows a cross-sectional view of the instrument of FIG. 24 with an actuator for inflating the balloon coupled with the hub connector.
Figure 27:
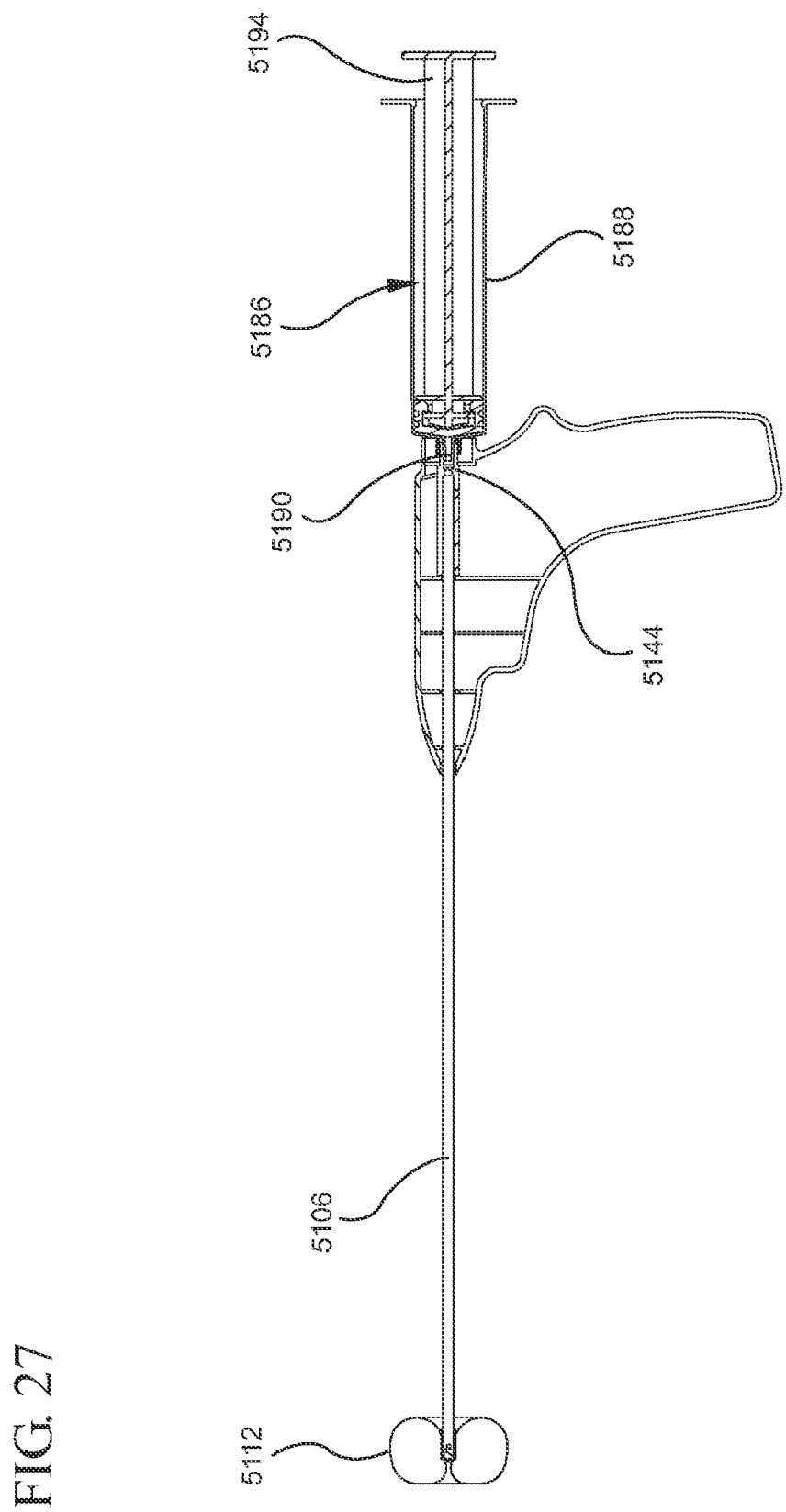
FIG. 27 shows the instrument of FIG. 26 with the inflatable balloon in an inflated state.

Referring to FIGS. 26 and 27, an actuator 5186 is coupled with the handle 5108. The actuator 5186 desirably includes a syringe having a barrel 5188 with a tip 5190 that is insertable into the connection port 5144. In one embodiment, the tip 5190 is held in place by a Luer connector having internal threads that engage threads around the connection port 5144. The actuator includes a plunger 5194 that is depressible into the barrel 5188 for forcing fluid, such as air, through the tip 5190 and into the central lumen 5155 of the outer shaft 5106. As the fluid is forced through the central lumen toward the distal end of the instrument 5100, the balloon 5112 is inflated as shown in FIG. 27.

Referring to FIGS. 28A and 28B, in one embodiment, an instrument 6100 for controlling bleeding includes an outer shaft 6106 and an inner shaft 6124 that is telescopically received in the outer shaft. As will be described in more detail below, the outer and inner shafts move relative to one another for altering the shape of an inflated balloon 6112. The instrument 6100 includes the outer shaft 6106 having a distal end 6114, and the inner shaft 6124 extending beyond the distal end of the outer shaft 6106. The inner shaft includes a central lumen 6160 that extends to the distal end thereof, and an inlet opening 6140 extending through the outer wall of the inner shaft. An opening at the distal-most end of the inner shaft is closed by a plug 6172 that forms an air-tight seal at the distal end of the inner shaft.

Figure 29:
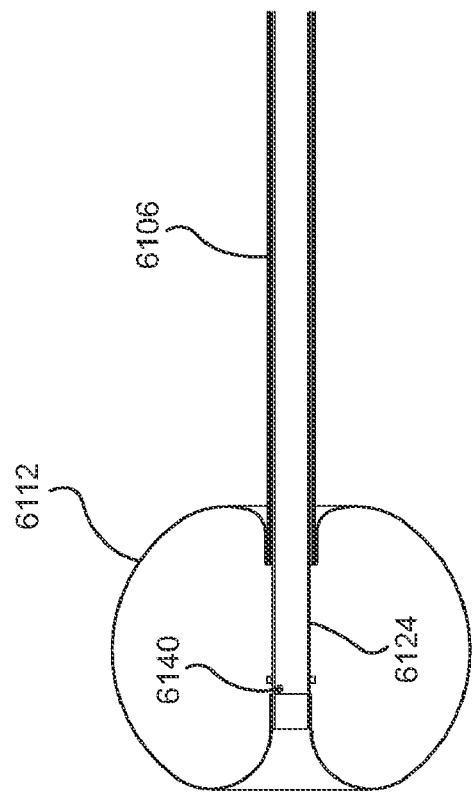
FIG. 29 shows the instrument of FIGS. 28A and 28B after the inflatable balloon at the distal end has been inflated.
Figure 30:
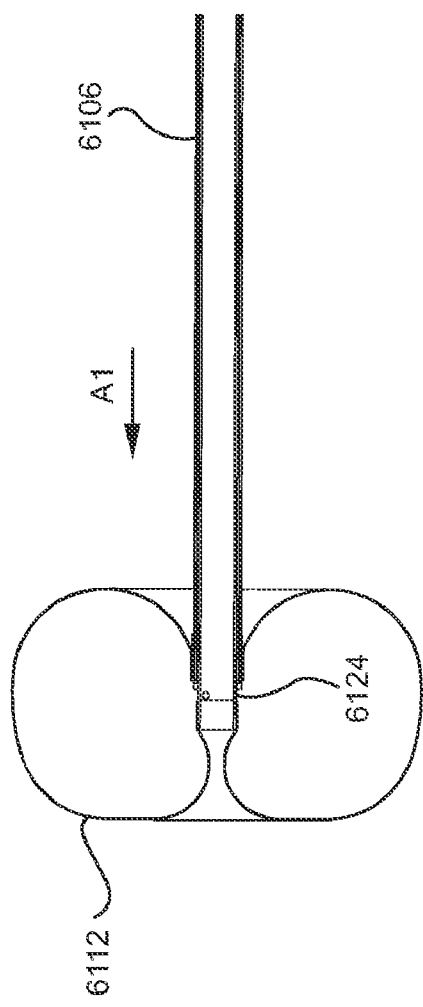
FIG. 30 shows the instrument of FIG. 29 after the shape of the inflated balloon has been altered.

The instrument 6100 includes the inflatable balloon 6112 having a proximal end 6150 that is secured to an outer surface of the outer shaft 6106, and a distal end 6152 that is secured to the distal end of the inner shaft 6124. The distal end of the balloon is preferably inverted before it is secured to the inner shaft. Referring to FIG. 29, the balloon 6112 may be inflated by directing fluid through the central lumen 6160 of the inner shaft 6124, through the inlet opening 6140, and into the balloon 6112. The shape of the balloon may be changed from the more spherical shape shown in FIG. 29 to the more toroidal shape shown in FIG. 30. In one embodiment, the shape of the balloon is changed by moving the outer shaft 6106 in the direction Al relative to the inner shaft. As the shape of the balloon changes, the leading face 6196 of the balloon flattens to provide a larger surface area at the distal-most end of the instrument for applying pressure to a hemostat at a surgical site.

Figure 31A:
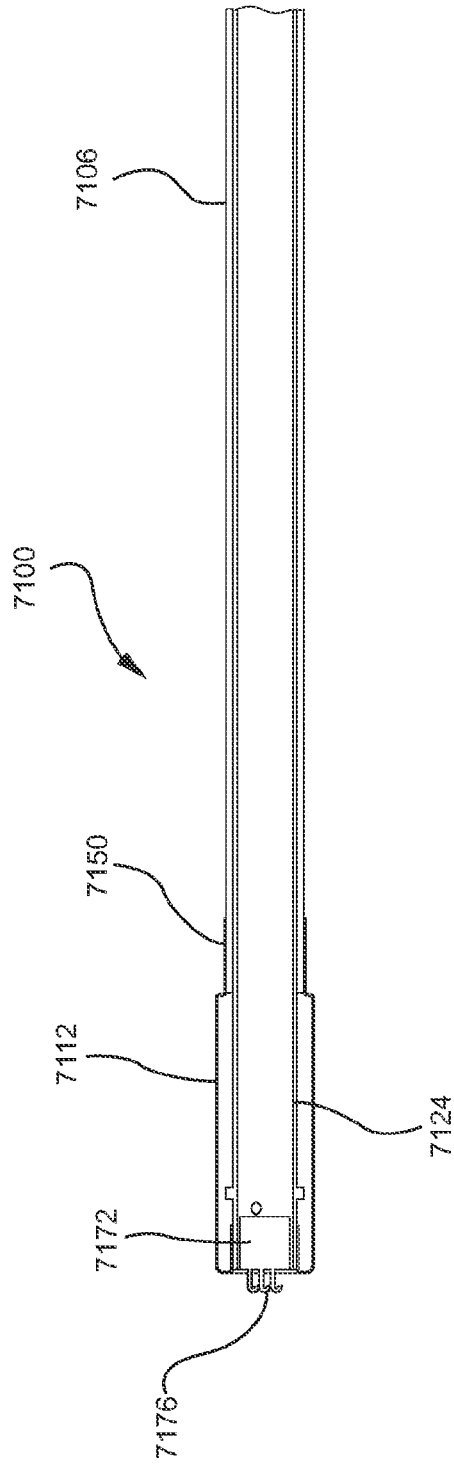
FIGS. 31A and 31B show cross-sectional views of a distal end of an instrument for controlling bleeding including an inflatable balloon, in accordance with one embodiment of the invention.
Figure 31B:
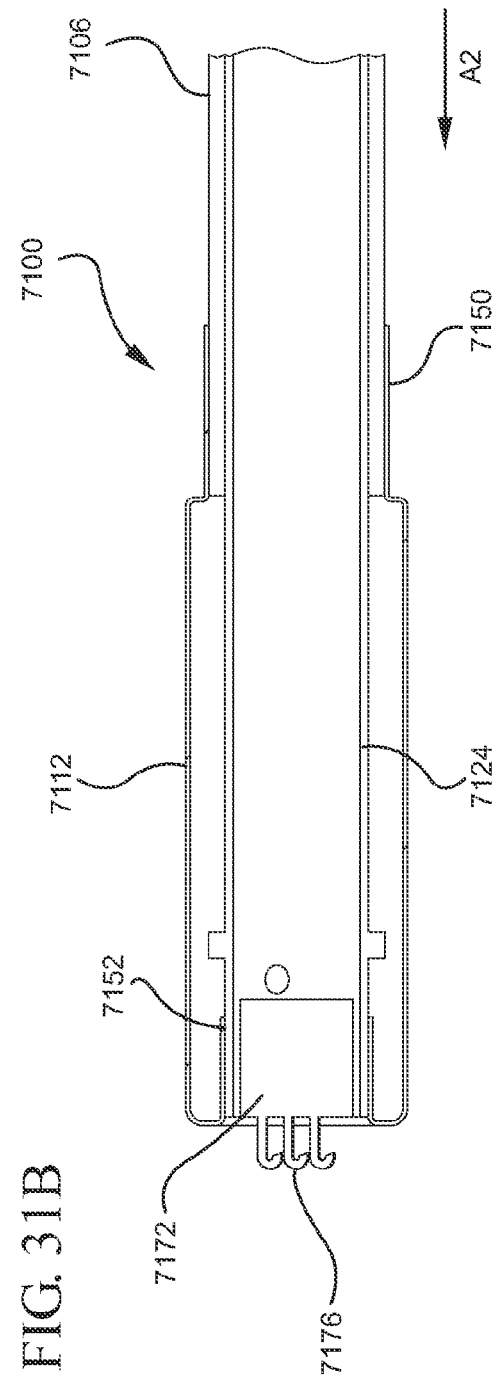

Referring to FIGS. 31A and 31B, in one embodiment, an instrument 7100 for controlling bleeding includes a plug 7172 that forms an air-tight seal at a distal end of an inner shaft 7124. The plug 7172 includes hook-like barbs 7176 that are adapted to hold a hemostat at the distal end of the instrument. The instrument includes an inflatable balloon 7112 having a proximal end 7150 secured to a distal end of an outer shaft 7106 and a distal end 7152 that is inverted, with the inverted distal end being secured to the distal end of the inner shaft 7124. Referring to FIG. 31B, the outer shaft 7106 is movable in a distal direction A2 relative to the inner shaft 7124.

Referring to FIG. 32, the inflatable balloon 7112 may be inflated using one of the actuators described herein. When the balloon is initially inflated, it has the spherical shape shown in FIG. 32. The outer shaft 7106 may then be moved distally relative to the inner shaft 7124 to provide the balloon 7112 with a more toroidal shape as shown in FIG. 33. The leading face 7196 of the balloon has a larger, flatter surface area for applying pressure to a hemostat at a surgical site.

In one embodiment, the present invention enables the shape of an inflated balloon to be changed so as to maximize the surface area available for selectively applying tamponade pressure to a medical patch. Thus, the present invention enables an increased balloon surface area to be applied to a medical patch. This may be particularly useful for applying pressure on hemostatic dressings, flowable hemostats, and flowable sealants.

Figure 34:
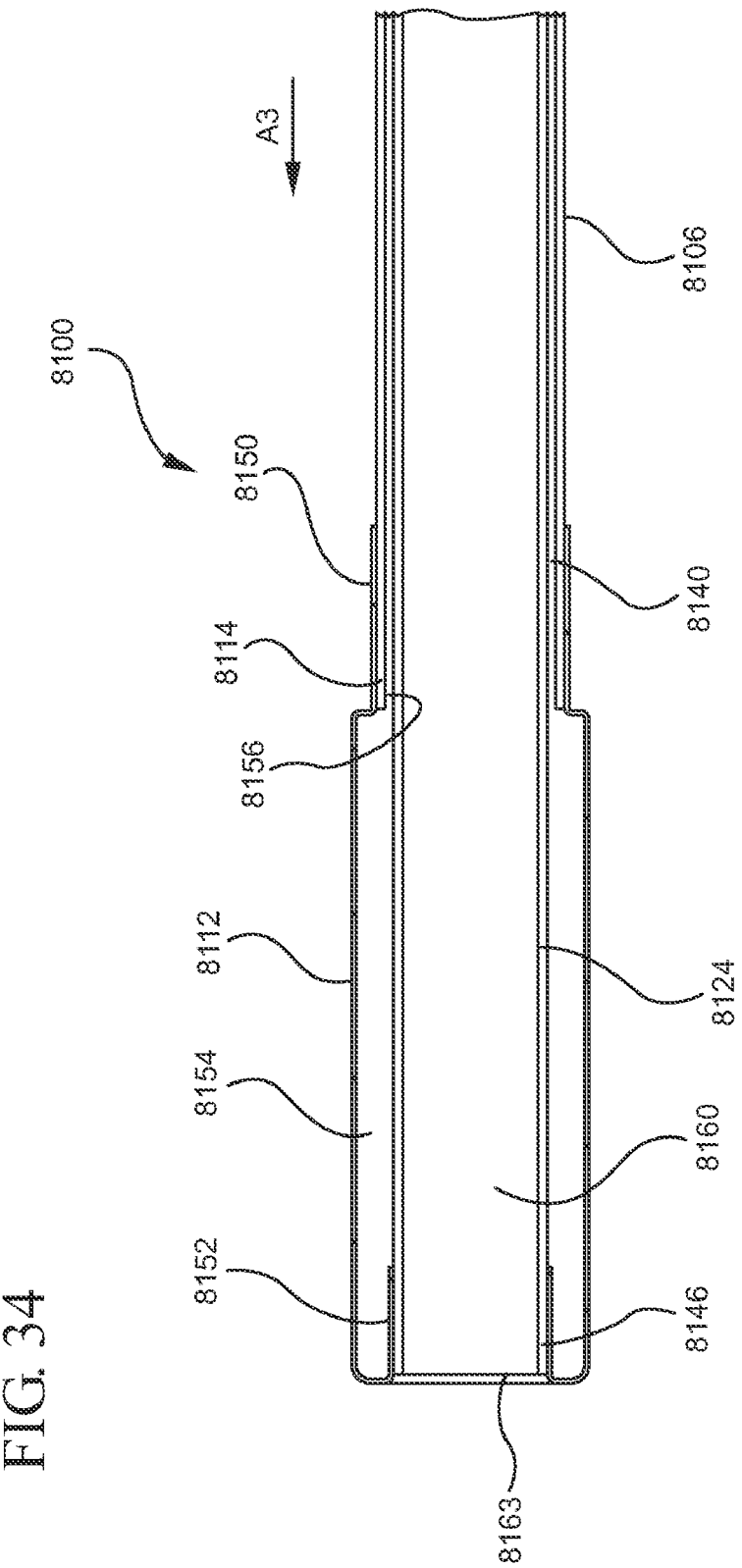
FIG. 34 shows a cross-sectional view of an instrument for controlling bleeding including an outer shaft that is movable relative to an inner shaft, in accordance with one embodiment of the present invention.

Referring to FIG. 34, in one embodiment, a distal end of an instrument 8100 for controlling bleeding includes the outer shaft 8106, an inner shaft 8124, and a first conduit 8140 that extends between the outer and inner shafts. A distal end 8148 of the inner shaft preferably extends beyond the distal end 8114 of the outer shaft 8106. The instrument includes an inflatable balloon 8112 having a proximal end 8150 secured to the distal end 8114 of the outer shaft 8106, and a distal end 8152 that is secured to the distal end 8148 of the inner shaft 8124. The proximal end 8150 of the inflatable balloon 8112 is preferably secured to an outer surface of the outer shaft 8106. The distal end 8152 of the inflatable balloon 8112 is preferably inverted, and the inverted distal end is preferably secured to an outer surface of the inner shaft 8124 at the distal end 8148 of the inner shaft 8124. The above-described structure desirably forms an air-tight compartment 8154 inside the inflatable balloon 8112. The distal end 8156 of the first conduit 8140 is preferably in communication with the air-tight compartment 8154. Fluid such as air may be directed through the first conduit 8140 and into the compartment 8154 for inflating the balloon 8112. When it is desirable to deflate the balloon 8112, the fluid may be removed from the balloon through the first conduit 8140. In the particular embodiment shown in FIG. 34, the outer and inner shafts 8106, 8124 move relative to one another for changing the shape of the balloon 8112. In one preferred embodiment, after the balloon 8112 is inflated, the outer shaft 8106 moves in the distal direction A3 relative to the inner shaft 8124 for changing the shape of the balloon.

The inner shaft 8124 has a central lumen 8160 that defines a distal opening 8163 at the distal end 8148 of the inner shaft. As will be described in more detail below, in one embodiment a stylet is passable through the central lumen 8160 so that a distal end of the stylet extends from the distal opening 8163 at the distal end of the instrument 8100. The stylet may be used to secure a medical textile such as a hemostat at the distal end of the instrument. In another embodiment, a flowable material such as a flowable hemostat material may pass through the central lumen and be dispensed from the distal opening 8163 at the distal end of the central lumen 8160. In still another embodiment, a sealant dispensing system may be inserted into the central lumen 8160 such as by inserting the catheter of the sealant dispensing system through the central lumen 8160.

FIG. 35A shows the outer shaft 8106 in a retracted position relative to the inner shaft 8124, thereby providing the inflated balloon 8112 with a spherical shape. In FIG. 35B, the outer shaft 8106 has been moved in a distal direction A3 relative to the inner shaft 8124, thereby changing the shape of the balloon. In one embodiment, the balloon changes into a toroidal shape having a flatter leading face 8196. The flatter leading face 8196 provides a larger surface area for applying tamponade pressure to a hemostat or a sealant. As noted above, the central lumen 8160 extending to the distal end of the inner shaft 8124 enables a stylet or a flowable material to be passed through the distal opening 8163 at the distal end of the central lumen 8160.

Figure 36B:
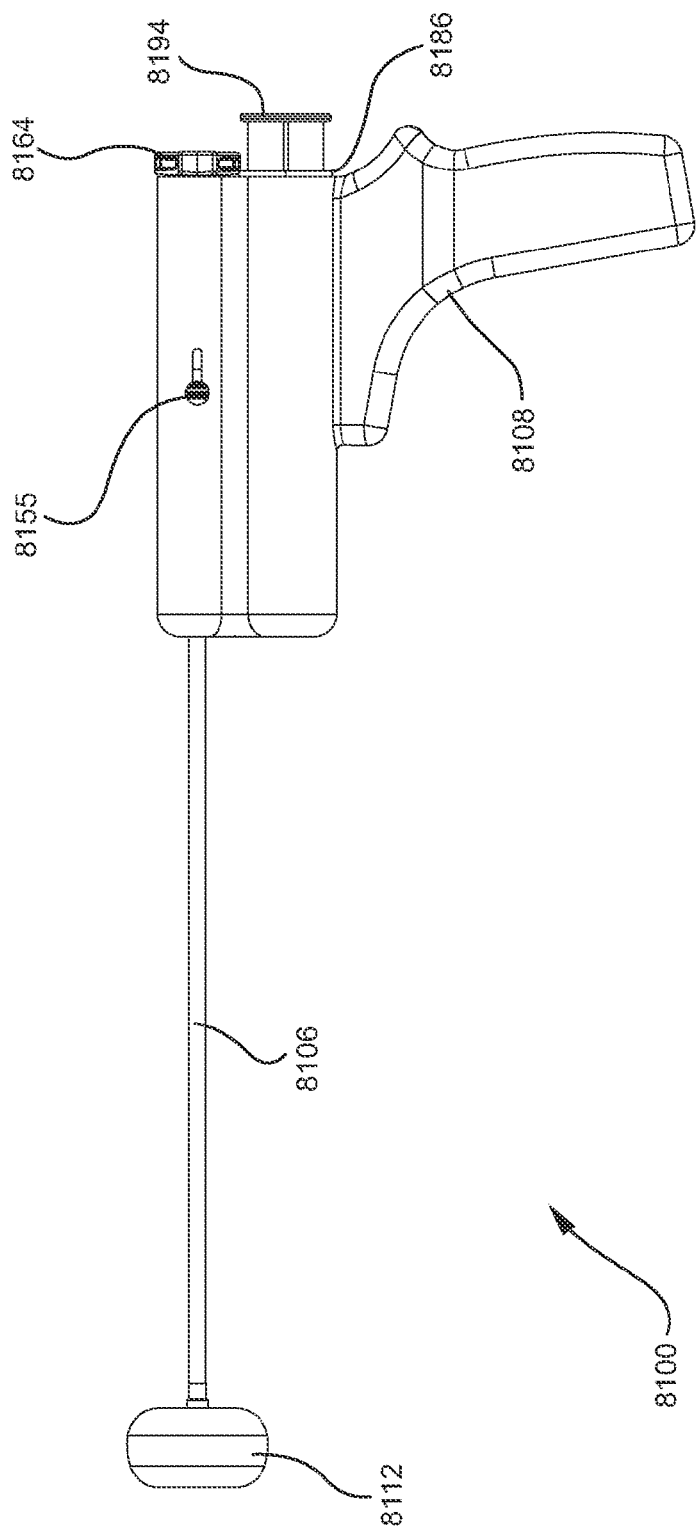

Referring to FIGS. 36A and 36B, in one embodiment, an instrument 8100 for controlling bleeding may combine one or more of the features disclosed in the above embodiments with the moveable outer shaft embodiment of FIGS. 34 and 35A-35B. In one embodiment, the instrument includes a handle 8108, and a first actuator 8186 coupled with the handle. The first actuator 8186 has a plunger 8194 that is depressible for inflating an inflatable balloon 8112. The instrument 8100 also includes a second connection port that is aligned with the central lumen that extends through the inner shaft. The second connection port is adapted to receive a stylet 8164. The distal end of the stylet 8164 may include barbs for holding a hemostat at the distal end of the stylet. The instrument 8100 also preferably includes a shaft actuator 8155 for moving the outer shaft 8106 relative to the inner shaft. In FIG. 36A, the shaft actuator 8155 is in a first position whereby the outer shaft is retracted relative to the inner shaft. In FIG. 36B the shaft actuator 8155 has been moved to a second position for moving the outer shaft distally relative to the inner shaft to change the shape of the inflated balloon 8112.

Figure 37A:
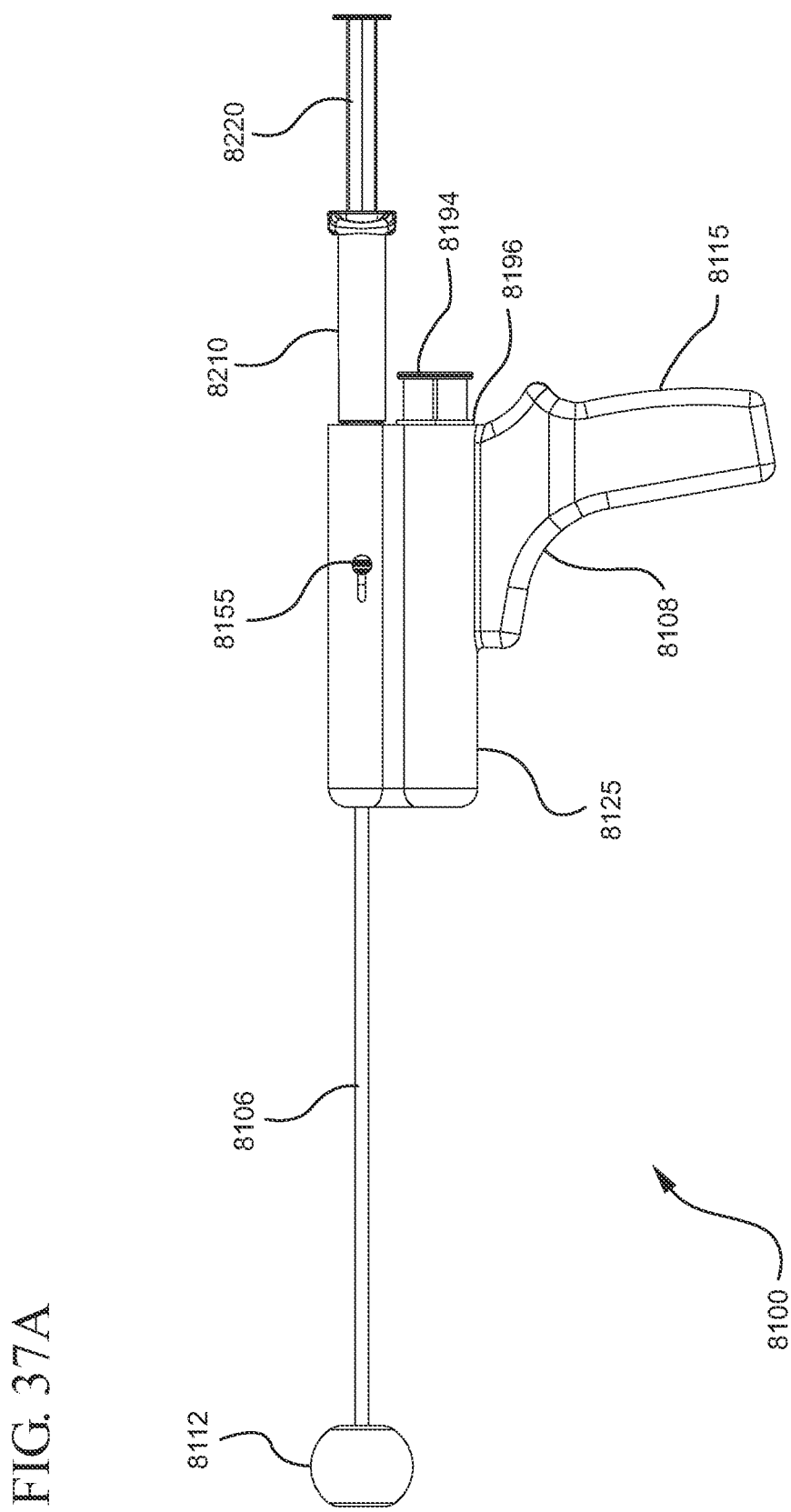
FIGS. 37A and 37B show front elevational views of an instrument for controlling bleeding, in accordance with one embodiment of the present invention.
Figure 37B:
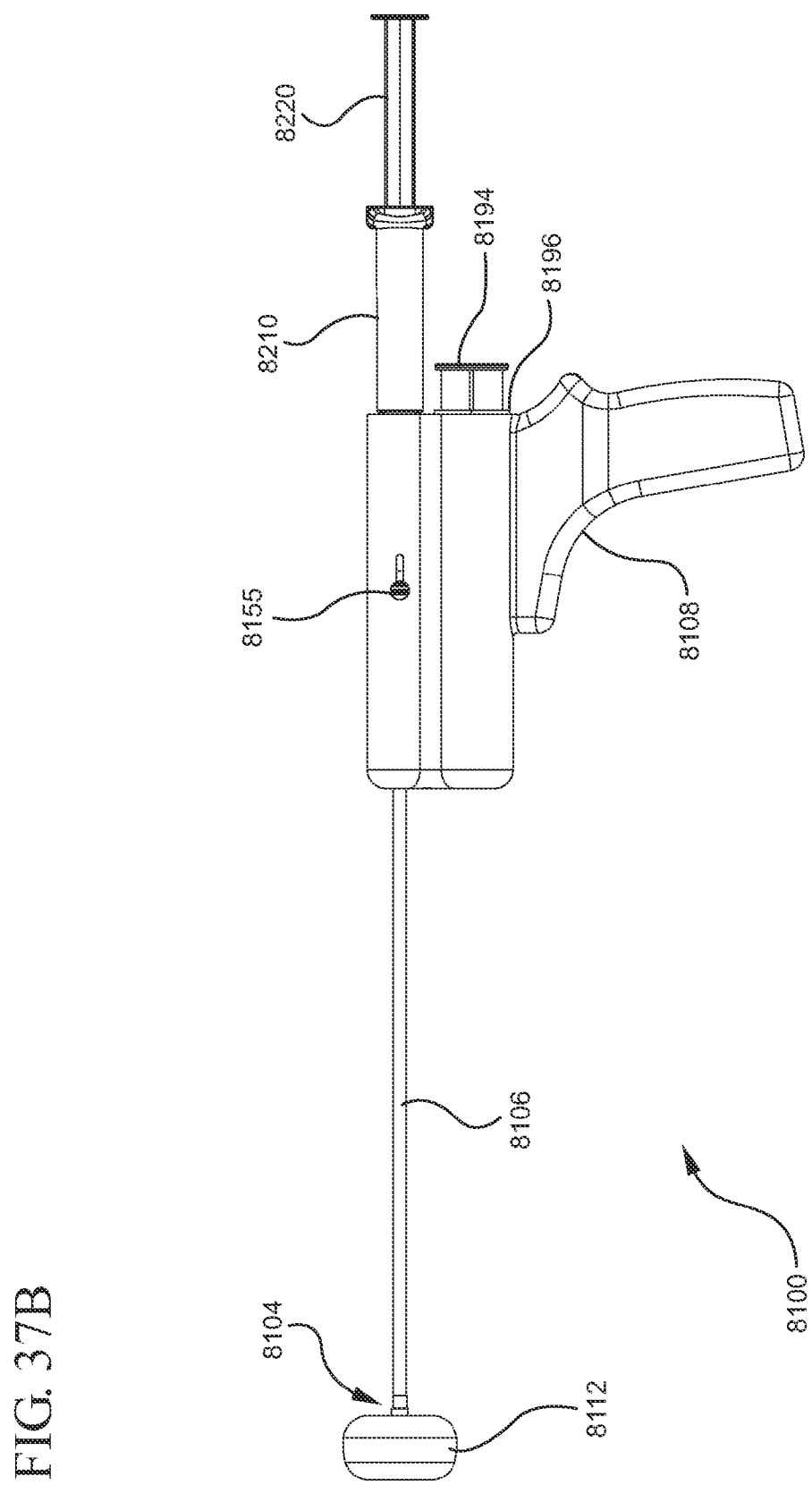

FIGS. 37A and 37B show another embodiment of the present invention whereby the stylet 8164 is removed from the second connection port and replaced by a second actuator 8210 containing a flowable material. The second actuator 8210 may include a syringe having a barrel containing a flowable hemostat material and a depressible plunger 8220 for dispensing the flowable hemostat material from the barrel. In one embodiment, the second actuator 8210 may include a sealant dispensing system having one or more syringes containing a sealant and a catheter that is extendable through the central lumen of the inner shaft. As in the above embodiment, the instrument includes a handle 8108 having the first actuator 8186 with a depressible plunger 8194 for inflating the balloon 8112. The instrument 8100 includes a shaft actuator 8155 movable between first and second positions for moving the outer shaft 8106 relative to the inner shaft for changing the shape of the balloon 8112.

Although various embodiments of the present invention have been disclosed herein, it is contemplated that other embodiments may combine one or more features of any one of the embodiments and still fall within the scope of the present invention. One embodiment of the present invention may incorporate one or more of the features or method steps disclosed in commonly assigned U.S. patent application Ser. No. 12/049,849, entitled "APPLICATOR INSTRUMENTS FOR THE DELIVERY, DEPLOYMENT, AND TAMPONADE OF HEMOSTATS AND METHODS THEREFOR," filed Mar. 17, 2008, and U.S. patent application Ser. No. 12/049,869, entitled "APPLICATOR INSTRUMENTS HAVING PROTECTIVE CARRIERS FOR HEMOSTATS AND METHODS THEREFOR," filed Mar. 17, 2008, the disclosures of which are hereby incorporated by reference herein.

While the foregoing is directed to embodiments of the present invention, other and further embodiments of the invention may be devised without departing from the basic scope thereof.

What is claimed is:

1. An instrument for controlling bleeding comprising:
 a rigid outer shaft having a proximal end, a distal end, and a central lumen extending between the proximal and distal ends;
 a rigid inner shaft disposed within the central lumen of said outer shaft, said inner shaft having a proximal end, a distal end that extends beyond the distal end of said outer shaft, and a central lumen extending between the proximal and distal ends thereof;
 an inflatable balloon having a proximal end secured to said outer shaft and a distal end that is inverted, wherein said inverted distal end of said balloon is secured to said inner shaft;
 a first actuator in communication with said inflatable balloon for selectively inflating said balloon;
 a shaft actuator connected with at least one of said shafts for selectively moving said outer and inner shafts relative to one another, wherein upon inflation of said balloon, said shaft actuator is engageable for moving said outer and inner shafts from a first position in which said inflated balloon has a rounder leading face to a second position in which said inflated balloon has a flatter leading face, and wherein said shaft actuator is adapted to hold said outer and inner shafts in the second position for maintaining the shape of said flatter leading face of said inflated balloon as said flatter leading face is used to apply pressure for controlling bleeding; and a hemostat in contact with said inverted distal end of said balloon, wherein as said balloon is inflated said expanding balloon deploys said hemostat in contact with said inverted distal end of said balloon, and wherein said deployed hemostat conforms to said flatter leading face when said outer and inner shafts are in the second position.

2. The instrument as claimed in claim 1, further comprising a first conduit extending between said inner and outer shafts and toward the distal ends of said inner and outer shafts, wherein the first conduit has a first end in communication with said inflatable balloon and a second end in communication with said first actuator, wherein upon inflation said leading face projects distally of said distal end of said inner shaft for forming a distal-most end of said instrument.

3. The instrument as claimed in claim 2, further comprising a hub connector secured to the proximal end of said outer shaft, said hub connector having a first connection port for coupling said first actuator with the first conduit.

4. The instrument as claimed in claim 3, wherein said first actuator comprises a syringe having a barrel and a plunger, and wherein said plunger is depressible for introducing fluid into said balloon.

5. The instrument as claimed in claim 3, wherein said hub connector further comprises a second connection port that is aligned with the central lumen of said inner shaft.

6. The instrument as claimed in claim 5, further comprising a stylet having proximal and distal ends, a handle at the proximal end thereof, and hook-like barbs at the distal end thereof, wherein said stylet is insertable into said second connection port and through the central lumen of said inner shaft for positioning the hook-like barbs at the distal end of said inner shaft.

7. The instrument as claimed in claim 6, wherein said stylet further comprises threads or a tapered surface for securing said stylet to said hub connector.

8. The instrument as claimed in claim 5, further comprising a second actuator adapted to hold a flowable material, wherein said second actuator is securable to the second connection port of said hub connector.

9. The instrument as claimed in claim 8, wherein said second actuator comprises one or more barrels for holding said flowable material, one or more discharge openings alignable with the central lumen of said inner shaft, and one or more plungers that are depressible for dispensing said flowable material.

10. The instrument as claimed in claim 1, wherein said shaft actuator is engageable for selectively moving the distal ends of said shafts relative to one another for changing the shape of said inflatable balloon.

11. The instrument as claimed in claim 10, wherein said shaft actuator is adapted to selectively move the distal end of said outer shaft in a distal direction relative to the distal end of said inner shaft for changing the shape of said inflatable balloon secured to said outer and inner shafts.

12. The instrument as claimed in claim 1, wherein said hemostat is selected from the group consisting of medical textiles, flowable hemostats and flowable sealants.

13. An instrument for controlling bleeding comprising:
a single shaft having a proximal end and a distal end;
an inflatable balloon having a proximal end secured to said single shaft and a distal end that is inverted, wherein said inverted distal end of said balloon is secured to the distal end of said single shaft; and
an actuator for selectively inflating said inflatable balloon, wherein upon inflation said inflated balloon has a toroidal shape having a flattened leading face at a distal-most point of said instrument adapted to apply pressure for controlling bleeding; and a hemostat in contact with said inverted distal end of said balloon, wherein as said balloon is inflated said expanding balloon deploys said hemostat in contact with said inverted distal end of said balloon, and wherein said deployed hemostat conforms to said flattened leading face.

14. The instrument as claimed in claim 13, said instrument further comprising barbs projecting from the distal end of said shaft.

15. The instrument as claimed in claim 14, wherein said shaft has a longitudinal axis extending between the proximal and distal ends thereof, and said barbs project along the longitudinal axis.

16. The instrument as claimed in claim 13, wherein the inverted distal end of said inflatable balloon is connected to a distal-most end of said shaft.

17. The instrument as claimed in claim 13, wherein said actuator for selectively inflating said inflatable balloon is coupled with a connection port located at the proximal end of said shaft.

18. The instrument as claimed in claim 13, further comprising a valve in communication with said inflatable balloon for selectively deflating said balloon.

19. The instrument as claimed in claim 13, wherein said hemostat is selected from the group consisting of medical textiles, flowable hemostats and flowable sealants.

20. An instrument for controlling bleeding comprising:
a rigid inner shaft having a proximal end and a distal end;
a rigid outer shaft having a proximal end and a distal end, said outer shaft surrounding said inner shaft;
a first lumen extending between said inner and outer shafts;
a second lumen extending though said inner shaft to a distal opening at the distal end of said inner shaft;
an inflatable balloon secured to the distal end of said instrument, said inflatable balloon being in communication with said first lumen, wherein said balloon has a proximal end secured to said outer shaft and a distal end surrounding the distal opening of said second lumen and being secured to said inner shaft, and wherein the distal end of said balloon is inverted and the inverted distal end of said balloon is secured to the distal end of said inner shaft;
a shaft actuator connected with at least one of said shafts for selectively moving said shafts relative to one another, wherein upon inflation of said balloon, said shaft actuator is engageable for moving said shafts from a first position in which said inflated balloon has a rounder leading face to a second position in which said inflated balloon has a flatter leading face, and wherein said shaft actuator is adapted to hold said shafts in the second position for maintaining the shape of said flatter leading face of said inflated balloon as said flatter leading face is used to apply pressure for controlling bleeding; and a hemostat in contact with said inverted distal end of said balloon, wherein as said balloon is inflated said expanding balloon deploys said hemostat in contact with said inverted distal end of said balloon, and wherein said deployed hemostat conforms to said flatter leading face when said outer and inner shafts are in the second position.

21. The instrument as claimed in claim 20, further comprising:
a first actuator in communication with said first lumen for selectively inflating said balloon; and
a second actuator in communication with said second lumen for introducing a flowable material into said second lumen for discharging said flowable material from the distal opening at the distal end of said inner shaft.

22. The instrument as claimed in claim 21, wherein said flowable material is selected from the group consisting of a sealant, and a flowable hemostat material.

23. The instrument as claimed in claim 22, wherein said first actuator comprises an inflation syringe and said second actuator comprises a syringe filled with the flowable material.

24. The instrument as claimed in claim 23, further comprising a hub connector secured to the proximal end of said outer shaft, said hub connector including a first connection port in communication with said first lumen and a second connection port in communication with said second lumen, wherein said first actuator is coupled with said first connection port and said second actuator is coupled with said second connection port.

25. The instrument as claimed in claim 21, wherein said shaft actuator is coupled with said outer shaft for moving the distal end of said outer shaft distally relative to the distal end of said inner shaft.

26. The instrument as claimed in claim 20, wherein said hemostat is selected from the group consisting of medical textiles, flowable hemostats and flowable sealants.

* * * * *